(12) United States Patent
Liu-Bujalski et al.

(10) Patent No.: US 9,738,648 B2
(45) Date of Patent: Aug. 22, 2017

(54) PYRIDINES, PYRIMIDINES, AND PYRAZINES, AS BTK INHIBITORS AND USES THEREOF

(71) Applicant: Merck Patent GmbH, Darmstadt (DE)

(72) Inventors: Lesley Liu-Bujalski, Bedford, MA (US); Ngan Nguyen, Arlington, MA (US); Hui Qiu, Acton, MA (US); Reinaldo Jones, Lowell, MA (US); Igor Mochalkin, San Diego, CA (US); Richard D. Caldwell, Brookline, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/904,547

(22) PCT Filed: Jul. 30, 2014

(86) PCT No.: PCT/US2014/048810
§ 371 (c)(1),
(2) Date: Jan. 12, 2016

(87) PCT Pub. No.: WO2015/017502
PCT Pub. Date: Feb. 5, 2015

(65) Prior Publication Data
US 2016/0159804 A1 Jun. 9, 2016

Related U.S. Application Data

(60) Provisional application No. 61/860,401, filed on Jul. 31, 2013.

(51) Int. Cl.
*A01N 43/90* (2006.01)
*A61K 31/519* (2006.01)
*C07D 487/00* (2006.01)
*C07D 487/04* (2006.01)

(52) U.S. Cl.
CPC .......... *C07D 487/04* (2013.01); *A61K 31/519* (2013.01)

(58) Field of Classification Search
None
See application file for complete search history.

(56) References Cited

U.S. PATENT DOCUMENTS

| | | |
|---|---|---|
| 4,650,750 A | 3/1987 | Giese |
| 4,709,016 A | 11/1987 | Giese |
| 5,360,819 A | 11/1994 | Giese |
| 5,516,931 A | 5/1996 | Giese |
| 5,602,273 A | 2/1997 | Giese |
| 5,604,104 A | 2/1997 | Giese |
| 5,610,020 A | 3/1997 | Giese |
| 5,650,270 A | 7/1997 | Giese |

FOREIGN PATENT DOCUMENTS

| | | |
|---|---|---|
| EP | 1752457 A1 | 2/2007 |
| EP | 2548877 A1 | 1/2013 |
| WO | 2006010264 A1 | 2/2006 |
| WO | 2007004749 A1 | 1/2007 |
| WO | 2011093672 A2 | 8/2011 |
| WO | 2012158785 A1 | 11/2012 |
| WO | 2012158795 A1 | 11/2012 |
| WO | 2013010868 A1 | 1/2013 |

OTHER PUBLICATIONS

Baskin et al., Proc. Natl. Acad. Sci. USA, 2007, 104:16793-16797.
Berge et al., J. Pharmaceutical Sciences, 1977, 66(1):1-19.
Ellmeier et al., J. Exp. Med. 2000, 192(11):1611-1623.
Feldhahn et al., J. Exp. Med., 2005, 201(11):1837-1852.
Foster, Adv. Drug Res., 1985, 14:1-40.
Gillette et al., Biochemistry, 1994, 33(10):2927-2937.
Hanzlik et al., J. Org. Chem., 1990, 55(13):3992-3997.
Horwood et al., J Exp Med, 2003, 197(12):1603-1611.
Hunter T., Cell, 1987, 50(5):823-829.
Islam and Smith, Immunol. Rev., 2000, 178:49-63.
Iwaki et al., J. Biol. Chem., 2005, 280(48):40261-40270.
Jansson and Holmdahl, Clin. Exp. Immunol., 1993, 94:459-465.
Jarman et al., Carcinogenesis, 1995, 16(4):683-688.
Kawakami et al., Journal of Leukocyte Biology, 1999, 65:286-290.
Khan et al., Immunity, 1995, 3:283-299.
Lindvall et al., Immunol. Rev., 2005, 203:200-215.
Pan et al., Chem. Med Chem., 2007, 2:58-61.
Rastetter et al., Annu Rev Med, 2004, 55:477-503.
Reider et al., J. Org. Chem., 1987, 52:3326-3334.
Rosen et al., New Eng. J. Med., 1995, 333(7):431-440.
Rostovtsev et al., Angew. Chem. Int. Ed. 2002, 41:2596-99.
Smith M.B. and March J., "March's Advanced Organic Chemistry", 5th Ed., Ed., John Wiley & Sons, New York, 2001.
Sorrell Thomas Organic Chemistry University Science Books, Sausalito, 1999.
Sun et al., Bioconjugate Chem., 2006, 17(1):52-57.
Vassilev et al., J. Biol. Chem., 1999, 274(3):1646-1656.
Vihinen et al., Frontiers in Bioscience, 2000, 5:d917-928.
Periodic Table of the Elements, CAS version, Handbook of Chemistry and Physics, 75th Ed.
Ishikawa et al., Journal of Medicinal Chemistry, 54: 8030-8050 (2011).

*Primary Examiner* — Jeffrey H Murray
(74) *Attorney, Agent, or Firm* — Dwight D. Kim; EMD Serono Research and Development Institiute

(57) ABSTRACT

The present invention relates to pyridine, pyrimidine, and pyrazine compounds, and pharmaceutically acceptable compositions thereof, useful as BTK inhibitors.

13 Claims, No Drawings

PYRIDINES, PYRIMIDINES, AND PYRAZINES, AS BTK INHIBITORS AND USES THEREOF

RELATED APPLICATIONS

This application is a U.S. national stage application of PCT international application PCT/US14/48810, filed on Jul. 30, 2014, which claims the benefit of U.S. Provisional Application U.S. Ser. No. 61/860,401, filed on Jul. 31, 2013. The entire contents of the aforementioned applications are incorporated by reference herein in its entirety.

TECHNICAL FIELD OF THE INVENTION

The present invention relates to pyridine, pyrimidine and pyrazine compounds that are useful as inhibitors of Bruton's Tyrosine Kinase (BTK). The invention also provides pharmaceutically acceptable compositions comprising compounds of the present invention and methods of using said compositions in the treatment of various disorders.

BACKGROUND OF THE INVENTION

Protein kinases constitute one of the largest families of human enzymes and regulate many different signaling processes by adding phosphate groups to proteins (T. Hunter, Cell 1987 50:823-829). Specifically, tyrosine kinases phosphorylate proteins on the phenolic moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling, they provide a target to modulate cellular function with small molecular kinase inhibitors and thus make good drug targets. In addition to treatment of kinase-mediated disease processes, selective and efficacious inhibitors of kinase activity are also useful for investigation of cell signaling processes and identification of other cellular targets of therapeutic interest.

There is good evidence that B-cells play a key role in the pathogenesis of autoimmune and/or inflammatory disease. Protein-based therapeutics that deplete B cells such as Rituxan are effective against autoantibody-driven inflammatory diseases such as rheumatoid arthritis (Rastetter et al. Annu Rev Med 2004 55:477). Therefore inhibitors of the protein kinases that play a role in B-cell activation should be useful therapeutics for B-cell mediated disease pathology, such as autoantibody production.

Signaling through the B-cell receptor (BCR) controls a range of B-cell responses including proliferation and differentiation into mature antibody producing cells. The BCR is a key regulatory point for B-cell activity and aberrant signaling can cause deregulated B-cell proliferation and formation of pathogenic autoantibodies that lead to multiple autoimmune and/or inflammatory diseases. Bruton's Tyrosine Kinase (BTK) is a non-BCR associated kinase that is membrane proximal and immediately downstream from BCR. Lack of BTK has been shown to block BCR signaling and therefore inhibition of BTK could be a useful therapeutic approach to block B-cell mediated disease processes. Also, BTK has been reported to play a role in apoptosis (Islam and Smith Immunol. Rev. 2000 178:49,) and thus BTK inhibitors would be useful for the treatment of certain B-cell lymphomas and leukemias (Feldhahn et al. J. Exp. Med. 2005 201:1837).

BTK is a member of the Tec family of tyrosine kinases, and has been shown to be a critical regulator of early B-cell development and mature B-cell activation and survival (Khan et al. Immunity 1995 3:283; Ellmeier et al. J. Exp. Med. 2000 192:1611). Mutation of BTK in humans leads to the condition X-linked agammaglobulinemia (XLA) (reviewed in Rosen et al. New Eng. J. Med. 1995 333:431 and Lindvall et al. Immunol. Rev. 2005 203:200). These patients are immunocompromised and show impaired maturation of B-cells, decreased immunoglobulin and peripheral B-cell levels, diminished T-cell independent immune responses as well as attenuated calcium mobilization following BCR stimulation.

Evidence for a role for BTK in autoimmune and inflammatory diseases has also been provided by BTK-deficient mouse models. In preclinical murine models of systemic lupus erythematosus (SLE), BTK-deficient mice show marked amelioration of disease progression. In addition, BTK-deficient mice are resistant to collagen-induced arthritis (Jansson and Holmdahl Clin. Exp. Immunol. 1993 94:459). A selective BTK inhibitor has demonstrated dose-dependent efficacy in a mouse arthritis model (Z. Pan et al., Chem. Med Chem. 2007 2:58-61).

BTK is also expressed by cells other than B-cells that may be involved in disease processes. BTK is key component of Fc-gamma signaling in myeloid cells. For example, BTK is expressed by mast cells and BTK-deficient bone marrow derived mast cells demonstrate impaired antigen induced degranulation (Iwaki et al. J. Biol. Chem. 2005 280:40261). This shows BTK could be useful to treat pathological mast cells responses such as allergy and asthma. Also monocytes from XLA patients, in which BTK activity is absent, show decreased TNF alpha production following stimulation (Horwood et al. J Exp Med 197:1603, 2003). Therefore TNF alpha mediated inflammation could be modulated by small molecular BTK inhibitors.

SUMMARY OF THE INVENTION

It has now been found that compounds of this invention, and pharmaceutically acceptable compositions thereof, are effective as inhibitors of BTK. Such compounds have general formula I:

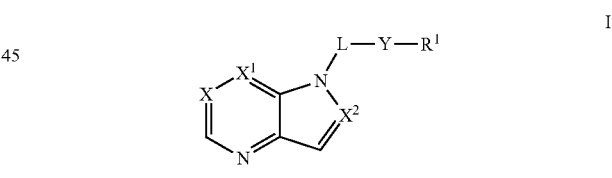

or a pharmaceutically acceptable salt thereof, wherein each of X, $X^1$, $X^2$, Y, L, and $R^1$, is as defined and described in embodiments herein.

Compounds of the present invention, and pharmaceutically acceptable compositions thereof, are useful for treating a variety of diseases, disorders or conditions, associated with BTK. Such diseases, disorders, or conditions include those described herein.

DETAILED DESCRIPTION OF CERTAIN EMBODIMENTS

1. General Description of Compounds of the Invention

In certain aspects, the present invention provides for inhibitors of BTK. In some embodiments, such compounds include those of the formulae described herein, or a pharmaceutically acceptable salt thereof, wherein each variable is as defined and described herein.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Exemplary aliphatic groups are linear or branched, substituted or unsubstituted $C_1$-$C_8$ alkyl, $C_2$-$C_8$ alkenyl, $C_2$-$C_8$ alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, or phosphorus (including, any oxidized form of nitrogen, sulfur, or phosphorus; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" is used interchangeably with the term "aryl ring". In certain embodiments of the present invention, "aryl" refers to an aromatic ring system. Exemplary aryl groups are phenyl, biphenyl, naphthyl, anthracyl and the like, which optionally includes one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 t electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group is optionally mono- or bicyclic. The term "heteroaryl" is used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen is N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group is optionally mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, certain compounds of the invention contain "optionally substituted" moieties. In general, the term "substituted", whether preceded by the term "optionally" or not, means that one or more hydrogens of the designated moiety are replaced with a suitable substituent. "Substituted" applies to one or more hydrogens that are either explicit or implicit from the structure (e.g.,

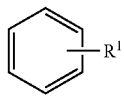

refers to at least

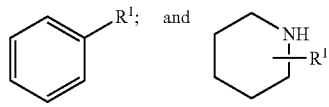

refers to at least

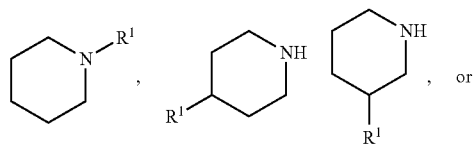

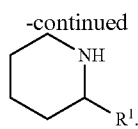

Unless otherwise indicated, an "optionally substituted" group has a suitable substituent at each substitutable position of the group, and when more than one position in any given structure is substituted with more than one substituent selected from a specified group, the substituent is either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently deuterium; halogen; —(CH$_2$)$_{0-4}$R°; —(CH$_2$)$_{0-4}$R°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which are optionally substituted with R°; —(CH$_2$)$_{0-4}$O(CH$_2$)$_{0-1}$Ph which is optionally substituted with R°; —CH=CHPh, which is optionally substituted with R°; —(CH$_2$)$_{0-4}$O(CH$_2$)$_{0-1}$-pyridyl which is optionally substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° is optionally substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which is optionally substituted as defined below.

Suitable monovalent substituents on R° (or the ring formed by taking two independent occurrences of R° together with their intervening atoms), are independently deuterium, halogen, —(CH$_2$)$_{0-2}$R•, -(haloR•), —(CH$_2$)$_{0-2}$OH, —(CH$_2$)$_{0-2}$OR, —(CH$_2$)$_{0-2}$CH(OR•)$_2$; —O(haloR•), —CN, —N$_3$, —(CH$_2$)$_{0-2}$C(O)R•, —(CH$_2$)$_{0-2}$C(O)OH, —(CH$_2$)$_{0-2}$C(O)OR•, —(CH$_2$)$_{0-2}$SR•, —(CH$_2$)$_{0-2}$SH, —(CH$_2$)$_{0-2}$NH$_2$, —(CH$_2$)$_{0-2}$NHR•, —(CH$_2$)$_{0-2}$NR•$_2$, —NO$_2$, —SiR•$_3$, —OSiR•$_3$, —C(O)SR•, —(C$_{1-4}$ straight or branched alkylene)C(O)OR•, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which is substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which is optionally substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which is optionally substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

In certain embodiments, the terms "optionally substituted", "optionally substituted alkyl," "optionally substituted "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with typical substituents including, but not limited to:

—F, —Cl, —Br, —I, deuterium,

—OH, protected hydroxy, alkoxy, oxo, thiooxo,

—NO$_2$, —CN, CF$_3$, N$_3$,

—NH$_2$, protected amino, —NH alkyl, —NH alkenyl, —NH alkynyl, —NH cycloalkyl, —NH— aryl, —NH-heteroaryl, —NH-heterocyclic, -dialkylamino, -diarylamino, -diheteroarylamino, —O— alkyl, —O— alkenyl, —O— alkynyl, —O— cycloalkyl, —O-aryl, —O-heteroaryl, —O— heterocyclic, —C(O)— alkyl, —C(O)— alkenyl, —C(O)— alkynyl, —C(O)— carbocyclyl, —C(O)-aryl, —C(O)— heteroaryl, —C(O)-heterocyclyl, —CONH$_2$, —CONH— alkyl, —CONH— alkenyl, —CONH— alkynyl, —CONH-carbocyclyl, —CONH-aryl, —CONH-heteroaryl, —CONH-heterocyclyl, —OCO$_2$— alkyl, —OCO$_2$— alkenyl, —OCO$_2$— alkynyl, —OCO$_2$— carbocyclyl, —OCO$_2$-aryl, —OCO$_2$-heteroaryl, —OCO$_2$-heterocyclyl, —OCONH$_2$, —OCONH— alkyl, —OCONH— alkenyl, —OCONH— alkynyl, —OCONH— carbocyclyl, —OCONH— aryl, —OCONH— heteroaryl, —OCONH— heterocyclyl, —NHC(O)— alkyl, —NHC(O)— alkenyl, —NHC(O)— alkynyl, —NHC(O)— carbocyclyl, —NHC(O)-aryl, —NHC(O)-heteroaryl, —NHC(O)-heterocyclyl, —NHCO$_2$— alkyl, —NHCO$_2$— alkenyl, —NHCO$_2$— alkynyl, —NHCO$_2$— carbocyclyl, —NHCO$_2$— aryl, —NHCO$_2$— heteroaryl, —NHCO$_2$-heterocyclyl, —NHC(O)NH$_2$, —NHC(O)NH— alkyl, —NHC(O)NH— alkenyl, —NHC(O)NH— alkenyl, —NHC(O)NH— carbocyclyl, —NHC(O)NH-aryl, —NHC(O)NH-heteroaryl, —NHC(O)NH— heterocyclyl, NHC(S)NH$_2$, —NHC(S)NH— alkyl, —NHC(S)NH— alkenyl, —NHC(S)NH— alkynyl, —NHC(S)NH— carbocyclyl, —NHC(S)NH-aryl, —NHC(S)NH-heteroaryl, —NHC(S)NH-heterocyclyl, —NHC(NH)NH$_2$, —NHC(NH)NH— alkyl, —NHC(NH)NH—-alkenyl, —NHC(NH)NH— alkenyl, —NHC(NH)NH— carbocyclyl, —NHC(NH)NH-aryl, —NHC(NH)NH-heteroaryl, —NHC(NH)NH— heterocyclyl, —NHC(NH)— alkyl, —NHC(NH)— alkenyl, —NHC(NH)— alkenyl, —NHC(NH)— carbocyclyl, —NHC(NH)-aryl, —NHC(NH)-heteroaryl, —NHC(NH)-heterocyclyl, —C(NH)NH— alkyl, —C(NH)NH— alkenyl, —C(NH)NH— alkynyl, —C(NH)NH— carbocyclyl, —C(NH)NH-aryl, —C(NH)NH-heteroaryl, —C(NH)NH-heterocyclyl, —S(O)— alkyl, —S(O)— alkenyl, —S(O)— alkynyl, —S(O)— carbocyclyl, —S(O)-aryl, —S(O)— heteroaryl, —S(O)-heterocyclyl —SO$_2$NH$_2$, —SO$_2$NH— alkyl, —SO$_2$NH— alkenyl, —SO$_2$NH— alkynyl, —SO$_2$NH— carbocyclyl, —SO$_2$NH— aryl, —SO$_2$NH— heteroaryl, —SO$_2$NH— heterocyclyl, —NHSO$_2$— alkyl, —NHSO$_2$— alkenyl, —NHSO$_2$— alkynyl, —NHSO$_2$— carbocyclyl, —NHSO$_2$— aryl, —NHSO$_2$-heteroaryl, —NHSO$_2$-heterocyclyl,

—CH$_2$NH$_2$, —CH$_2$SO$_2$CH$_3$,

-mono-, di-, or tri-alkyl silyl,

-alkyl, -alkenyl, -alkynyl, -aryl, -arylalkyl, -heteroaryl, -heteroarylalkyl, heterocycloalkyl, -cycloalkyl, -carbocyclic, -heterocyclic, polyalkoxyalkyl, polyalkoxy, -methoxymethoxy, -methoxyethoxy, —SH, —S— alkyl, —S— alkenyl, —S— alkynyl, —S— carbocyclyl, —S— aryl, —S-heteroaryl, —S-heterocyclyl, or methylthiomethyl.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. In some embodiments, the group comprises one or more deuterium atoms.

There is furthermore intended that a compound of the formula I includes isotope-labeled forms thereof. An isotope-labeled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phosphorus, fluorine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the formula I, a prodrug, thereof or a pharmaceutically acceptable salt of either which contains one or more of the above-mentioned isotopes and/or other isotopes of other atoms is intended to be part of the present invention. An isotope-labeled compound of the formula I can be used in a number of beneficial ways. For example, an isotope-labeled compound of the formula I into which, for example, a radioisotope, such as $^3H$ or $^{14}C$, has been incorporated, is suitable for medicament and/or substrate tissue distribution assays. These radioisotopes, i.e. tritium ($^3H$) and carbon-14 ($^{14}C$), are particularly preferred owing to simple preparation and excellent detectability. Incorporation of heavier isotopes, for example deuterium ($^2H$), into a compound of the formula I has therapeutic advantages owing to the higher metabolic stability of this isotope-labeled compound. Higher metabolic stability translates directly into an increased in vivo half-life or lower dosages, which under most circumstances would represent a preferred embodiment of the present invention. An isotope-labeled compound of the formula I can usually be prepared by carrying out the procedures disclosed in the synthesis schemes and the related description, in the example part and in the preparation part in the present text, replacing a non-isotope-labeled reactant by a readily available isotope-labeled reactant.

Deuterium ($^2H$) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D=2-7$ are typical. If this rate difference is successfully applied to a com-pound of the formula I that is susceptible to oxidation, the profile of this compound in vivo can be drastically modified and result in improved pharmacokinetic properties.

When discovering and developing therapeutic agents, the person skilled in the art is able to optimize pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t/2), concentration at maximum therapeutic effect ($C_{max}$), area under the dose response curve (AUC), and F; and in terms of reduced clearance, dose and materials costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favorable and accurate determination of the extent of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula I can also be used to achieve a favorable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

As used herein, the term "modulator" is defined as a compound that binds to and/or inhibits the target with measurable affinity. In certain embodiments, a modulator has an $IC_{50}$ and/or binding constant of less about 50 µM, less than about 1 µM, less than about 500 nM, less than about 100 nM, or less than about 10 nM.

The terms "measurable affinity" and "measurably inhibit," as used herein, means a measurable change in BTK activity between a sample comprising a compound of the present invention, or composition thereof, and BTK, and an equivalent sample comprising BTK, in the absence of said compound, or composition thereof.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

3. Description of Exemplary Compounds

According to one aspect, the present invention provides a compound of formula I,

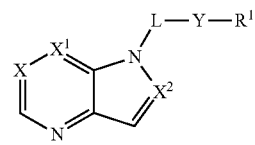

or a pharmaceutically acceptable salt thereof, wherein:
X is N or $CR^2$;
$X^1$ is N or $CR^2$;
$X^2$ is N or $CR^2$;
each $R^2$ is independently selected from —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;
each R is independently hydrogen, $C_{1-6}$ aliphatic, $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or
two R groups on the same atom are taken together with the atom to which they are attached to form a $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;
L is a divalent group selected from $C_{1-6}$ aliphatic, $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, and a 5-6 membered monocyclic heteroaryl ring having 1-4 heteroatoms independently selected from nitrogen, oxygen, or sulfur; each of which is optionally substituted; or L is a divalent group selected from $C_{1-6}$ aliphatic-$C_{3-10}$ aryl, $C_{1-6}$ aliphatic-3-8 membered saturated or partially unsaturated carbocyclic ring, $C_{1-6}$ aliphatic-3-7 membered heterocyclic ring having 1-4 heteroatoms independently selected from nitrogen, oxygen, or sulfur, and a $C_{1-6}$ aliphatic-5-6 membered monocyclic heteroaryl ring having 1-4 heteroatoms independently selected from nitrogen, oxygen, or sulfur; each of which is optionally substituted;
Y is O, S, SO$_2$, SO, C(O), CO$_2$, C(O)N(R), —NRC(O), —NRC(O)N(R), —NRSO$_2$, or N(R); or Y is absent;
$R^1$ is $C_{1-6}$ aliphatic, $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or $R^1$ is CN.

In certain embodiments, X is N. In certain embodiments, X is $CR^2$.
In certain embodiments, $X^1$ is N. In certain embodiments, $X^1$ is $CR^2$.
In certain embodiments, $X^2$ is N. In certain embodiments, $X^2$ is $CR^2$.
In certain embodiments, each $R^2$ is independently H.
In certain embodiments, each $R^2$ is independently —R.

In certain embodiments, each $R^2$ is independently $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, each $R^2$ is independently phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, each $R^2$ is independently phenyl, furanyl, furazanyl, imidazolidinyl, imidazolinyl, imidazolyl, 1H-indazolyl, indolenyl, isoxazolyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, piperazinyl, piperidinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, 2H-pyrrolyl, pyrrolyl, tetrahydrofuranyl, thiazolyl, thienyl, thiophenyl, oxetanyl, or azetidinyl, each of which is optionally substituted.

In certain embodiments, each $R^2$ is independently phenyl or pyrazolyl, each of which is optionally substituted.

In certain embodiments, each $R^2$ is independently halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In certain embodiments, each $R^2$ is independently —OR, —SR, —SO$_2$R, —SOR, —NRC(O)R, —NRC(O)N(R)$_2$, —NRSO$_2$R, or —N(R)$_2$. In certain embodiments, each $R^2$ is independently —OR, —SR, —SO$_2$R, or —SOR. In certain embodiments, each $R^2$ is independently —NRC(O)R, —NRC(O)N(R)$_2$, —NRSO$_2$R, or —N(R)$_2$.

In certain embodiments, each $R^2$ is independently —OR, —SR, —SO$_2$R, —SOR, —NRC(O)R, —NRC(O)N(R)$_2$, —NRSO$_2$R, or —N(R)$_2$, and each R is independently hydrogen, $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, each $R^2$ is independently —OR or —N(R)$_2$, and each R is independently hydrogen or $C_{3-10}$ aryl, which is optionally substituted. In certain embodiments, each $R^2$ is independently —OR or —N(R)$_2$, and each R is independently hydrogen or a 3-8 membered saturated or partially unsaturated carbocyclic ring, which is optionally substituted. In certain embodiments, each $R^2$ is independently —OR or —N(R)$_2$, and each R is independently hydrogen or a 3-7 membered heterocyclic ring having 1-4 heteroatoms independently selected from nitrogen, oxygen, or sulfur, which is optionally substituted. In certain embodiments, each $R^2$ is independently —OR or —N(R)$_2$, and each R is independently hydrogen or a 5-6 membered monocyclic heteroaryl ring having 1-4 heteroatoms independently selected from nitrogen, oxygen, or sulfur, which is optionally substituted.

In certain embodiments, each $R^2$ is independently hydrogen,

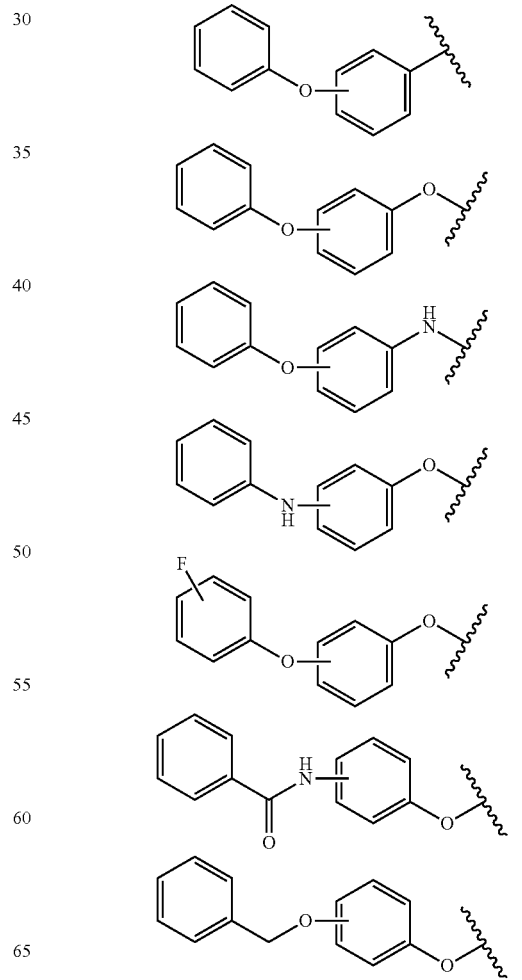

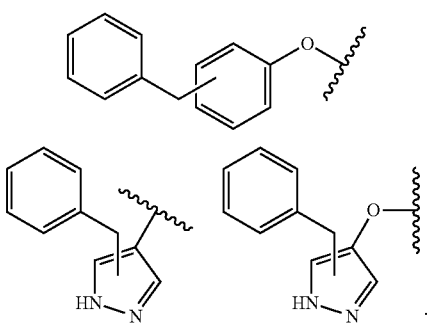

In certain embodiments, each R² is independently hydrogen,

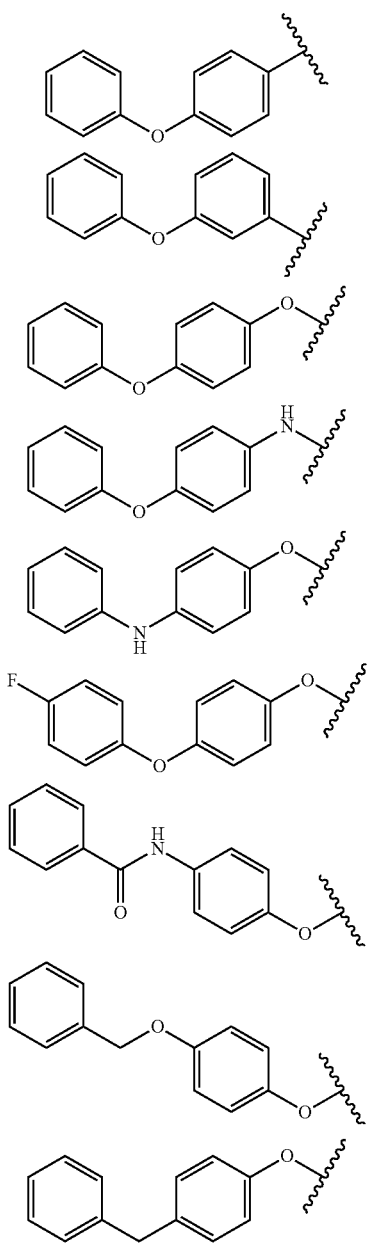

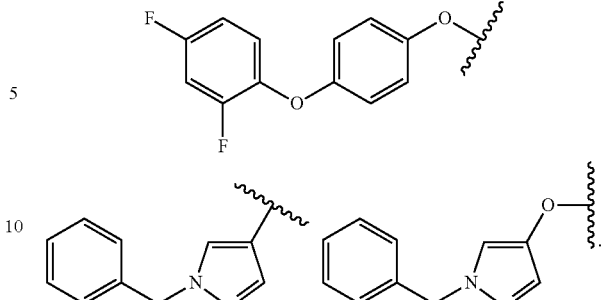

In certain embodiments, L is a divalent $C_{1-6}$ aliphatic which is optionally substituted. In certain embodiments, L is a divalent $C_{3-10}$ aryl which is optionally substituted. In certain embodiments, L is a divalent 3-8 membered saturated or partially unsaturated carbocyclic ring which is optionally substituted. In certain embodiments, L is a divalent 3-7 membered heterocyclic ring having 1-4 heteroatoms independently selected from nitrogen, oxygen, or sulfur, which is optionally substituted. In certain embodiments, L is a divalent 5-6 membered monocyclic heteroaryl ring having 1-4 heteroatoms independently selected from nitrogen, oxygen, or sulfur, which is optionally substituted.

In certain embodiments, L is a divalent $C_{1-6}$ aliphatic-$C_{3-10}$ aryl, which is optionally substituted. In certain embodiments, L is a divalent $C_{1-6}$ aliphatic-3-8 membered saturated or partially unsaturated carbocyclic ring, which is optionally substituted. In certain embodiments, L is a divalent $C_{1-6}$ aliphatic-3-7 membered heterocyclic ring having 1-4 heteroatoms independently selected from nitrogen, oxygen, or sulfur, which is optionally substituted. In certain embodiments, L is a divalent $C_{1-6}$ aliphatic-5-6 membered monocyclic heteroaryl ring having 1-4 heteroatoms independently selected from nitrogen, oxygen, or sulfur which is optionally substituted.

In certain embodiments, L is a divalent $C_{1-6}$ aliphatic selected from methylene, ethylene, propylene, i-propylene, butylene, s-butylene, t-butylene, straight or branched pentylene, or straight or branched hexylene; each of which is optionally substituted.

In certain embodiments, L is a divalent phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, L is

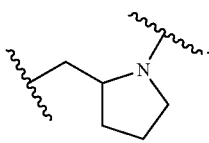

In certain embodiments, L is

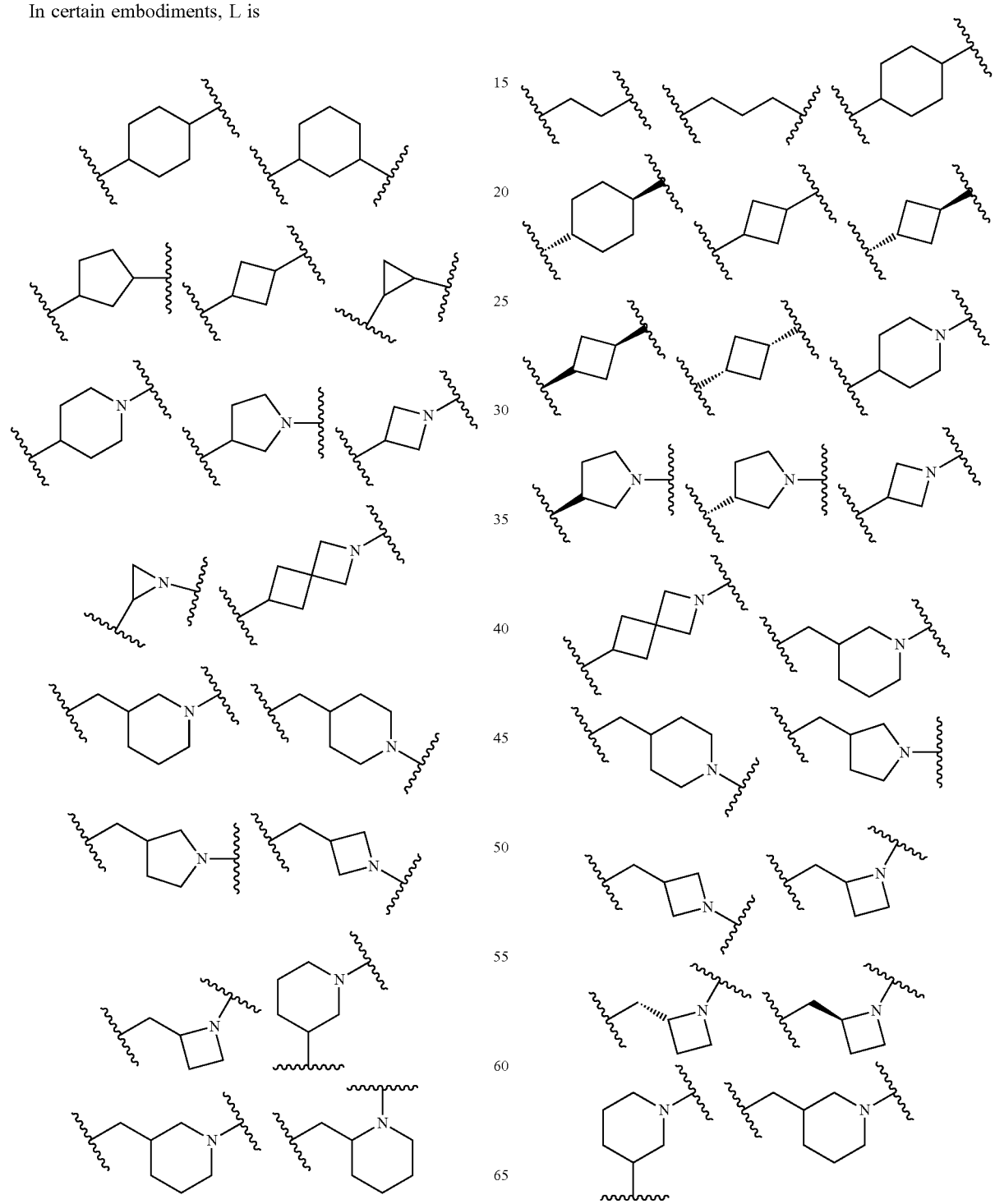

19
-continued

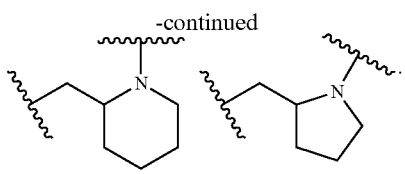

In certain embodiments, Y is —NRC(O), —NRC(O)N(R), —NRSO₂, or N(R).

In certain embodiments, Y is O, S, SO₂, SO, C(O), CO₂, or C(O)N(R).

In certain embodiments, Y is absent.

In certain embodiments, Y is N(R),

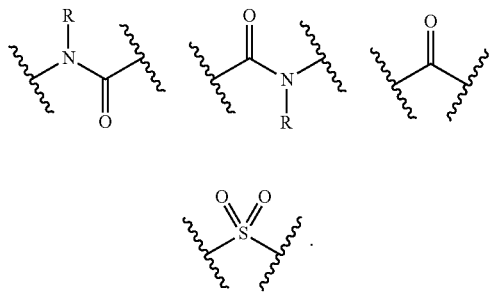

In certain embodiments, $R^1$ is an optionally substituted $C_{1-6}$ aliphatic. In certain embodiments, $R^1$ is an optionally substituted $C_{3-10}$ aryl. In certain embodiments, $R^1$ is an optionally substituted 3-8 membered saturated or partially unsaturated carbocyclic ring. In certain embodiments, $R^1$ is an optionally substituted 3-7 membered heterocylic ring having 1-4 heteroatoms independently selected from nitrogen, oxygen, or sulfur. In certain embodiments, $R^1$ is an optionally substituted 5-6 membered monocyclic heteroaryl ring having 1-4 heteroatoms independently selected from nitrogen, oxygen, or sulfur.

In certain embodiments, $R^1$ is $C_{1-6}$ aliphatic. In certain embodiments, $R^1$ is methyl, ethyl, propyl, i-propyl, butyl, s-butyl, t-butyl, straight or branched pentyl, or straight or branched hexyl; each of which is optionally substituted.

In certain embodiments, $R^1$ is $C_{2-6}$ alkenyl, which is optionally substituted. In certain embodiments, $R^1$ is $C_{2-6}$ alkynyl, which is optionally substituted.

In certain embodiments, $R^1$ is —CN, —CH₂CN,

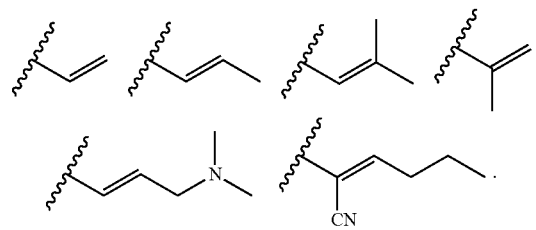

20

In certain embodiments, each of X, $X^1$, $X^2$, R, $R^1$, $R^2$, L, and Y is as defined above and described in embodiments, classes and subclasses above and herein, singly or in combination.

In certain embodiments, the present invention provides a compound of formula I-a,

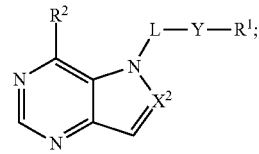

I-a or a pharmaceutically acceptable salt thereof, wherein each of $X^2$, $R^1$, $R^2$, L and Y is as defined above and described in embodiments, classes and subclasses above and herein, singly or in combination.

In certain embodiments, the present invention provides a compound of formula I-a1,

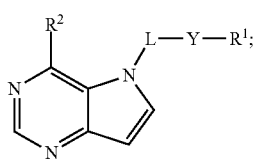

I-a1 or a pharmaceutically acceptable salt thereof, wherein each of $R^1$, $R^2$, L and Y is as defined above and described in embodiments, classes and subclasses above and herein, singly or in combination.

In certain embodiments, the present invention provides a compound of formula I-a2,

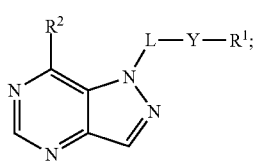

I-a2 or a pharmaceutically acceptable salt thereof, wherein each of $R^1$, $R^2$, L and Y is as defined above and described in embodiments, classes and subclasses above and herein, singly or in combination.

In certain embodiments, the present invention provides a compound of formula I-b,

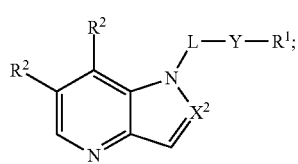

I-b or a pharmaceutically acceptable salt thereof, wherein each of $X^2$, $R^1$, $R^2$, L and Y is as defined above and described in embodiments, classes and subclasses above and herein, singly or in combination.

In certain embodiments, the present invention provides a compound of formula I-b1,

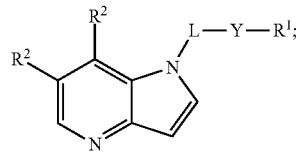

I-b1 or a pharmaceutically acceptable salt thereof, wherein each of $R^1$, $R^2$, L and Y is as defined above and described in embodiments, classes and subclasses above and herein, singly or in combination.

In certain embodiments, the present invention provides a compound of formula I-b2,

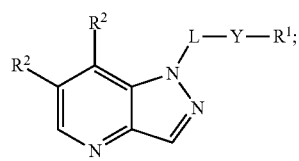

I-b2 or a pharmaceutically acceptable salt thereof, wherein each of $R^1$, $R^2$, L and Y is as defined above and described in embodiments, classes and subclasses above and herein, singly or in combination.

In certain embodiments, the compound is of formula I-c:

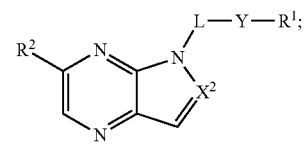

I-c or a pharmaceutically acceptable salt thereof, wherein each of $X^2$, $R^1$, $R^2$, L and Y is as defined above and described in embodiments, classes and subclasses above and herein, singly or in combination.

In certain embodiments, the compound is of formula I-c1:

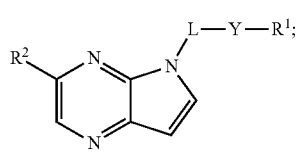

I-c1 or a pharmaceutically acceptable salt thereof, wherein each of $R^1$, $R^2$, L and Y is as defined above and described in embodiments, classes and subclasses above and herein, singly or in combination.

In certain embodiments, the compound is of formula I-c2:

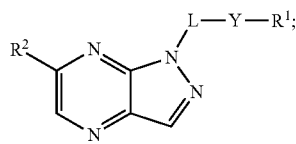

I-c2 or a pharmaceutically acceptable salt thereof, wherein each of $R^1$, $R^2$, L and Y is as defined above and described in embodiments, classes and subclasses above and herein, singly or in combination.

In certain embodiments, the invention provides a compound selected from Table 1:

TABLE 1

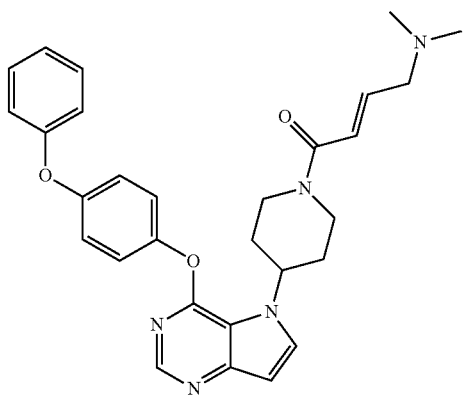 [SMILES: CN(C)C/C=C/C(=O)N1CCC(n2ccc3ncnc(Oc4ccc(Oc5ccccc5)cc4)c32)CC1]

1

TABLE 1-continued
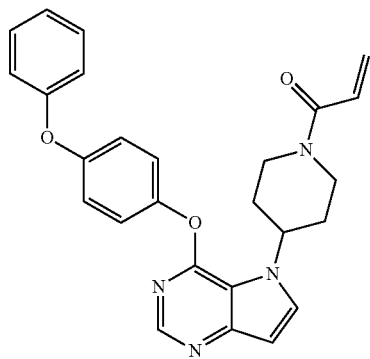 [SMILES: C=CC(=O)N1CCC(n2ccc3ncnc(Oc4ccc(Oc5ccccc5)cc4)c32)CC1]
2
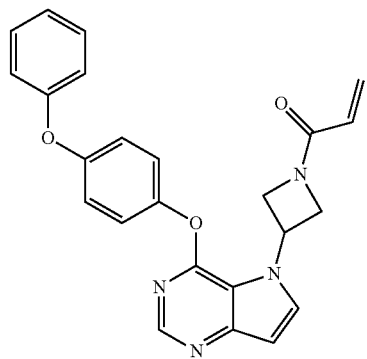 [SMILES: C=CC(=O)N1CC(n2ccc3ncnc(Oc4ccc(Oc5ccccc5)cc4)c32)C1]
3
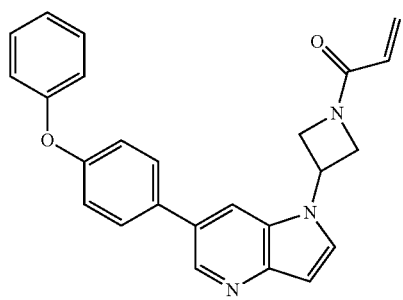 [SMILES: C=CC(=O)N1CC(n2ccc3ncc(-c4ccc(Oc5ccccc5)cc4)cc32)C1]
4
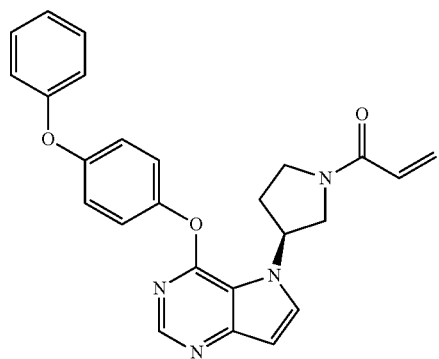 [SMILES: C=CC(=O)N1CC[C@H](n2ccc3ncnc(Oc4ccc(Oc5ccccc5)cc4)c32)C1]
5

TABLE 1-continued
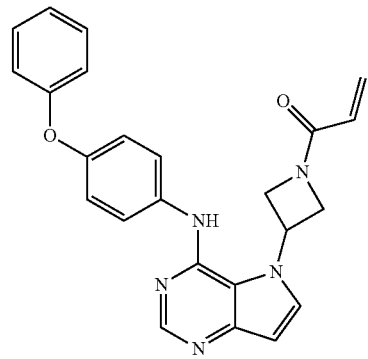 [SMILES: C=CC(=O)N1CC(n2ccc3ncnc(Nc4ccc(Oc5ccccc5)cc4)c32)C1]
6
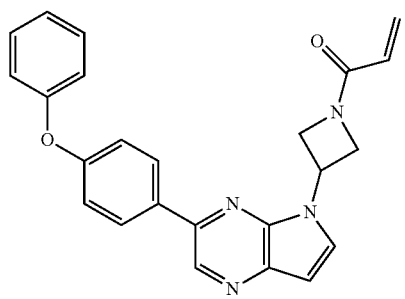 [SMILES: C=CC(=O)N1CC(n2ccc3ncc(-c4ccc(Oc5ccccc5)cc4)nc32)C1]
7
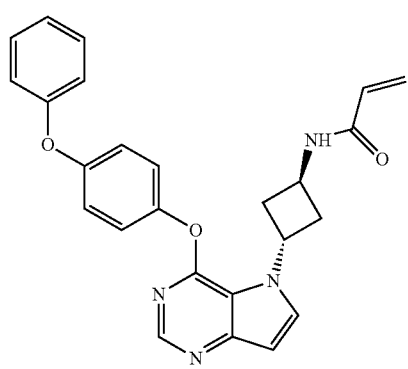 [SMILES: C=CC(=O)N[C@H]1C[C@H](n2ccc3ncnc(Oc4ccc(Oc5ccccc5)cc4)c32)C1]
8
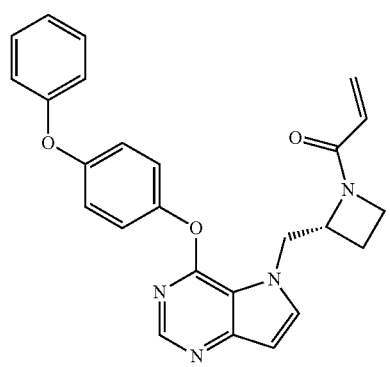 [SMILES: C=CC(=O)N1CC[C@@H]1Cn1ccc2ncnc(Oc3ccc(Oc4ccccc4)cc3)c21]
9

TABLE 1-continued
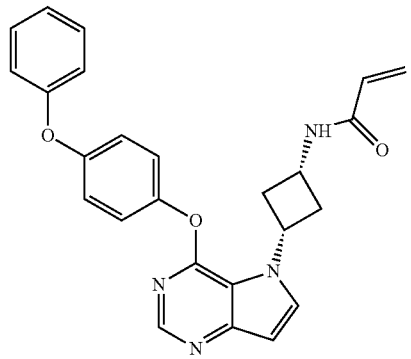 [SMILES: C=CC(=O)N[C@H]1C[C@@H](n2ccc3ncnc(Oc4ccc(Oc5ccccc5)cc4)c32)C1]
10
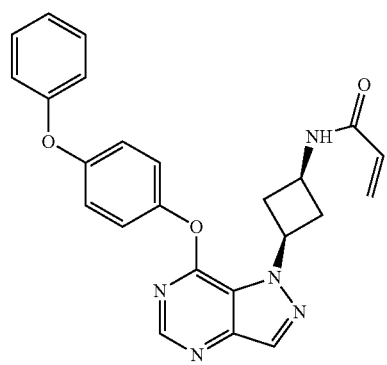 [SMILES: C=CC(=O)N[C@H]1C[C@@H](n2ncc3ncnc(Oc4ccc(Oc5ccccc5)cc4)c32)C1]
11
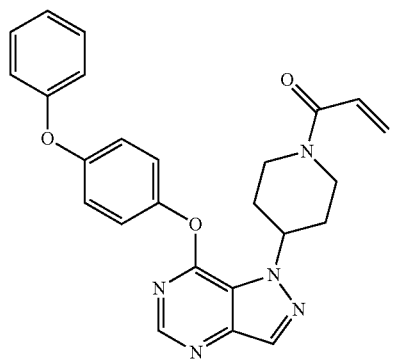 [SMILES: C=CC(=O)N1CCC(n2ncc3ncnc(Oc4ccc(Oc5ccccc5)cc4)c32)CC1]
12
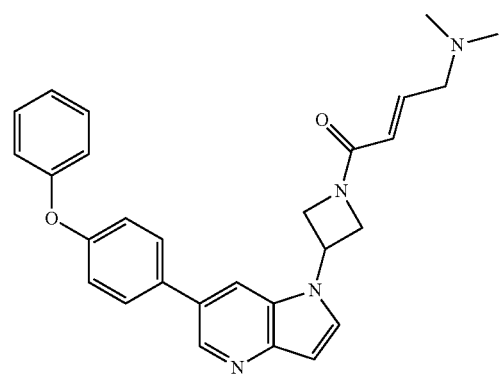 [SMILES: CN(C)C/C=C/C(=O)N1CC(n2ccc3ncc(-c4ccc(Oc5ccccc5)cc4)cc32)C1]
13

TABLE 1-continued
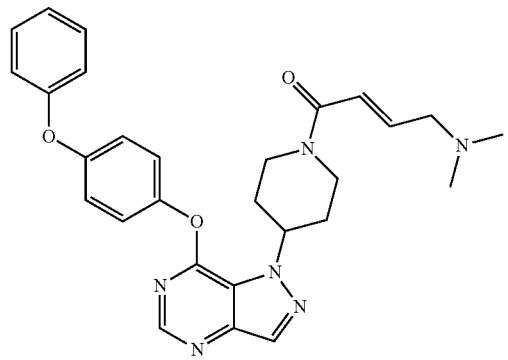 [SMILES: CN(C)C/C=C/C(=O)N1CCC(n2ncc3ncnc(Oc4ccc(Oc5ccccc5)cc4)c32)CC1]
14
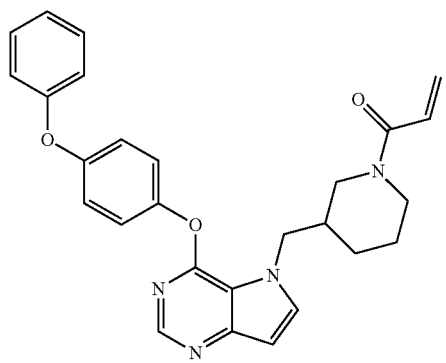 [SMILES: C=CC(=O)N1CCCC(Cn2ccc3ncnc(Oc4ccc(Oc5ccccc5)cc4)c32)C1]
15
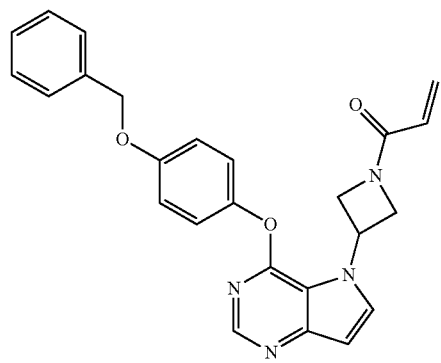 [SMILES: C=CC(=O)N1CC(n2ccc3ncnc(Oc4ccc(OCc5ccccc5)cc4)c32)C1]
16
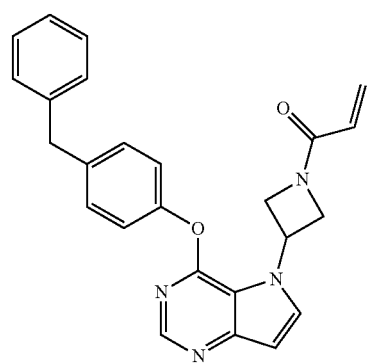
17

TABLE 1-continued
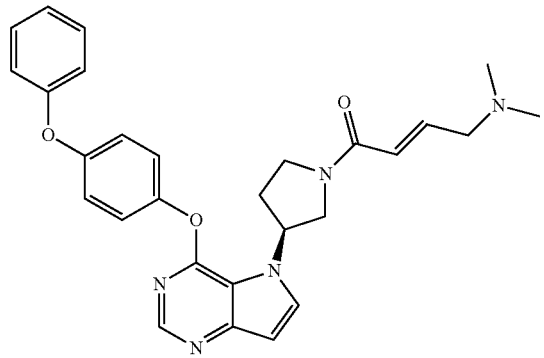 [SMILES: CN(C)C/C=C/C(=O)N1CC[C@H](n2ccc3ncnc(Oc4ccc(Oc5ccccc5)cc4)c32)C1]
18
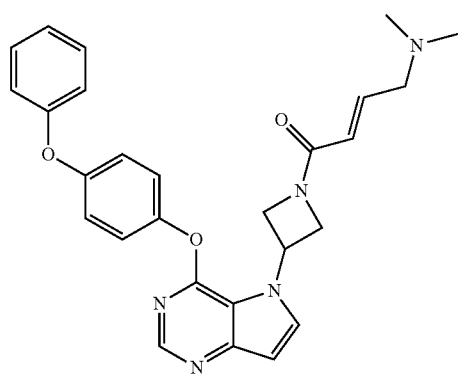 [SMILES: CN(C)C/C=C/C(=O)N1CC(n2ccc3ncnc(Oc4ccc(Oc5ccccc5)cc4)c32)C1]
19
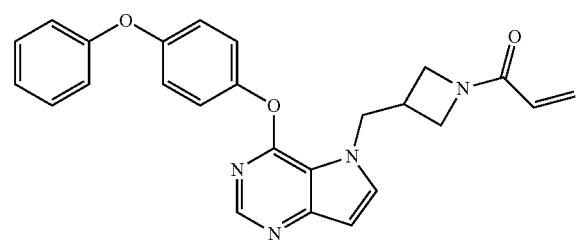 [SMILES: C=CC(=O)N1CC(Cn2ccc3ncnc(Oc4ccc(Oc5ccccc5)cc4)c32)C1]
20
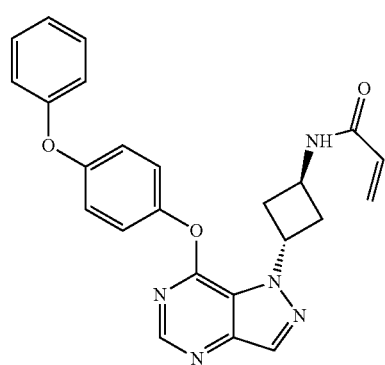 [SMILES: C=CC(=O)N[C@H]1C[C@H](n2ncc3ncnc(Oc4ccc(Oc5ccccc5)cc4)c32)C1]
21

TABLE 1-continued
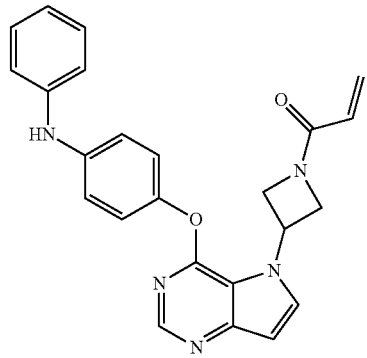 [SMILES: C=CC(=O)N1CC(n2ccc3ncnc(Oc4ccc(Nc5ccccc5)cc4)c32)C1]
22
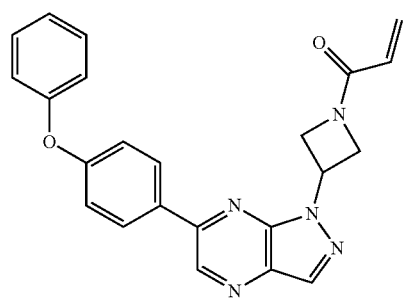 [SMILES: C=CC(=O)N1CC(n2ncc3ncc(-c4ccc(Oc5ccccc5)cc4)nc32)C1]
23
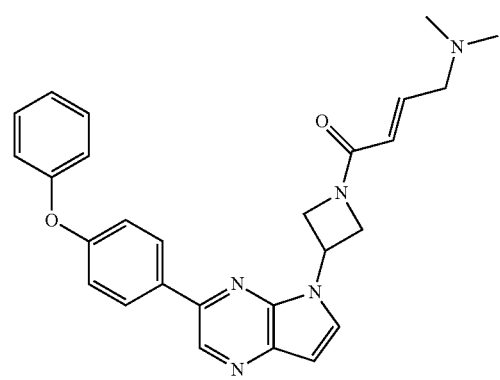 [SMILES: CN(C)C/C=C/C(=O)N1CC(n2ccc3ncc(-c4ccc(Oc5ccccc5)cc4)nc32)C1]
24
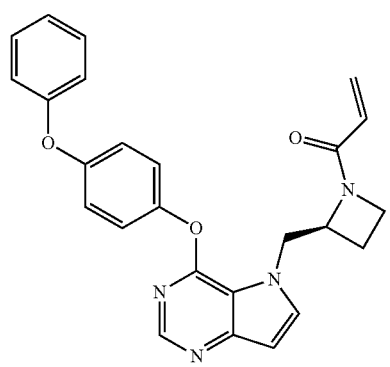 [SMILES: C=CC(=O)N1CC[C@H]1Cn1ccc2ncnc(Oc3ccc(Oc4ccccc4)cc3)c21]
25

TABLE 1-continued
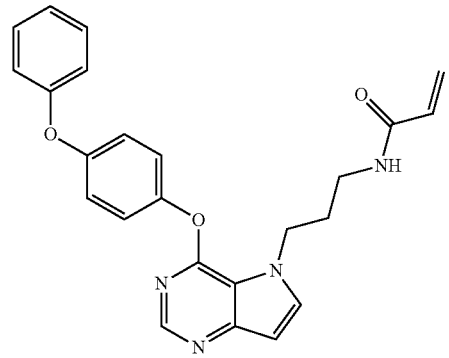 [SMILES: C=CC(=O)NCCCn1ccc2ncnc(Oc3ccc(Oc4ccccc4)cc3)c21]
26
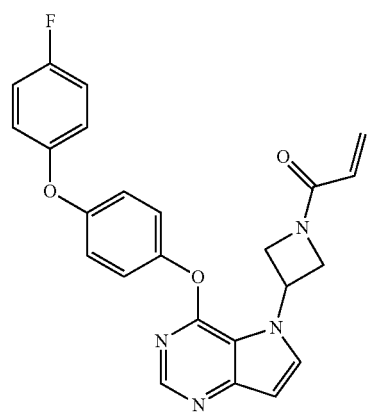 [SMILES: C=CC(=O)N1CC(n2ccc3ncnc(Oc4ccc(Oc5ccc(F)cc5)cc4)c32)C1]
27
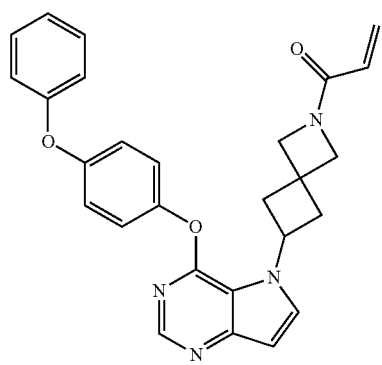 [SMILES: C=CC(=O)N1CC2(CC(n3ccc4ncnc(Oc5ccc(Oc6ccccc6)cc5)c43)C2)C1]
28
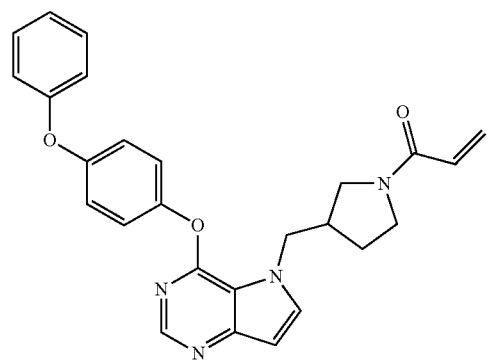 [SMILES: C=CC(=O)N1CCC(Cn2ccc3ncnc(Oc4ccc(Oc5ccccc5)cc4)c32)C1]
29

TABLE 1-continued
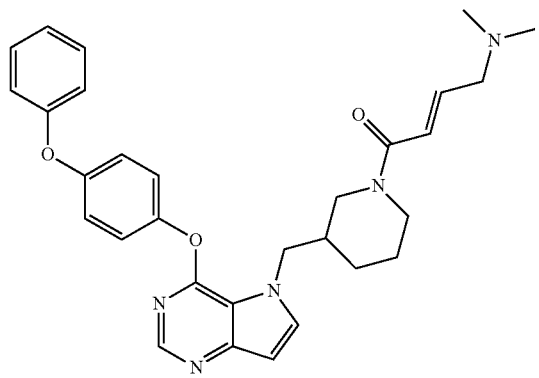 [SMILES: CN(C)C/C=C/C(=O)N1CCCC(Cn2ccc3ncnc(Oc4ccc(Oc5ccccc5)cc4)c32)C1]
30
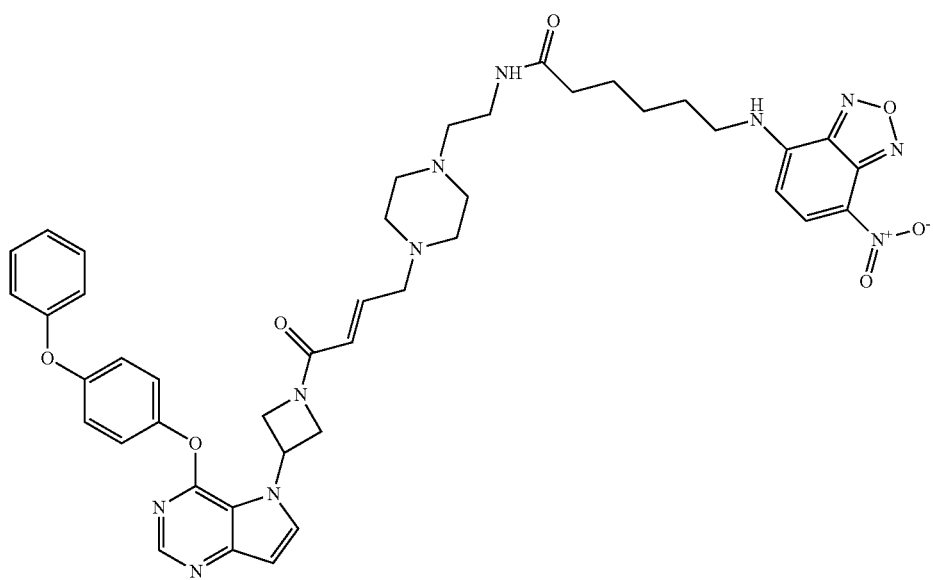 [SMILES: O=C(CCCCCNc1ccc([N+](=O)[O-])c2nonc12)NCCN1CCN(C/C=C/C(=O)N2CC(n3ccc4ncnc(Oc5ccc(Oc6ccccc6)cc5)c43)C2)CC1]
31
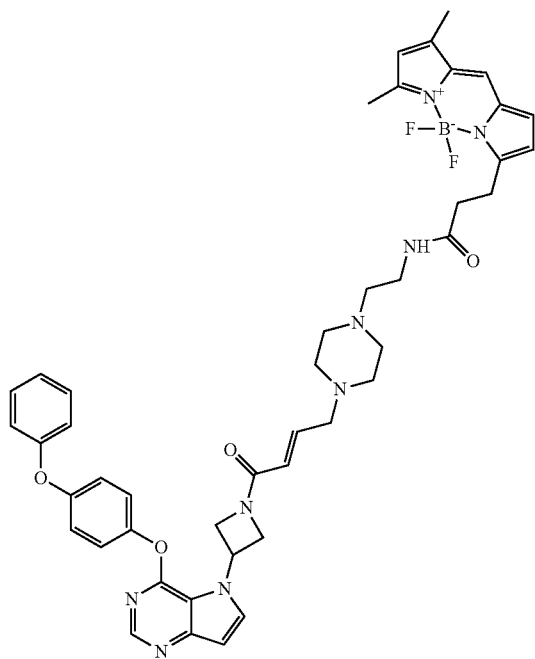 [SMILES: CC1=CC(C)=[N+]2C1=Cc1ccc(CCC(=O)NCCN3CCN(C/C=C/C(=O)N4CC(n5ccc6ncnc(Oc7ccc(Oc8ccccc8)cc7)c65)C4)CC3)n1[B-]2(F)F]
32

TABLE 1-continued
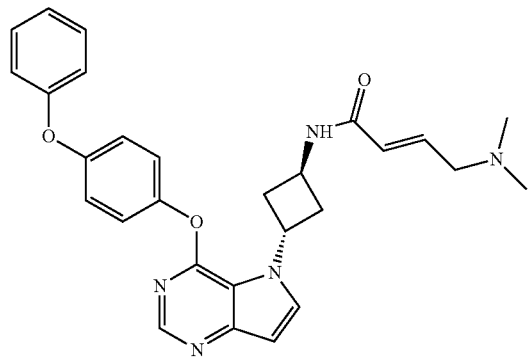
33
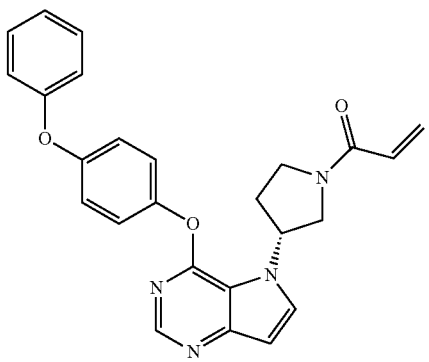 [SMILES: C=CC(=O)N1CC[C@@H](n2ccc3ncnc(Oc4ccc(Oc5ccccc5)cc4)c32)C1]
34
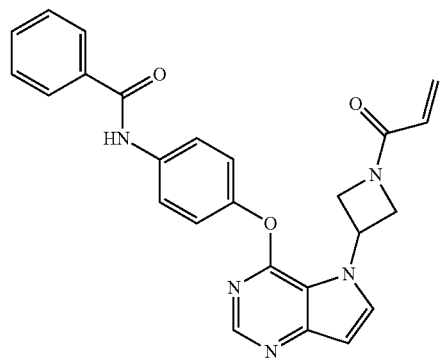 [SMILES: C=CC(=O)N1CC(n2ccc3ncnc(Oc4ccc(NC(=O)c5ccccc5)cc4)c32)C1]
35
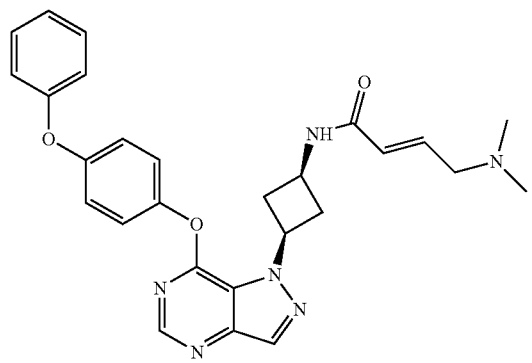 [SMILES: CN(C)C/C=C/C(=O)N[C@H]1C[C@@H](n2ncc3ncnc(Oc4ccc(Oc5ccccc5)cc4)c32)C1]
36

TABLE 1-continued
| | |
|---|---|
| 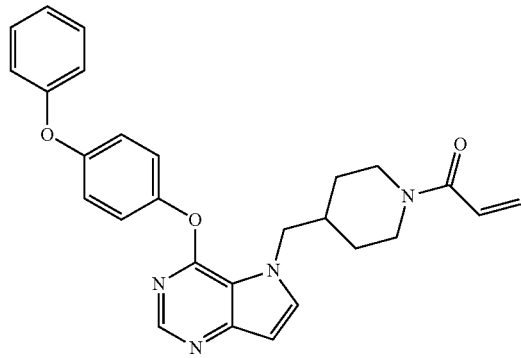 [SMILES: C=CC(=O)N1CCC(Cn2ccc3ncnc(Oc4ccc(Oc5ccccc5)cc4)c32)CC1] | 37 |
| 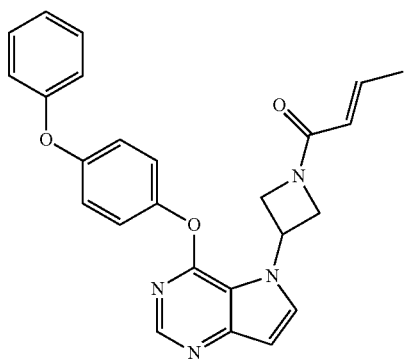 [SMILES: C/C=C/C(=O)N1CC(n2ccc3ncnc(Oc4ccc(Oc5ccccc5)cc4)c32)C1] | 38 |
| 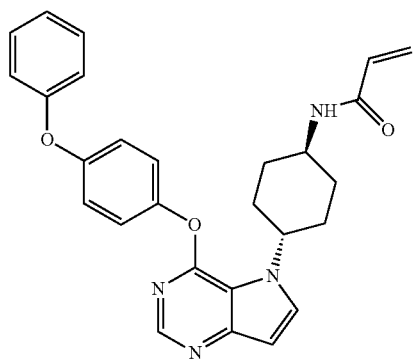 [SMILES: C=CC(=O)N[C@H]1CC[C@H](n2ccc3ncnc(Oc4ccc(Oc5ccccc5)cc4)c32)CC1] | 39 |
| 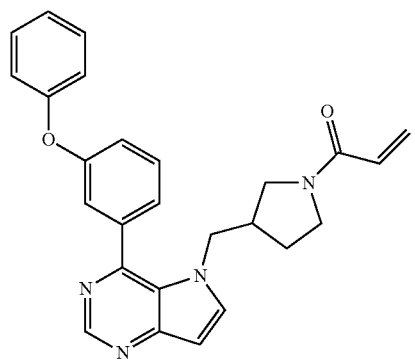 [SMILES: C=CC(=O)N1CCC(Cn2ccc3ncnc(-c4cccc(Oc5ccccc5)c4)c32)C1] | 40 |

US 9,738,648 B2
TABLE 1-continued
| | |
|---|---|
| 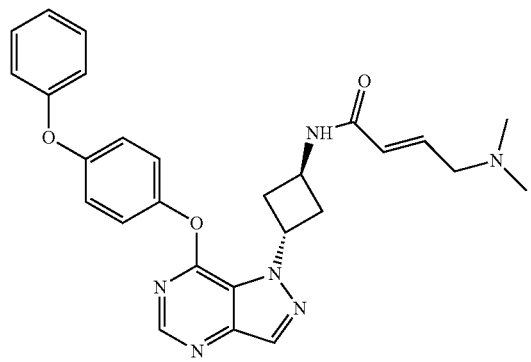 [SMILES: CN(C)C/C=C/C(=O)N[C@H]1C[C@H](n2ncc3ncnc(Oc4ccc(Oc5ccccc5)cc4)c32)C1] | 41 |
| 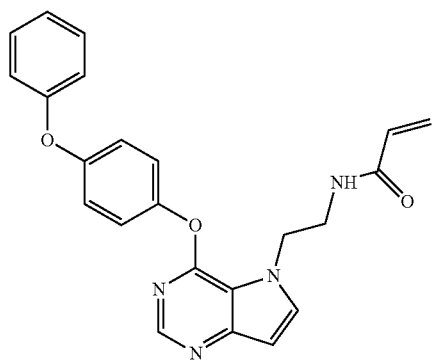 [SMILES: C=CC(=O)NCCn1ccc2ncnc(Oc3ccc(Oc4ccccc4)cc3)c21] | 42 |
| 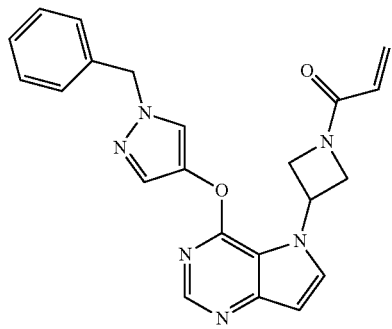 [SMILES: C=CC(=O)N1CC(n2ccc3ncnc(Oc4cnn(Cc5ccccc5)c4)c32)C1] | 43 |
| 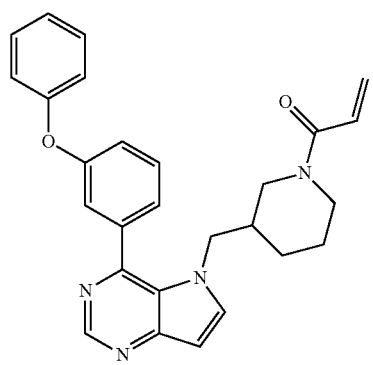 [SMILES: C=CC(=O)N1CCCC(Cn2ccc3ncnc(-c4cccc(Oc5ccccc5)c4)c32)C1] | 44 |

TABLE 1-continued
| | |
|---|---|
| 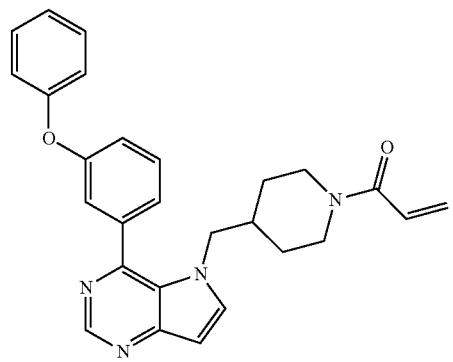 [SMILES: C=CC(=O)N1CCC(Cn2ccc3ncnc(-c4cccc(Oc5ccccc5)c4)c32)CC1] | 45 |
| 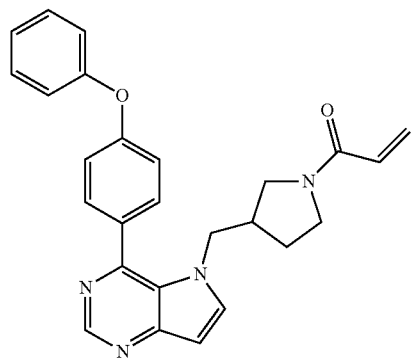 [SMILES: C=CC(=O)N1CCC(Cn2ccc3ncnc(-c4ccc(Oc5ccccc5)cc4)c32)C1] | 46 |
| 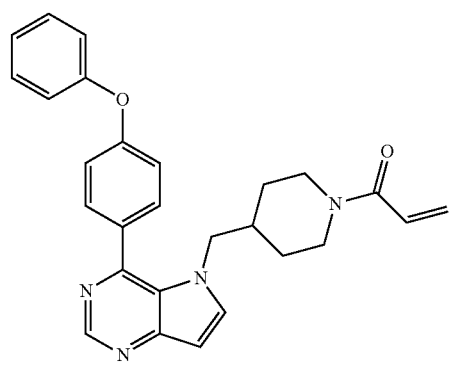 [SMILES: C=CC(=O)N1CCC(Cn2ccc3ncnc(-c4ccc(Oc5ccccc5)cc4)c32)CC1] | 47 |
| 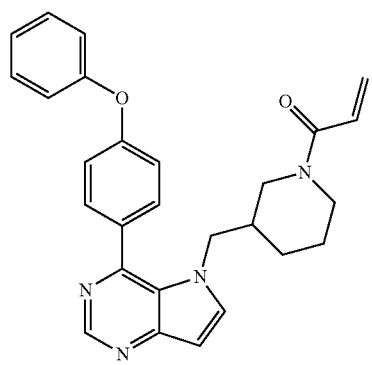 [SMILES: C=CC(=O)N1CCCC(Cn2ccc3ncnc(-c4ccc(Oc5ccccc5)cc4)c32)C1] | 48 |

TABLE 1-continued
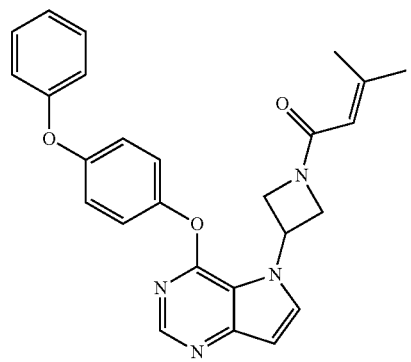 [SMILES: CC(C)=CC(=O)N1CC(n2ccc3ncnc(Oc4ccc(Oc5ccccc5)cc4)c32)C1]
49
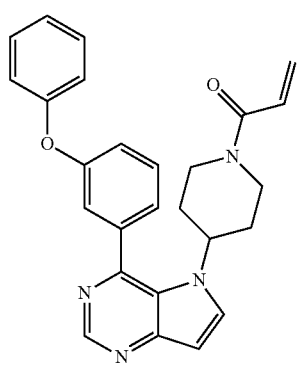 [SMILES: C=CC(=O)N1CCC(n2ccc3ncnc(-c4cccc(Oc5ccccc5)c4)c32)CC1]
50
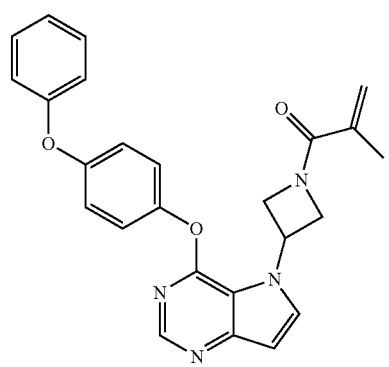 [SMILES: C=C(C)C(=O)N1CC(n2ccc3ncnc(Oc4ccc(Oc5ccccc5)cc4)c32)C1]
51
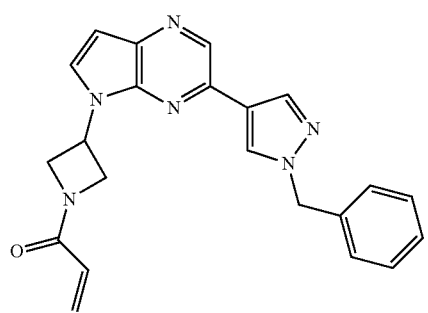 [SMILES: C=CC(=O)N1CC(n2ccc3ncc(-c4cnn(Cc5ccccc5)c4)nc32)C1]
52

TABLE 1-continued
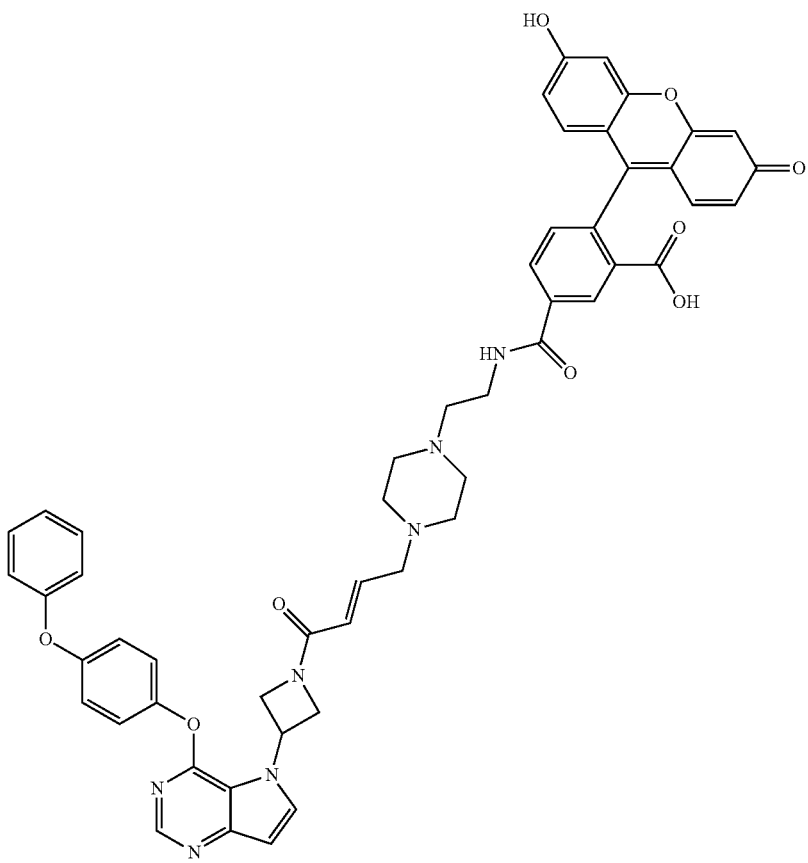 [SMILES: O=C(NCCN1CCN(C/C=C/C(=O)N2CC(n3ccc4ncnc(Oc5ccc(Oc6ccccc6)cc5)c43)C2)CC1)c1ccc(-c2c3ccc(=O)cc-3oc3cc(O)ccc23)c(C(=O)O)c1]
53
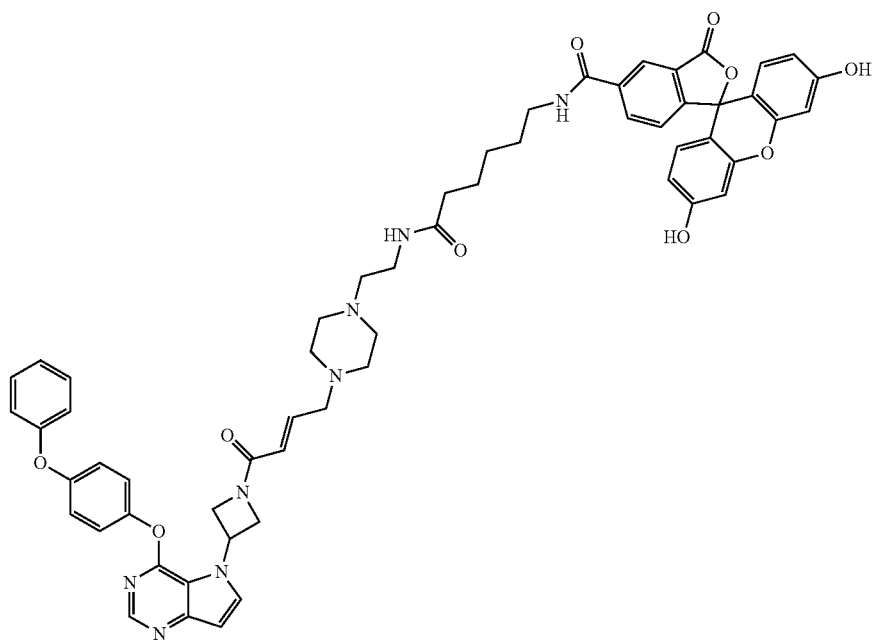 [SMILES: O=C(CCCCCNC(=O)c1ccc2c(c1)C(=O)OC21c2ccc(O)cc2Oc2cc(O)ccc21)NCCN1CCN(C/C=C/C(=O)N2CC(n3ccc4ncnc(Oc5ccc(Oc6ccccc6)cc5)c43)C2)CC1]
54

TABLE 1-continued
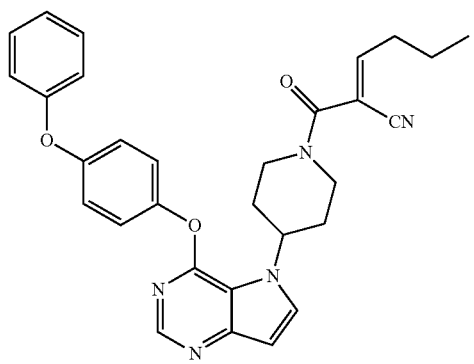 [SMILES: CCC/C=C(\C#N)C(=O)N1CCC(n2ccc3ncnc(Oc4ccc(Oc5ccccc5)cc4)c32)CC1]
55
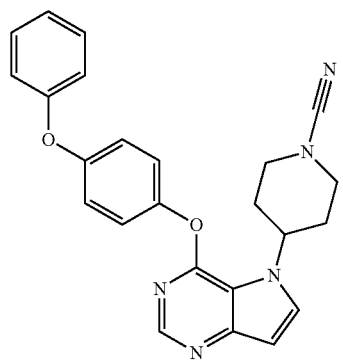 [SMILES: N#CN1CCC(n2ccc3ncnc(Oc4ccc(Oc5ccccc5)cc4)c32)CC1]
56
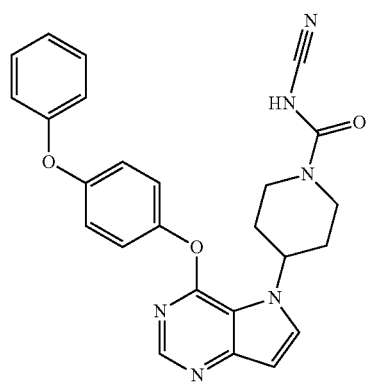 [SMILES: N#CNC(=O)N1CCC(n2ccc3ncnc(Oc4ccc(Oc5ccccc5)cc4)c32)CC1]
57
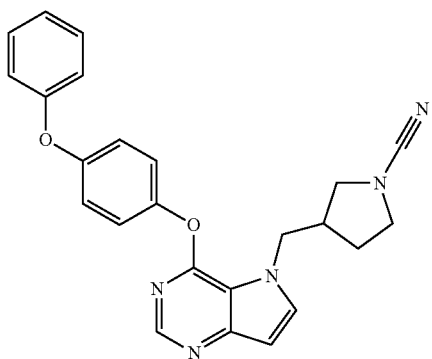 [SMILES: N#CN1CCC(Cn2ccc3ncnc(Oc4ccc(Oc5ccccc5)cc4)c32)C1]
58

TABLE 1-continued
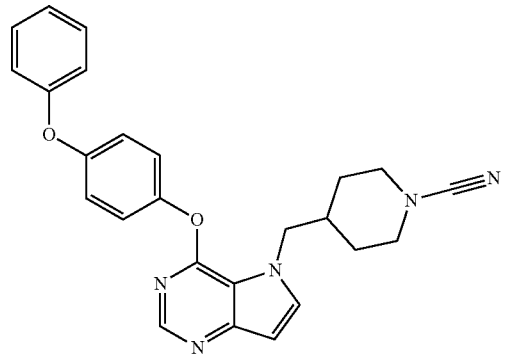 [SMILES: N#CN1CCC(Cn2ccc3ncnc(Oc4ccc(Oc5ccccc5)cc4)c32)CC1]
59
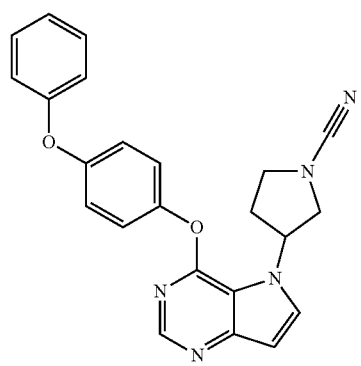 [SMILES: N#CN1CCC(n2ccc3ncnc(Oc4ccc(Oc5ccccc5)cc4)c32)C1]
60
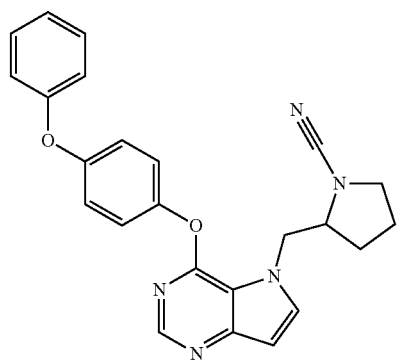 [SMILES: N#CN1CCCC1Cn1ccc2ncnc(Oc3ccc(Oc4ccccc4)cc3)c21]
61
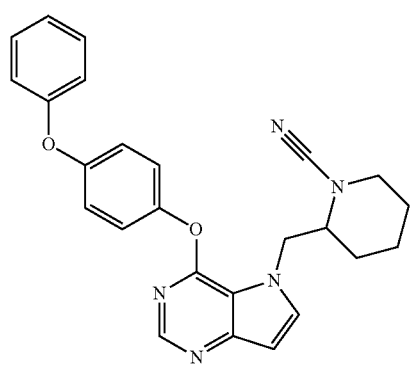 [SMILES: N#CN1CCCCC1Cn1ccc2ncnc(Oc3ccc(Oc4ccccc4)cc3)c21]
62

TABLE 1-continued
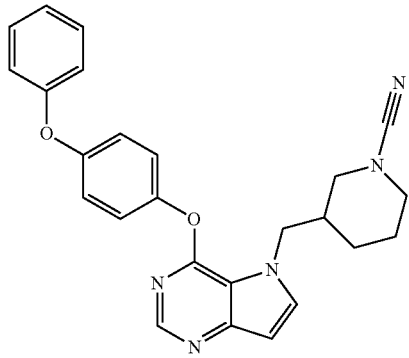 [SMILES: N#CN1CCCC(Cn2ccc3ncnc(Oc4ccc(Oc5ccccc5)cc4)c32)C1]
63
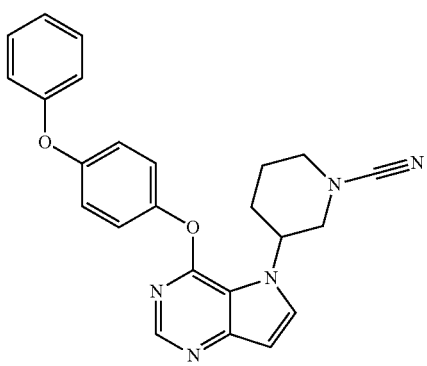 [SMILES: N#CN1CCCC(n2ccc3ncnc(Oc4ccc(Oc5ccccc5)cc4)c32)C1]
64
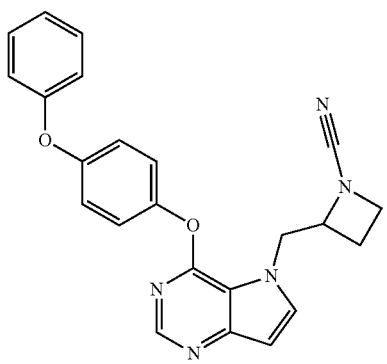 [SMILES: N#CN1CCC1Cn1ccc2ncnc(Oc3ccc(Oc4ccccc4)cc3)c21]
65
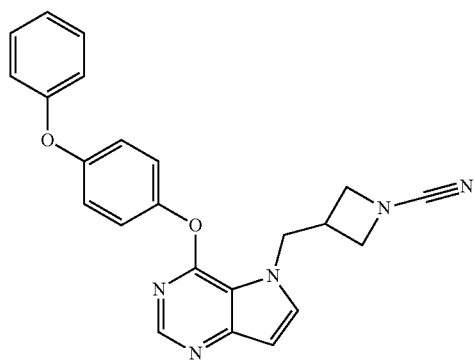 [SMILES: N#CN1CC(Cn2ccc3ncnc(Oc4ccc(Oc5ccccc5)cc4)c32)C1]
66

TABLE 1-continued
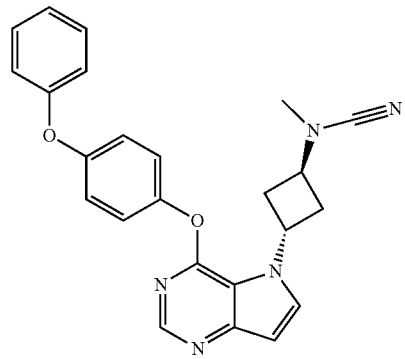 [SMILES: CN(C#N)[C@H]1C[C@H](n2ccc3ncnc(Oc4ccc(Oc5ccccc5)cc4)c32)C1]
67
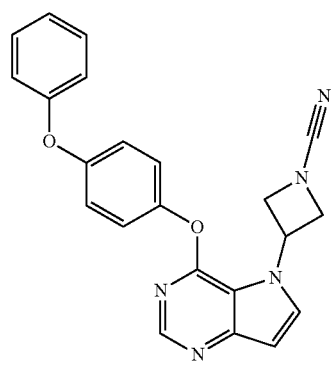 [SMILES: N#CN1CC(n2ccc3ncnc(Oc4ccc(Oc5ccccc5)cc4)c32)C1]
68
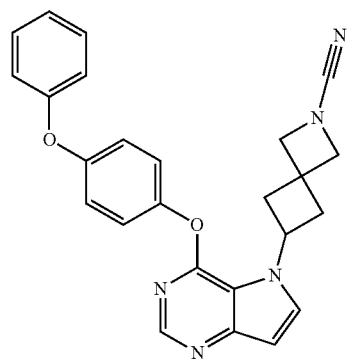 [SMILES: N#CN1CC2(CC(n3ccc4ncnc(Oc5ccc(Oc6ccccc6)cc5)c43)C2)C1]
69
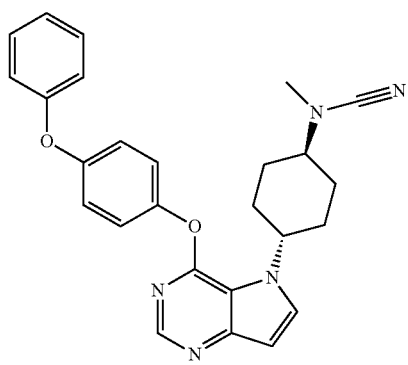 [SMILES: CN(C#N)[C@H]1CC[C@H](n2ccc3ncnc(Oc4ccc(Oc5ccccc5)cc4)c32)CC1]
70

TABLE 1-continued
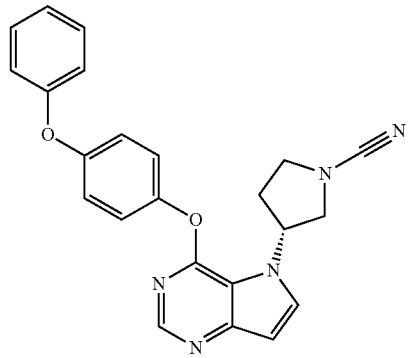 [SMILES: N#CN1CC[C@@H](n2ccc3ncnc(Oc4ccc(Oc5ccccc5)cc4)c32)C1]
71
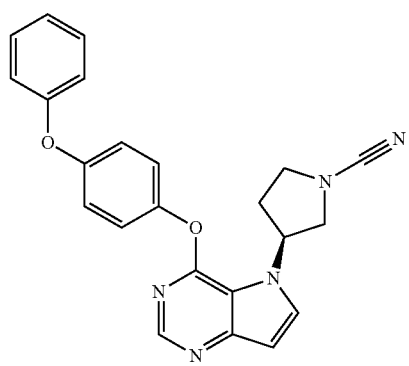 [SMILES: N#CN1CC[C@H](n2ccc3ncnc(Oc4ccc(Oc5ccccc5)cc4)c32)C1]
72
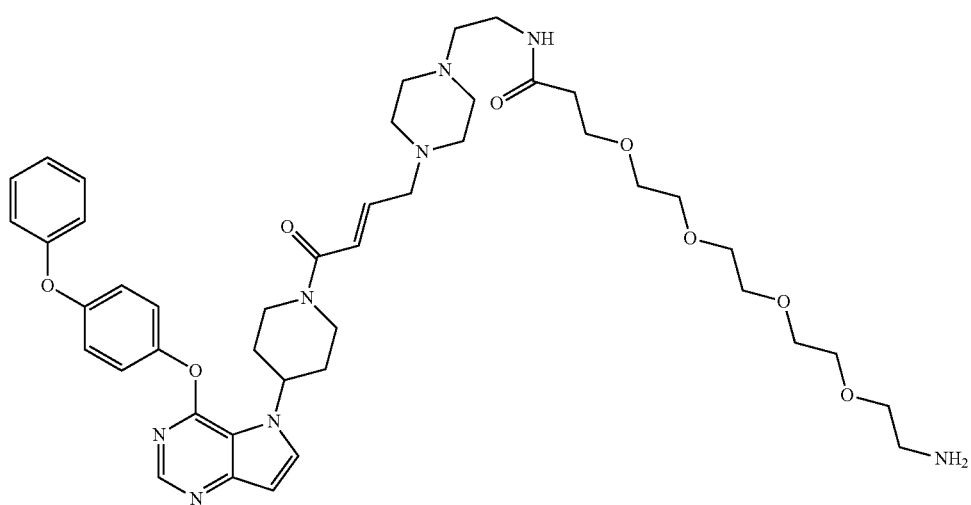 [SMILES: NCCOCCOCCOCCOCCC(=O)NCCN1CCN(C/C=C/C(=O)N2CCC(n3ccc4ncnc(Oc5ccc(Oc6ccccc6)cc5)c43)CC2)CC1]
73

TABLE 1-continued
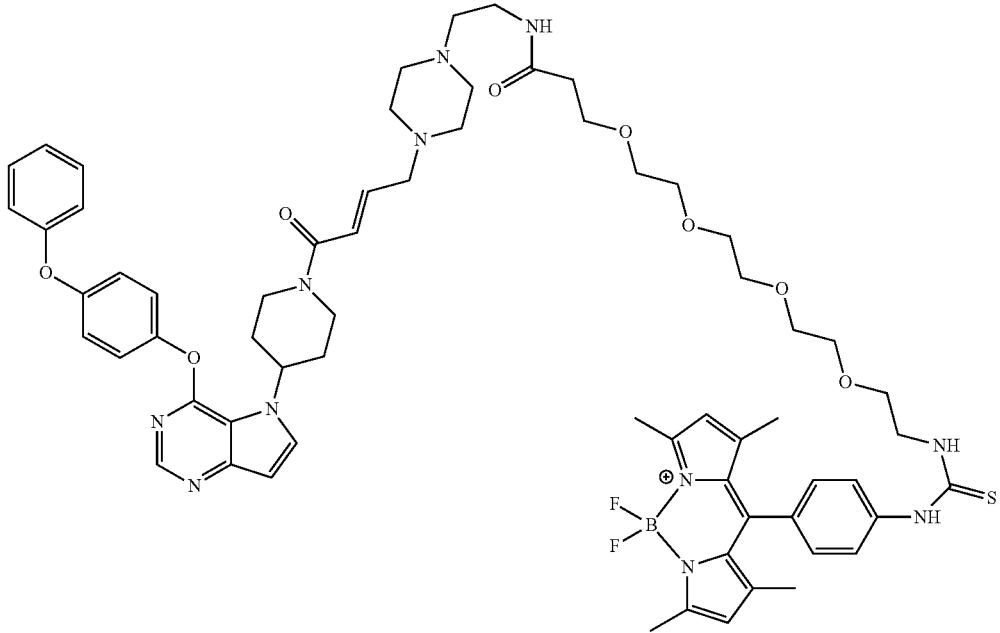
74
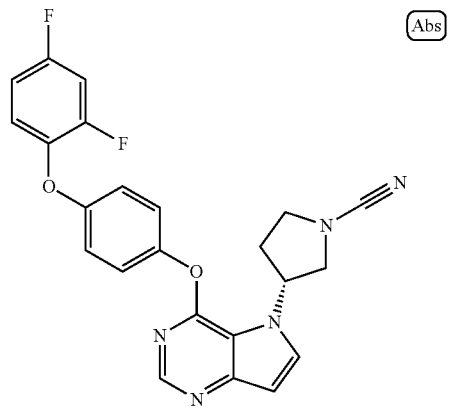 [SMILES: N#CN1CC[C@@H](n2ccc3ncnc(Oc4ccc(Oc5ccc(F)cc5F)cc4)c32)C1]
75
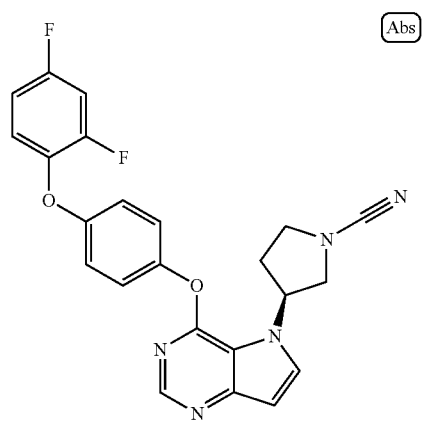 [SMILES: N#CN1CC[C@H](n2ccc3ncnc(Oc4ccc(Oc5ccc(F)cc5F)cc4)c32)C1]
76

TABLE 1-continued

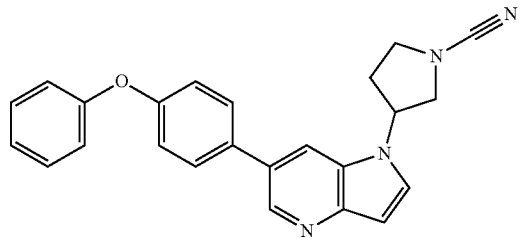 [SMILES: N#CN1CCC(n2ccc3ncc(-c4ccc(Oc5ccccc5)cc4)cc32)C1]

77

As defined generally above, the group "L-R$^1$" is a warhead group. Without wishing to be bound by any particular theory, it is believed that such warhead groups are particularly suitable for covalently binding to a key cysteine residue in the binding domain of certain protein kinases. Protein kinases having a cysteine residue in the binding domain are known to one of ordinary skill in the art and include BTK, or a mutant thereof. Thus, in some embodiments, L-R$^1$ is characterized in that the L-R$^1$ moiety is capable of covalently binding to a cysteine residue thereby irreversibly inhibiting the enzyme. In certain embodiments, the cysteine residue in the kinase domain in the ATP biding site. In certain embodiments, the cysteine residue is Cysteine-481.

In some embodiments, the present invention provides a compound selected from those depicted above, or a pharmaceutically acceptable salt thereof.

Various structural depictions may show a heteroatom without an attached group, radical, charge, or counterion. Those of ordinary skill in the art are aware that such depictions are meant to indicate that the heteroatom is attached to hydrogen (e.g.,

is understood to be

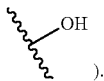

).

In certain embodiments, the compounds of the invention were synthesized in accordance with Scheme A below. More specific examples of compounds made utilizing Scheme A are provided in the Examples below.

Scheme A

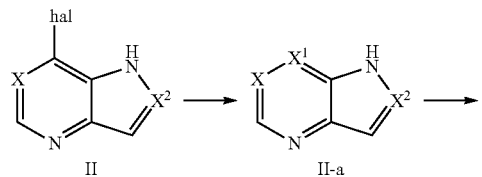

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit BTK, or a mutant thereof, in a biological sample or in a patient. In certain embodiments, the amount of compound in compositions of this invention is such that is effective to measurably inhibit BTK, or a mutant thereof, in a biological sample or in a patient. In certain embodiments, a composition of this invention is formulated for administration to a patient in need of such composition.

The term "patient" or "subject", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that are used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention are administered orally, parenterally, by inhalation spray, topically, rectally, nasally, buccally, vaginally or via an implanted reservoir.

The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention include aqueous or oleaginous suspension. These suspensions are formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that are employed are water, Ringer's solution and isotonic sodium chloride solution. In addition, sterile, fixed oils are conventionally employed as a solvent or suspending medium.

For this purpose, any bland fixed oil employed includes synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms are also be used for the purposes of formulation.

Pharmaceutically acceptable compositions of this invention are orally administered in any orally acceptable dosage form. Exemplary oral dosage forms are capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents are optionally also added.

Alternatively, pharmaceutically acceptable compositions of this invention are administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention are also administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches are also used.

For topical applications, provided pharmaceutically acceptable compositions are formulated in a suitable ointment containing the active component suspended or dissolved in one or more carriers. Exemplary carriers for topical administration of compounds of this are mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Pharmaceutically acceptable compositions of this invention are optionally administered by nasal aerosol or inhalation. Such compositions are prepared according to techniques well-known in the art of pharmaceutical formulation and are prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that are optionally combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

In certain embodiments, the invention provides a method for inhibiting BTK, or a mutant thereof, in a patient or in a biological sample comprising the step of administering to said patient or contacting said biological sample with a compound according to the invention.

In certain embodiments, the invention is directed to the use of compounds of the invention and/or physiologically acceptable salts thereof, for modulating or inhibiting a BTK enzyme. The term "modulation" denotes any change in BTK-mediated signal transduction, which is based on the action of the specific inventive compounds capable to interact with the BTK target in such a manner that makes recognition, binding and activating possible. The compounds are characterized by such a high affinity to BTK, which ensures a reliable binding of BTK. In certain embodiments, the substances are highly selective for BTK over most other kinases in order to guarantee an exclusive and directed recognition with the single BTK target. In the context of the present invention, the term "recognition"—without being limited thereto—relates to any type of interaction between the specific compounds and the target, particularly covalent or non-covalent binding or association, such as a covalent bond, hydrophobic/hydrophilic interactions, van der Waals forces, ion pairs, hydrogen bonds, ligand-receptor (enzyme-inhibitor) interactions, and the like. Such association may also encompass the presence of other molecules such as peptides, proteins or nucleotide sequences. The present protein/ligand (enzyme-inhibitor)-interaction is characterized by high affinity, high selectivity and minimal or even lacking cross-reactivity to other target molecules to exclude unhealthy and harmful impacts to the treated subject.

In certain embodiments, the present invention relates to a method for inhibiting a BTK enzyme, with at least one compound of formula (I) according to the invention and/or physiologically acceptable salts thereof, under conditions such that said BTK enzyme is inhibited. In certain embodiments, the system is a cellular system. In other embodiments, the system is an in-vitro translation which is based on the protein synthesis without living cells. The cellular system is defined to be any subject provided that the subject comprises cells. Hence, the cellular system can be selected from the group of single cells, cell cultures, tissues, organs and animals. In certain embodiments, the method for modulating a BTK enzyme is performed in-vitro. The prior teaching of the present specification concerning the compounds of formula (I), including any embodiments thereof, is valid and applicable without restrictions to the compounds according to formula (I) and their salts when used in the method for inhibiting BTK. The prior teaching of the present specification concerning the compounds of formula (I), including any embodiments thereof, is valid and applicable without restrictions to the compounds according to formula (I) and their salts when used in the method for inhibiting BTK.

Patients with mutations in BTK have a profound block in B cell development, resulting in the almost complete absence of mature B lymphocytes and plasma cells, severely reduced Ig levels and a profound inhibition of humoral response to recall antigens (reviewed in Vihinen et al Frontiers in Bioscience 5: d917-928). Mice deficient in BTK also have a reduced number of peripheral B cells and greatly decreased serum levels of IgM and IgG3. BTK deletion in mice has a profound effect on B cell proliferation induced by anti-IgM, and inhibits immune responses to thymus-independent type II antigens (Ellmeier et al, J Exp Med 192: 1611-1623 (2000)). BTK also plays a crucial role in mast cell activation through the high-affinity IgE receptor (Fc epsilon RI). BTK deficient murine mast cells have reduced degranulation and decreased production of proinflammatory cytokines following Fc epsilon RI cross-linking (Kawakami et al. Journal of Leukocyte Biology 65: 286-290).

Provided compounds are inhibitors of BTK and are therefore useful for treating one or more disorders associated with activity of BTK. Thus, in some embodiments, the present invention provides a method for treating a BTK-mediated disorder comprising the step of administering to a patient in need thereof a compound of the present invention, or pharmaceutically acceptable composition thereof.

As used herein, the term "BTK-mediated" disorders or conditions as used herein means any disease or other deleterious condition in which BTK, or a mutant thereof, is known to play a role. Accordingly, another embodiment of the present invention relates to treating or lessening the severity of one or more diseases in which BTK, or a mutant thereof, is known to play a role. Specifically, the present invention relates to a method of treating or lessening the severity of a disease or condition selected from a proliferative disorder or an autoimmune disorder, wherein said method comprises administering to a patient in need thereof a compound or composition according to the present invention.

In some embodiments, the present invention provides a method for treating or lessening the severity of one or more diseases and conditions associated with BTK. In some embodiments, the disease or condition is an autoimmune disease, e.g., inflammatory bowel disease, arthritis, systemic lupus erythematosus (SLE or lupus), lupus nephritis, vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, or vulvodynia. In certain embodiments, the disease or condition is systemic lupus erythematosus (SLE or lupus) or lupus nephritis.

In some embodiments, the disease or condition is a hyperproliferative disease or immunologically-mediated diseases including rejection of transplanted organs or tissues and Acquired Immunodeficiency Syndrome (AIDS, also known as HIV).

In some embodiments, the present invention provides a method for treating or lessening the severity of one or more diseases and conditions associated with BTK, wherein the disease or condition is selected from heteroimmune conditions or diseases, which include, but are not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

In some embodiments, the present invention provides a method for treating or lessening the severity of one or more diseases and conditions associated with BTK, wherein the disease or condition is selected from an inflammatory disease, e.g., asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments, the present invention provides a method for treating or lessening the severity of one or more diseases and conditions associated with BTK, wherein the disease or condition is selected from a cancer. In one embodiment, the cancer is a B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis. In some embodiments, the cancer is breast cancer, prostate cancer, or cancer of the mast cells (e.g., mastocytoma, mast cell leukemia, mast cell sarcoma, systemic mastocytosis). In one embodiment, the cancer is bone cancer. In another embodiment, the cancer is of other primary origin and metastasizes to the bone. In certain embodiments, the cancer is colorectal cancer or pancreatic cancer.

In some embodiments, the present invention provides a method for treating or lessening the severity of one or more diseases or conditions associated with BTK including diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, and bone metastasis.

In some embodiments, the present invention provides a method for treating or lessening the severity of one or more diseases and conditions associated with BTK, wherein the disease or condition is selected from a thromboembolic disorder or cardiovascular disorder, e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis. In certain embodiments, the present invention provides an anti-thrombotic agent because Btk is also involved in the activation of platelets.

In some embodiments, the present invention provides a method for treating or lessening the severity of one or more diseases and conditions associated with BTK, including infectious and noninfectious inflammatory events and auto-immune and other inflammatory diseases. These autoimmune and inflammatory diseases, disorders, and syndromes include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease. In certain embodiments, the diabetes is type I diabetes.

In some embodiments, the present invention provides a method for treating or lessening the severity of one or more diseases and conditions associated with BTK, selected from rheumatoid arthritis, multiple sclerosis, B-cell chronic lymphocytic leukemia, acute lymphocytic leukemia, hairy cell leukemia, non-Hodgkin's lymphoma, Hodgkin's lymphoma, multiple myeloma, bone cancer, bone metastasis, osteoporosis, diabetes (e.g. type I diabetes), irritable bowel syndrome, Crohn's disease, lupus and renal transplant.

It is another object of the invention to provide a method for treating diseases that are caused, mediated and/or propagated by BTK activity, wherein at least one compound of formula (I) according to the invention and/or physiologically acceptable salts thereof is administered to a mammal in need of such treatment. In certain embodiments, the invention provides a method for treating lupus, wherein at least one compound of formula (I) according to the invention and/or physiologically acceptable salts thereof is administered to a mammal in need of such treatment. In certain embodiments, the compound is administered in an effective amount as defined above. In certain embodiments, the treatment is an oral administration.

The method of the invention can be performed either in-vitro or in-vivo. The susceptibility of a particular cell to treatment with the compounds according to the invention can be particularly determined by in-vitro tests, whether in the course of research or clinical application. Typically, a culture of the cell is combined with a compound according to the invention at various concentrations for a period of time which is sufficient to allow the active agents to inhibit BTK activity, usually between about one hour and one week. In-vitro treatment can be carried out using cultivated cells from a biopsy sample or cell line.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

For identification of a signal transduction pathway and for detection of interactions between various signal transduction pathways, various scientists have developed suitable models or model systems, for example cell culture models and models of transgenic animals. For the determination of certain stages in the signal transduction cascade, interacting compounds can be utilized in order to modulate the signal. The compounds according to the invention can also be used as reagents for testing BTK-dependent signal transduction pathways in animals and/or cell culture models or in the clinical diseases mentioned in this application.

Moreover, the subsequent teaching of the present specification concerning the use of the compounds according to formula (I) and its derivatives for the production of a medicament for the prophylactic or therapeutic treatment and/or monitoring is considered as valid and applicable without restrictions to the use of the compound for the inhibition of BTK activity if expedient.

The invention also relates to the use of compounds according to formula (I) and/or physiologically acceptable salts thereof for the prophylactic or therapeutic treatment and/or monitoring of diseases that are caused, mediated and/or propagated by BTK activity. Furthermore, the invention relates to the use of compounds according to formula (I) and/or physiologically acceptable salts thereof for the production of a medicament for the prophylactic or therapeutic treatment and/or monitoring of diseases that are caused, mediated and/or propagated by BTK activity. In certain embodiments, the invention provides the use of a compound according to formula I or physiologically acceptable salts thereof, for the production of a medicament for the prophylactic or therapeutic treatment of a BTK-mediated disorder.

Compounds of formula (I) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

Another object of the present invention are compounds of formula (I) according to the invention and/or physiologically acceptable salts thereof for use in the prophylactic or therapeutic treatment and/or monitoring of diseases that are caused, mediated and/or propagated by BTK activity. Another preferred object of the invention concerns compounds of formula (I) according to the invention and/or physiologically acceptable salts thereof for use in the prophylactic or therapeutic treatment and/or monitoring of lupus. The prior teaching of the present specification concerning the compounds of formula (I), including any preferred embodiment thereof, is valid and applicable without restrictions to the compounds according to formula (I) and their salts for use in the prophylactic or therapeutic treatment and/or monitoring of lupus.

The compounds of formula (I) according to the invention can be administered before or following an onset of disease once or several times acting as therapy. The aforementioned compounds and medical products of the inventive use are particularly used for the therapeutic treatment. A therapeutically relevant effect relieves to some extent one or more symptoms of a disorder, or returns to normality, either partially or completely, one or more physiological or biochemical parameters associated with or causative of a disease or pathological condition. Monitoring is considered as a kind of treatment provided that the compounds are administered in distinct intervals, e.g. in order to boost the response and eradicate the pathogens and/or symptoms of the disease completely. Either the identical compound or different compounds can be applied. The methods of the invention can also be used to reduce the likelihood of developing a disorder or even prevent the initiation of disorders associated with BTK activity in advance or to treat the arising and continuing symptoms.

In the meaning of the invention, prophylactic treatment is advisable if the subject possesses any preconditions for the aforementioned physiological or pathological conditions, such as a familial disposition, a genetic defect, or a previously incurred disease.

The invention furthermore relates to a medicament comprising at least one compound according to the invention and/or pharmaceutically usable derivatives, salts, solvates and stereoisomers thereof, including mixtures thereof in all ratios. In certain embodiments, the invention relates to a medicament comprising at least one compound according to the invention and/or physiologically acceptable salts thereof.

A "medicament" in the meaning of the invention is any agent in the field of medicine, which comprises one or more compounds of formula (I) or preparations thereof (e.g. a pharmaceutical composition or pharmaceutical formulation) and can be used in prophylaxis, therapy, follow-up or aftercare of patients who suffer from diseases, which are associated with BTK activity, in such a way that a pathogenic modification of their overall condition or of the condition of particular regions of the organism could establish at least temporarily.

In various embodiments, the active ingredient may be administered alone or in combination with other treatments. A synergistic effect may be achieved by using more than one compound in the pharmaceutical composition, i.e. the compound of formula (I) is combined with at least another agent as active ingredient, which is either another compound of formula (I) or a compound of different structural scaffold. The active ingredients can be used either simultaneously or sequentially.

Included herein are methods of treatment in which at least one chemical entity provided herein is administered in combination with an anti-inflammatory agent. Anti-inflammatory agents include but are not limited to NSAIDs, non-specific and COX-2 specific cyclooxygenase enzyme inhibitors, gold compounds, corticosteroids, methotrexate, tumor necrosis factor (TNF) antagonists, immunosuppressants and methotrexate. Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory compound is an anti-monoclonal antibody (such as eculizumab or pexelizumab), a TNF antagonist, such as entanercept, or infliximab, which is an anti-TNF alpha monoclonal antibody.

Still other embodiments of the inventioBergen pertain to combinations in which at least one active agent is an immunosuppressant compound such as an immunosuppressant compound chosen from methotrexate, leflunomide, cyclosporine, tacrolimus, azathioprine, and mycophenolate mofetil.

B-cells and B-cell precursors expressing BTK have been implicated in the pathology of B-cell malignancies, including, but not limited to, B-cell lymphoma, lymphoma (including Hodgkin's and non-Hodgkin's lymphoma), hairy cell lymphoma, multiple myeloma, chronic and acute myelogenous leukemia and chronic and acute lymphocytic leukemia.

BTK has been shown to be an inhibitor of the Fas/APO-1 (CD-95) death inducing signaling complex (DISC) in B-lineage lymphoid cells. The fate of leukemia/lymphoma cells may reside in the balance between the opposing proapoptotic effects of caspases activated by DISC and an upstream anti-apoptotic regulatory mechanism involving BTK and/or its substrates (Vassilev et al., J. Biol. Chem. 1998, 274, 1646-1656).

It has also been discovered that BTK inhibitors are useful as chemosensitizing agents, and, thus, are useful in combination with other chemotherapeutic drugs, in particular, drugs that induce apoptosis. Examples of other chemotherapeutic drugs that can be used in combination with chemosensitizing BTK inhibitors include topoisomerase I inhibitors (camptothecin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

In another aspect, the invention provides for a kit consisting of separate packs of an effective amount of a compound according to the invention and/or pharmaceutically acceptable salts, derivatives, solvates and stereoisomers thereof, including mixtures thereof in all ratios, and optionally, an effective amount of a further active ingredient. The kit comprises suitable containers, such as boxes, individual bottles, bags or ampoules. The kit may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further active ingredient in dissolved or lyophilized form.

As used herein, the terms "treatment," "treat," and "treating" refer to reversing, alleviating, delaying the onset of, or inhibiting the progress of a disease or disorder, or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent or delay their recurrence.

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention are administered orally or parenterally at dosage levels of about 0.01 mg/kg to about 100 mg/kg and preferably from about 1 mg/kg to about 50 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms optionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions are formulated according to the known art using suitable dispersing or wetting agents and suspending agents. The sterile injectable preparation are also a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This is accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form also optionally comprises buffering agents.

Solid compositions of a similar type are also employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type are also employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms also comprise, as is normal practice, additional substances other than inert diluents, e.g., tableting lubricants and other tableting aids such a magnesium stearate and microcrystalline cellulose. In the case of capsules, tablets and pills, the dosage forms optionally also comprise buffering agents. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting BTK activity in a biological sample comprising the step of contacting said biological sample with a compound of this invention, or a composition comprising said compound.

According to another embodiment, the invention relates to a method of inhibiting BTK, or a mutant thereof, activity in a biological sample in a positive manner, comprising the step of contacting said biological sample with a compound of this invention, or a composition comprising said compound.

The compounds of the invention are useful in-vitro as unique tools for understanding the biological role of BTK, including the evaluation of the many factors thought to influence, and be influenced by, the production of BTK and the interaction of BTK. The present compounds are also useful in the development of other compounds that interact with BTK since the present compounds provide important structure-activity relationship (SAR) information that facilitate that development. Compounds of the present invention that bind to BTK can be used as reagents for detecting BTK in living cells, fixed cells, in biological fluids, in tissue homogenates, in purified, natural biological materials, etc. For example, by labeling such compounds, one can identify cells expressing BTK. In addition, based on their ability to bind BTK, compounds of the present invention can be used in in-situ staining, FACS (fluorescence-activated cell sorting), sodium dodecyl sulfate polyacrylamide gel electrophoresis (SDS-PAGE), ELISA (enzyme-linked immunoadsorptive assay), etc., enzyme purification, or in purifying cells expressing BTK inside permeabilized cells. The compounds of the invention can also be utilized as commercial research reagents for various medical research and diagnostic uses. Such uses can include but are not limited to: use as a calibration standard for quantifying the activities of candidate BTK inhibitors in a variety of functional assays; use as blocking reagents in random compound screening, i.e. in looking for new families of BTK ligands, the compounds can be used to block recovery of the presently claimed BTK compounds; use in the co-crystallization with BTK enzyme, i.e. the compounds of the present invention will allow formation of crystals of the compound bound to BTK, enabling the determination of enzyme/compound structure by x-ray crystallography; other research and diagnostic applications, wherein BTK is preferably activated or such activation is conveniently calibrated against a known quantity of an BTK inhibitor, etc.; use in assays as probes for determining the expression of BTK in cells; and developing assays for detecting compounds which bind to the same site as the BTK binding ligands.

The compounds of the invention can be applied either themselves and/or in combination with physical measurements for diagnostics of treatment effectiveness. Pharmaceutical compositions containing said compounds and the use of said compounds to treat BTK-mediated conditions is a promising, novel approach for a broad spectrum of therapies causing a direct and immediate improvement in the state of health, whether in human or animal. The orally bioavailable and active new chemical entities of the invention improve convenience for patients and compliance for physicians.

The compounds of formula (I), their salts, isomers, tautomers, enantiomeric forms, diastereomers, racemates, derivatives, prodrugs and/or metabolites are characterized by a high specificity and stability, low manufacturing costs and convenient handling. These features form the basis for a reproducible action, wherein the lack of cross-reactivity is included, and for a reliable and safe interaction with the target structure.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of BTK, or a mutant thereof, activity in a biological sample is useful for a variety of purposes that are known to one of skill in the art. Examples of such purposes include, but are not limited to, blood transfusion, organ transplantation, biological specimen storage, and biological assays.

5. Probe Compounds

In certain aspects, a compound of the present invention is tethered to a detectable moiety to form a probe compound. In one aspect, a probe compound of the invention comprises an irreversible protein kinase inhibitor of any formulae as described herein, a detectable moiety, and a tethering moiety that attaches the inhibitor to the detectable moiety.

In some embodiments, such probe compounds of the present invention comprise a provided compound of any formulae as described herein, tethered to a detectable moiety, $R^r$, by a bivalent tethering moiety, $-T^1-$. The tethering moiety is attached to a compound of the invention via $R^1$. One of ordinary skill in the art will appreciate that when a tethering moiety is attached to $R^1$, $R^1$ is a bivalent warhead group denoted as $R^1$. In certain embodiments, a provided probe compound is selected from formula I-t:

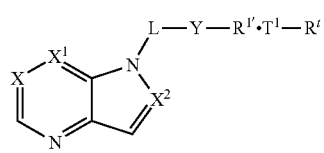

wherein each of X, $X^1$, $X^2$, L, and Y, is as defined above, and described in classes and subclasses herein, $R^{1'}$ is a bivalent $R^1$; $T^1$ is a bivalent tethering moiety; and $R^r$ is a detectable moiety.

In some embodiments, such probe compounds of the present invention comprise a provided compound of any formulae as described herein, tethered to a detectable moiety, $R^r$, by a bivalent tethering moiety, $-T^1-$. In certain embodiments, a provided probe compound is selected from formula I-s:

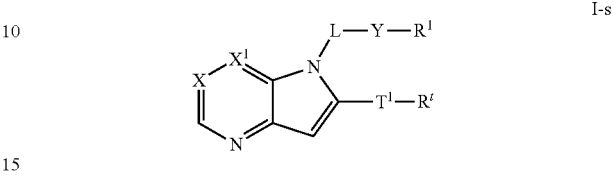

wherein each of X, $X^1$, $R^1$, L, and Y, is as defined above, and described in classes and subclasses herein, $T^1$ is a bivalent tethering moiety; and $R^r$ is a detectable moiety.

In some embodiments, $R^r$ is a detectable moiety selected from a primary label or a secondary label. In certain embodiments, $R^r$ is a detectable moiety selected from a fluorescent label (e.g., a fluorescent dye or a fluorophore), a mass-tag, a chemiluminescent group, a chromophore, an electron dense group, or an energy transfer agent. In some embodiments, $R^r$ is biotin, biotin sulfoxide, a radioisotope, or a fluorescent label.

As used herein, the term "detectable moiety" is used interchangeably with the term "label" and "reporter" and relates to any moiety capable of being detected, e.g., primary labels and secondary labels. A presence of a detectable moiety can be measured using methods for quantifying (in absolute, approximate or relative terms) the detectable moiety in a system under study. In some embodiments, such methods are well known to one of ordinary skill in the art and include any methods that quantify a reporter moiety (e.g., a label, a dye, a photocrosslinker, a cytotoxic compound, a drug, an affinity label, a photoaffinity label, a reactive compound, an antibody or antibody fragment, a biomaterial, a nanoparticle, a spin label, a fluorophore, a metal-containing moiety, a radioactive moiety, quantum dot(s), a novel functional group, a group that covalently or noncovalently interacts with other molecules, a photocaged moiety, an actinic radiation excitable moiety, a ligand, a photoisomerizable moiety, biotin, a biotin analog (e.g., biotin sulfoxide), a moiety incorporating a heavy atom, a chemically cleavable group, a photocleavable group, a redox-active agent, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, and any combination of the above).

Primary labels, such as radioisotopes (e.g., tritium, $^{32}P$, $^{33}P$, $^{35}S$, $^{14}C$, $^{123}I$, $^{124}I$, $^{125}I$, or $^{131}I$), mass-tags are stable isotopes (e.g., $^{13}C$, $^{2}H$, $^{17}O$, $^{18}O$, $^{15}N$, $^{19}F$, and $^{127}I$), positron emitting isotopes (e.g., $^{11}C$, $^{18}F$, $^{13}N$, $^{124}I$, and $^{15}O$), and fluorescent labels, which are signal generating reporter groups which can be detected without further modifications. Detectable moieties are analyzed by methods. Exemplary methods are fluorescence, positron emission tomography, SPECT medical imaging, chemiluminescence, electron-spin resonance, ultraviolet/visible absorbance spectroscopy, mass spectrometry, nuclear magnetic resonance, magnetic resonance, flow cytometry, autoradiography, scintillation counting, phosphoimaging, and electrochemical methods.

The term "secondary label" as used herein refers to moieties such as biotin and various protein antigens that require the presence of a second intermediate for production of a detectable signal. For biotin, the secondary intermediate includes streptavidin-enzyme or strepavidin-antibody conjugates. For antigen labels, secondary intermediates include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 493/503, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxyfluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X, 5(6)-Carboxyfluorescein, 2,7-Dichlorofluorescein, N,N-Bis(2,4,6-trimethylphenyl)-3,4:9,10-perylenebis(dicarboximide), HPTS, Ethyl Eosin, DY-490XL MegaStokes, DY-485XL MegaStokes, Adirondack Green 520, ATTO 465, ATTO 488, ATTO 495, YOYO-1,5-FAM, BCECF, dichlorofluorescein, rhodamine 110, rhodamine 123, YO-PRO-1, SYTOX Green, Sodium Green, SYBR Green I, Alexa Fluor 500, FITC, Fluo-3, Fluo-4, fluoro-emerald, YoYo-1 ssDNA, YoYo-1 dsDNA, YoYo-1, SYTO RNASelect, Diversa Green-FP, Dragon Green, EvaGreen, Surf Green EX, Spectrum Green, NeuroTrace 500525, NBD-X, MitoTracker Green FM, LysoTracker Green DND-26, CBQCA, PA-GFP (post-activation), WEGFP (post-activation), FlASH-CCXXCC, Azami Green monomeric, Azami Green, green fluorescent protein (GFP), EGFP (Campbell Tsien 2003), EGFP (Patterson 2001), Kaede Green, 7-Benzylamino-4-Nitrobenz-2-Oxa-1,3-Diazole, Bexl, Doxorubicin, Lumio Green, and SuperGlo GFP.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-methoxytetrafluorobenzyl)oxy]phenyl]-3-methylglyceronyl]isonipecotic acid, 4'-[2,3,5,6-tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) are also used as mass-tags. Stable isotopes (e.g., $^{13}C$, $^{2}H$, $^{17}O$, $^{18}O$, and $^{15}N$) are also used as mass-tags.

The term "chemiluminescent group," as used herein, refers to a group which emits light as a result of a chemical reaction without the addition of heat. By way of example, luminol (5-amino-2,3-dihydro-1,4-phthalazinedione) reacts with oxidants like hydrogen peroxide ($H_2O_2$) in the presence of a base and a metal catalyst to produce an excited state product (3-aminophthalate, 3-APA).

The term "chromophore," as used herein, refers to a molecule which absorbs light of visible wavelengths, UV wavelengths or IR wavelengths.

The term "dye," as used herein, refers to a soluble, coloring substance which contains a chromophore.

The term "electron dense group," as used herein, refers to a group which scatters electrons when irradiated with an electron beam. Such groups include, but are not limited to, ammonium molybdate, bismuth subnitrate, cadmium iodide, carbohydrazide, ferric chloride hexahydrate, hexamethylene tetramine, indium trichloride anhydrous, lanthanum nitrate, lead acetate trihydrate, lead citrate trihydrate, lead nitrate, periodic acid, phosphomolybdic acid, phosphotungstic acid, potassium ferricyanide, potassium ferrocyanide, ruthenium red, silver nitrate, silver proteinate (Ag Assay: 8.0-8.5%) "Strong", silver tetraphenylporphin (S-TPPS), sodium chloroaurate, sodium tungstate, thallium nitrate, thiosemicarbazide (TSC), uranyl acetate, uranyl nitrate, and vanadyl sulfate.

The term "energy transfer agent," as used herein, refers to a molecule which either donates or accepts energy from another molecule. By way of example only, fluorescence resonance energy transfer (FRET) is a dipole-dipole coupling process by which the excited-state energy of a fluorescence donor molecule is non-radiatively transferred to an unexcited acceptor molecule which then fluorescently emits the donated energy at a longer wavelength.

The term "moiety incorporating a heavy atom," as used herein, refers to a group which incorporates an ion or atom which is usually heavier than carbon. In some embodiments, such ions or atoms include, but are not limited to, silicon, tungsten, gold, lead, and uranium.

The term "photoaffinity label," as used herein, refers to a label with a group, which, upon exposure to light, forms a covalent bond with a molecule for which the label has an affinity.

The term "photocaged moiety," as used herein, refers to a group which, upon illumination at certain wavelengths, covalently or non-covalently binds other ions or molecules.

The term "photoisomerizable moiety," as used herein, refers to a group wherein upon illumination with light changes from one isomeric form to another.

The term "radioactive moiety," as used herein, refers to a group whose nuclei spontaneously give off nuclear radiation, such as alpha, beta, or gamma particles; wherein, alpha particles are helium nuclei, beta particles are electrons, and gamma particles are high energy photons.

The term "spin label," as used herein, refers to molecules which contain an atom or a group of atoms exhibiting an unpaired electron spin (i.e. a stable paramagnetic group) that in some embodiments are detected by electron spin resonance spectroscopy and in other embodiments are attached to another molecule. Such spin-label molecules include, but are not limited to, nitryl radicals and nitroxides, and in some embodiments are single spin-labels or double spin-labels.

The term "quantum dots," as used herein, refers to colloidal semiconductor nanocrystals that in some embodiments are detected in the near-infrared and have extremely high quantum yields (i.e., very bright upon modest illumination).

One of ordinary skill in the art will recognize that a detectable moiety is attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties are directly attached to a provided compound or via a tethering moiety, such as a bivalent saturated or unsaturated hydrocarbon chain.

In some embodiments, detectable moieties are attached to a provided compound via click chemistry. In some embodiments, such moieties are attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57. In some embodiments, a click ready inhibitor moiety is provided and reacted with a click ready -T-$R^r$ moiety. As used herein, "click ready" refers to a moiety containing an azide or alkyne for use in a click chemistry reaction. In some embodiments, the click ready inhibitor moiety comprises an azide. In certain embodiments, the click ready -T-$R^r$ moiety comprises a strained cyclooctyne for use in a copper-free click chemistry reaction (for example, using methods described in Baskin et al., Proc. Natl. Acad. Sci. USA 2007, 104, 16793-16797).

In some embodiments, the detectable moiety, $R^r$, is selected from a label, a dye, a photocrosslinker, a cytotoxic compound, a drug, an affinity label, a photoaffinity label, a reactive compound, an antibody or antibody fragment, a biomaterial, a nanoparticle, a spin label, a fluorophore, a metal-containing moiety, a radioactive moiety, quantum dot(s), a novel functional group, a group that covalently or noncovalently interacts with other molecules, a photocaged moiety, an actinic radiation excitable moiety, a ligand, a photoisomerizable moiety, biotin, a biotin analog (e.g., biotin sulfoxide), a moiety incorporating a heavy atom, a chemically cleavable group, a photocleavable group, a redox-active agent, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, or a combination thereof.

In some embodiments, $R^r$ is biotin or an analog thereof. In certain embodiments, $R^r$ is biotin. In certain other embodiments, $R^r$ is biotin sulfoxide.

In another embodiment, $R^r$ is a fluorophore. In a further embodiment, the fluorophore is selected from Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 493/503, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X, 5(6)-Carboxyfluorescein, 2,7-Dichlorofluorescein, N,N-Bis(2,4,6-trimethylphenyl)-3,4:9,10-perylenebis(dicarboximide), HPTS, Ethyl Eosin, DY-490XL MegaStokes, DY-485XL MegaStokes, Adirondack Green 520, ATTO 465, ATTO 488, ATTO 495, YOYO-1,5-FAM, BCECF, dichlorofluorescein, rhodamine 110, rhodamine 123, YO-PRO-1, SYTOX Green, Sodium Green, SYBR Green I, Alexa Fluor 500, FITC, Fluo-3, Fluo-4, fluoro-emerald, YoYo-1 ssDNA, YoYo-1 dsDNA, YoYo-1, SYTO RNASelect, Diversa Green-FP, Dragon Green, EvaGreen, Surf Green EX, Spectrum Green, NeuroTrace 500525, NBD-X, MitoTracker Green FM, LysoTracker Green DND-26, CBQCA, PA-GFP (post-activation), WEGFP (post-activation), FlASH-CCXXCC, Azami Green monomeric, Azami Green, green fluorescent protein (GFP), EGFP (Campbell Tsien 2003), EGFP (Patterson 2001), Kaede Green, 7-Benzylamino-4-Nitrobenz-2-Oxa-1,3-Diazole, Bexl, Doxorubicin, Lumio Green, or SuperGlo GFP.

As described generally above, a provided probe compound comprises a tethering moiety, -$T^1$-, that attaches the irreversible inhibitor to the detectable moiety. As used herein, the term "tether" or "tethering moiety" refers to any bivalent chemical spacer. Exemplary tethers are a covalent bond, a polymer, a water soluble polymer, optionally substituted alkyl, optionally substituted heteroalkyl, optionally substituted heterocycloalkyl, optionally substituted cycloalkyl, optionally substituted heterocyclyl, optionally substituted heterocycloalkylalkyl, optionally substituted heterocycloalkylalkenyl, optionally substituted aryl, optionally substituted heteroaryl, optionally substituted heterocycloalkylalkenylalkyl, an optionally substituted amide moiety, an ether moiety, an ketone moiety, an ester moiety, an optionally substituted carbamate moiety, an optionally substituted hydrazone moiety, an optionally substituted hydrazine moiety, an optionally substituted oxime moiety, a disulfide moiety, an optionally substituted imine moiety, an optionally substituted sulfonamide moiety, a sulfone moiety, a sulfoxide moiety, a thioether moiety, or any combination thereof.

In some embodiments, the tethering moiety, -$T^1$-, is selected from a covalent bond, a polymer, a water soluble polymer, optionally substituted alkyl, optionally substituted heteroalkyl, optionally substituted heterocycloalkyl, optionally substituted cycloalkyl, optionally substituted heterocycloalkylalkyl, optionally substituted heterocycloalkylalkenyl, optionally substituted aryl, optionally substituted heteroaryl, and optionally substituted heterocycloalkylalkenylalkyl. In some embodiments, the tethering moiety is an optionally substituted heterocycle. In other embodiments, the heterocycle is selected from aziridine, oxirane, episulfide, azetidine, oxetane, pyrroline, tetrahydrofuran, tetrahydrothiophene, pyrrolidine, pyrazole, pyrrole, imidazole, triazole, tetrazole, oxazole, isoxazole, oxirene, thiazole,- isothiazole, dithiolane, furan, thiophene, piperidine, tetrahydropyran, thiane, pyridine, pyran, thiapyrane, pyridazine, pyrimidine, pyrazine, piperazine, oxazine, thiazine, dithiane, and dioxane. In some embodiments, the heterocycle is piperazine. In further embodiments, the tethering moiety is optionally substituted with halogen, —CN, —OH, —NO$_2$, alkyl, S(O), and S(O)$_2$. In other embodiments, the water soluble polymer is a PEG group.

In other embodiments, the tethering moiety provides sufficient spatial separation between the detectable moiety and the protein kinase inhibitor moiety. In further embodiments, the tethering moiety is stable. In yet a further embodiment, the tethering moiety does not substantially affect the response of the detectable moiety. In other embodiments, the tethering moiety provides chemical stability to the probe compound. In further embodiments, the tethering moiety provides sufficient solubility to the probe compound.

In some embodiments, a tethering moiety, -T$^1$-, such as a water soluble polymer is coupled at one end to a provided irreversible inhibitor and to a detectable moiety, R$^t$, at the other end. In other embodiments, a water soluble polymer is coupled via a functional group or substituent of the provided irreversible inhibitor. In further embodiments, a water soluble polymer is coupled via a functional group or substituent of the reporter moiety.

In some embodiments, examples of hydrophilic polymers, for use in tethering moiety -T$^1$-, include, but are not limited to: polyalkyl ethers and alkoxy-capped analogs thereof (e.g., polyoxyethylene glycol, polyoxyethylene/propylene glycol, and methoxy or ethoxy-capped analogs thereof, polyoxyethylene glycol, the latter is also known as polyethylene glycol or PEG); polyvinylpyrrolidones; polyvinylalkyl ethers; polyoxazolines, polyalkyl oxazolines and polyhydroxyalkyl oxazolines; polyacrylamides, polyalkyl acrylamides, and polyhydroxyalkyl acrylamides (e.g., polyhydroxypropylmethacrylamide and derivatives thereof); polyhydroxyalkyl acrylates; polysialic acids and analogs thereof, hydrophilic peptide sequences; polysaccharides and their derivatives, including dextran and dextran derivatives, e.g., carboxymethyldextran, dextran sulfates, aminodextran; cellulose and its derivatives, e.g., carboxymethyl cellulose, hydroxyalkyl celluloses; chitin and its derivatives, e.g., chitosan, succinyl chitosan, carboxymethylchitin, carboxymethylchitosan; hyaluronic acid and its derivatives; starches; alginates; chondroitin sulfate; albumin; pullulan and carboxymethyl pullulan; polyaminoacids and derivatives thereof, e.g., polyglutamic acids, polylysines, polyaspartic acids, polyaspartamides; maleic anhydride copolymers such as: styrene maleic anhydride copolymer, divinylethyl ether maleic anhydride copolymer; polyvinyl alcohols; copolymers thereof, terpolymers thereof, mixtures thereof, and derivatives of the foregoing. In other embodiments, a water soluble polymer is any structural form. Exemplary forms are linear, forked or branched. In further embodiments, multifunctional polymer derivatives include, but are not limited to, linear polymers having two termini, each terminus being bonded to a functional group which is the same or different.

In some embodiments, a water polymer comprises a poly(ethylene glycol) moiety. In further embodiments, the molecular weight of the polymer is of a wide range. Exemplary ranges are between about 100 Da and about 100,000 Da or more. In yet further embodiments, the molecular weight of the polymer is between about 100 Da and about 100,000 Da, about 100,000 Da, about 95,000 Da, about 90,000 Da, about 85,000 Da, about 80,000 Da, about 75,000 Da, about 70,000 Da, about 65,000 Da, about 60,000 Da, about 55,000 Da, about 50,000 Da, about 45,000 Da, about 40,000 Da, about 35,000 Da, 30,000 Da, about 25,000 Da, about 20,000 Da, about 15,000 Da, about 10,000 Da, about 9,000 Da, about 8,000 Da, about 7,000 Da, about 6,000 Da, about 5,000 Da, about 4,000 Da, about 3,000 Da, about 2,000 Da, about 1,000 Da, about 900 Da, about 800 Da, about 700 Da, about 600 Da, about 500 Da, about 400 Da, about 300 Da, about 200 Da, and about 100 Da. In some embodiments, the molecular weight of the polymer is between about 100 Da and 50,000 Da. In some embodiments, the molecular weight of the polymer is between about 100 Da and 40,000 Da. In some embodiments, the molecular weight of the polymer is between about 1,000 Da and 40,000 Da. In some embodiments, the molecular weight of the polymer is between about 5,000 Da and 40,000 Da. In some embodiments, the molecular weight of the polymer is between about 10,000 Da and 40,000 Da. In some embodiments, the poly(ethylene glycol) molecule is a branched polymer. In further embodiments, the molecular weight of the branched chain PEG is between about 1,000 Da and about 100,000 Da. Exemplary ranges are about 100,000 Da, about 95,000 Da, about 90,000 Da, about 85,000 Da, about 80,000 Da, about 75,000 Da, about 70,000 Da, about 65,000 Da, about 60,000 Da, about 55,000 Da, about 50,000 Da, about 45,000 Da, about 40,000 Da, about 35,000 Da, about 30,000 Da, about 25,000 Da, about 20,000 Da, about 15,000 Da, about 10,000 Da, about 9,000 Da, about 8,000 Da, about 7,000 Da, about 6,000 Da, about 5,000 Da, about 4,000 Da, about 3,000 Da, about 2,000 Da, and about 1,000 Da. In some embodiments, the molecular weight of a branched chain PEG is between about 1,000 Da and about 50,000 Da. In some embodiments, the molecular weight of a branched chain PEG is between about 1,000 Da and about 40,000 Da. In some embodiments, the molecular weight of a branched chain PEG is between about 5,000 Da and about 40,000 Da. In some embodiments, the molecular weight of a branched chain PEG is between about 5,000 Da and about 20,000 Da. The foregoing list for substantially water soluble backbones is by no means exhaustive and is merely illustrative, and in some embodiments, polymeric materials having the qualities described above are suitable for use in methods and compositions described herein.

In certain embodiments, the tethering moiety, -T$^1$-, has the following structure:

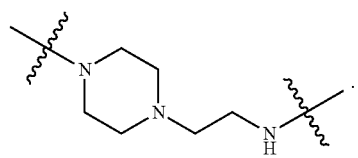 [SMILES: *NCCN1CCN(*)CC1]

In certain embodiments, the tethering moiety, -T¹-, has the following structure:

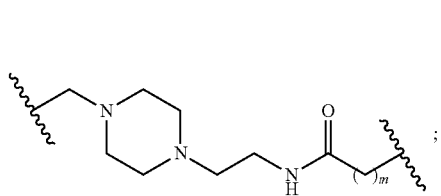

wherein m is 0, 1, 2, 3, 4, 5, 6, or 7.

In certain embodiments, —R' is quinine, phenylalanine, tyrosine, tryptophan, NADH, FMN, EDANS, Lucifer Yellow, pyrene, 4-MU, AMC, DAPI, Hoechst33342, NBD, bimane, Cascade yellow, fluorescein, RH110, TMR, SRh101, naphthofluorescein, SNARF-1, propidium, BODIPY-FL, BODIPY-TR, Cy3, Cy5, Cy7, IRDye 700DX, or resorufin.

In some embodiments, -T¹-R' is of the following structure:

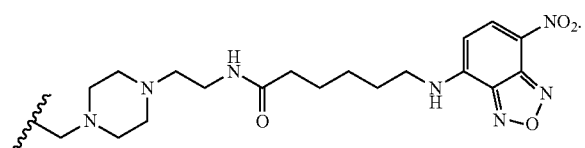 [SMILES: *CN1CCN(CCNC(=O)CCCCCNc2ccc([N+](=O)[O-])c3nonc23)CC1]

In some embodiments, -T¹-R' is of the following structure:

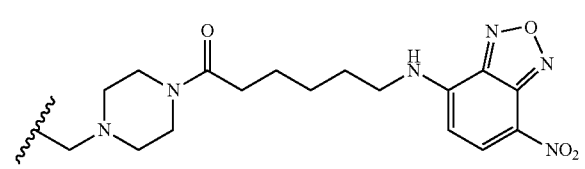 [SMILES: *CN1CCN(C(=O)CCCCCNc2ccc([N+](=O)[O-])c3nonc23)CC1]

In certain embodiments, -T¹-R' is of the following structure:

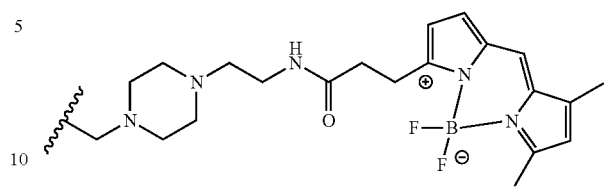

In certain embodiments, -T¹-R' is of the following structure:

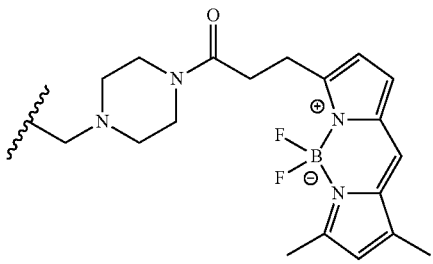

In certain embodiments, -T¹-R' is of the following structure:

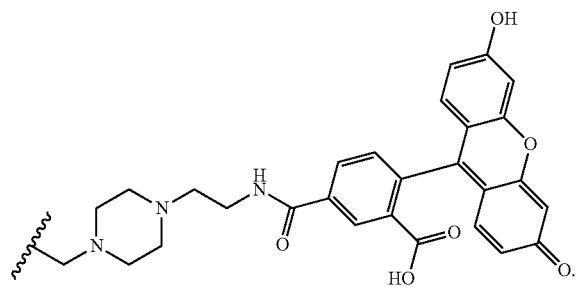 [SMILES: *CN1CCN(CCNC(=O)c2ccc(-c3c4ccc(=O)cc-4oc4cc(O)ccc34)c(C(=O)O)c2)CC1]

In certain embodiments, -T¹-R' is of the following structure:

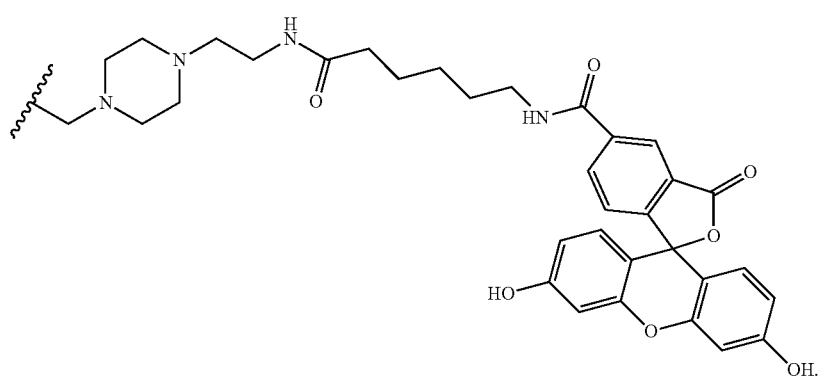 [SMILES: *CN1CCN(CCNC(=O)CCCCCNC(=O)c2ccc3c(c2)C(=O)OC32c3ccc(O)cc3Oc3cc(O)ccc32)CC1]

In certain embodiments, -T¹-R' is of the following structure:

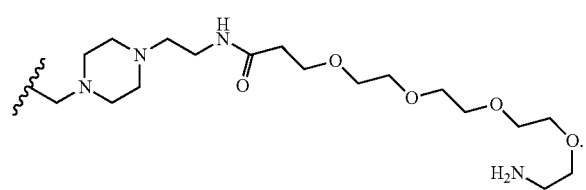 [SMILES: *CN1CCN(CCNC(=O)CCOCCOCCOCCOCCN)CC1]

In certain embodiments, -T¹-R' is of the following structure:

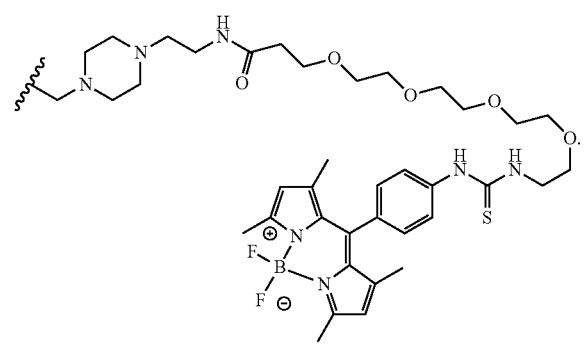

In certain embodiments, -T¹-R' is of the following structure:

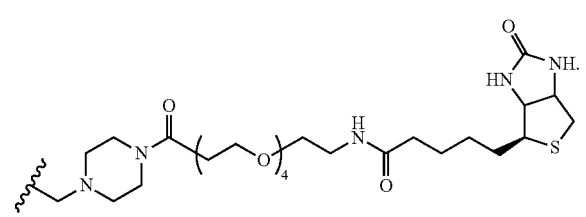

In certain embodiments, -T¹-R' is of the following structure:

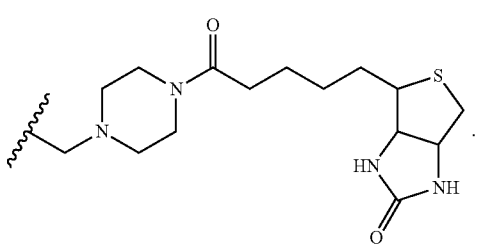 [SMILES: *CN1CCN(C(=O)CCCCC2SCC3NC(=O)NC32)CC1]

In some embodiments, a probe compound of formula I-t or formula I-s is derived from any compound described herein.

In certain embodiments, the probe compound is selected from compounds 31, 32, 53, 54, 73, or 74. In certain embodiments, the probe compound is compound 31. In certain embodiments, the probe compound is compound 32. In certain embodiments, the probe compound is compound 53. In certain embodiments, the probe compound is compound 54. In certain embodiments, the probe compound is 73. In certain embodiments, the probe compound is compound 74.

It will be appreciated that many -T¹-R' reagents are commercially available.

In some embodiments, the present invention provides a method for determining occupancy of a protein kinase by a provided irreversible inhibitor (i.e., a compound of any of the formulae presented herein) in a patient, comprising providing one or more tissues, cell types, or a lysate thereof, obtained from a patient administered at least one dose of a compound of said irreversible inhibitor, contacting said tissue, cell type or lysate thereof with a probe compound (i.e., a compound of formula I-t or formula I-s) to covalent modify at least one protein kinase present in said lysate, and measuring the amount of said protein kinase covalently modified by the probe compound to determine occupancy of said protein kinase by said inhibitor as compared to occupancy of said protein kinase by said probe compound. In certain embodiments, the method further comprises the step of adjusting the dose of the compound of formulae presented herein to increase occupancy of the protein kinase. In certain other embodiments, the method further comprises the step of adjusting the dose of the compound of formulae presented herein to decrease occupancy of the protein kinase.

As used herein, the terms "occupancy" or "occupy" refer to the extent to which a protein kinase is modified by a provided covalent inhibitor compound. One of ordinary skill in the art would appreciate that it is desirable to administer the lowest dose possible to achieve the desired efficacious occupancy of the protein kinase.

In some embodiments, the protein kinase to be modified is BTK.

In some embodiments, the probe compound comprises the irreversible inhibitor for which occupancy is being determined.

In some embodiments, the present invention provides a method for assessing the efficacy of a provided irreversible inhibitor in a mammal, comprising administering a provided irreversible inhibitor to the mammal, administering a provided probe compound to tissues or cells isolated from the mammal, or a lysate thereof, measuring the activity of the detectable moiety of the probe compound, and comparing the activity of the detectable moiety to a standard.

In other embodiments, the present invention provides a method for assessing the pharmacodynamics of a provided irreversible inhibitor in a mammal, comprising administering a provided irreversible inhibitor to the mammal, administering a probe compound presented herein to one or more cell types, or a lysate thereof, isolated from the mammal, and measuring the activity of the detectable moiety of the probe compound at different time points following the administration of the inhibitor.

In yet other embodiments, the present invention provides a method for in vitro labeling of a protein kinase comprising contacting said protein kinase with a probe compound described herein. In one embodiment, the contacting step comprises incubating the protein kinase with a probe compound presented herein.

In certain embodiments, the present invention provides a method for in vitro labeling of a protein kinase comprising contacting one or more cells or tissues, or a lysate thereof, expressing the protein kinase with a probe compound described herein.

In certain other embodiments, the present invention provides a method for detecting a labeled protein kinase comprising separating proteins, the proteins comprising a protein kinase labeled by probe compound described herein, by electrophoresis and detecting the probe compound by fluorescence.

In some embodiments, the present invention provides a method for assessing the pharmacodynamics of a provided irreversible inhibitor in vitro, comprising incubating the provided irreversible inhibitor with the target protein kinase, adding the probe compound presented herein to the target protein kinase, and determining the amount of target modified by the probe compound.

In some embodiments, the probe is detected by sodium dodecyl sulfate polyacrylamide gel electrophoresis (SDS-PAGE). In other embodiments, the probe is detected by ELISA. In certain embodiments, the probe is detected by flow cytometry.

In other embodiments, the present invention provides a method for probing the kinome with irreversible inhibitors comprising incubating one or more cell types, or a lysate thereof, with a biotinylated probe compound to generate proteins modified with a biotin moiety, digesting the proteins, capturing with avidin or an analog thereof, and performing multi-dimensional LC-MS-MS to identify protein kinases modified by the probe compound and the adduction sites of said kinases.

In certain embodiments, the present invention provides a method for measuring protein synthesis in cells comprising incubating cells with an irreversible inhibitor of the target protein, forming lysates of the cells at specific time points, and incubating said cell lysates with an inventive probe compound to measure the appearance of free protein over an extended period of time.

In other embodiments, the present invention provides a method for determining a dosing schedule in a mammal for maximizing occupancy of a target protein kinase comprising assaying a one or more cell types, or a lysate thereof, isolated from the mammal, (derived from, e.g., splenocytes, peripheral B cells, whole blood, lymph nodes, intestinal tissue, or other tissues) from a mammal administered a provided irreversible inhibitor of any of the formulae presented herein, wherein the assaying step comprises contacting said one or more tissues, cell types, or a lysate thereof, with a provided probe compound and measuring the amount of protein kinase covalently modified by the probe compound.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Compound numbers utilized in the Examples below correspond to compound numbers set forth supra.

¹H NMR was recorded on a Bruker 400 MHz spectrometer, using residual signal of deuterated solvent as internal reference. Chemical shifts (δ) are reported in ppm relative to the residual solvent signal (δ=2.49 ppm for 1H NMR in DMSO-d6). 1H NMR data are reported as follows: chemical shift (multiplicity, coupling constants, and number of hydrogens). Multiplicity is abbreviated as follows: s (singlet), d (doublet), t (triplet), q (quartet), m (multiplet), br (broad).

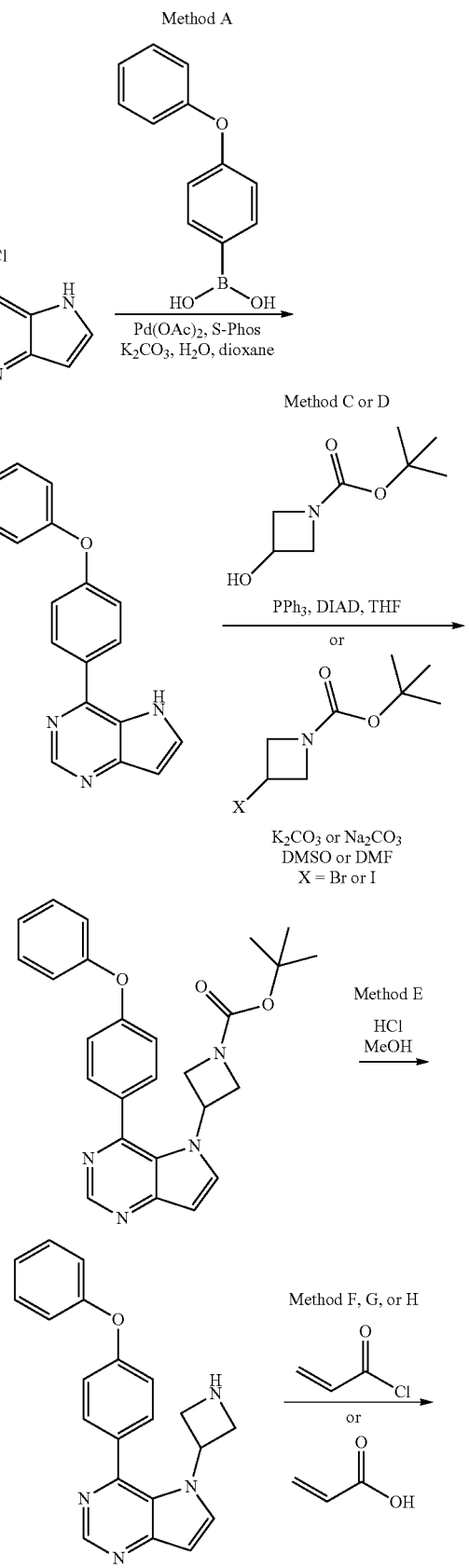

91
-continued
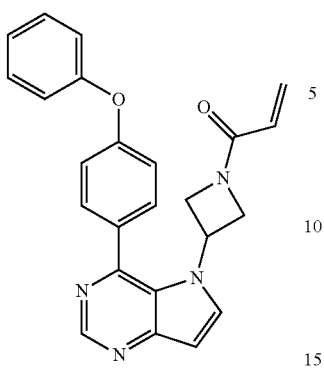
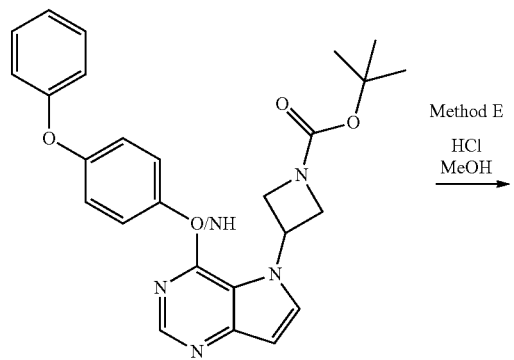
Scheme 2
Method B
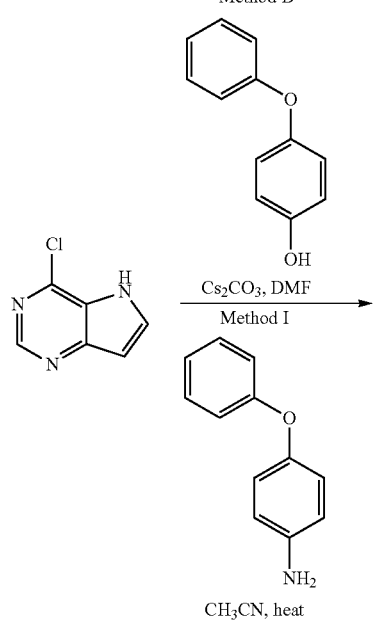
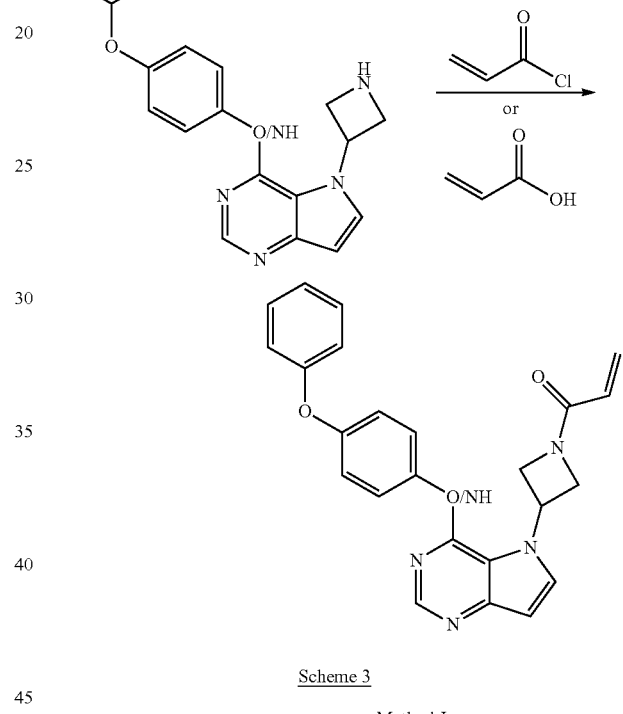
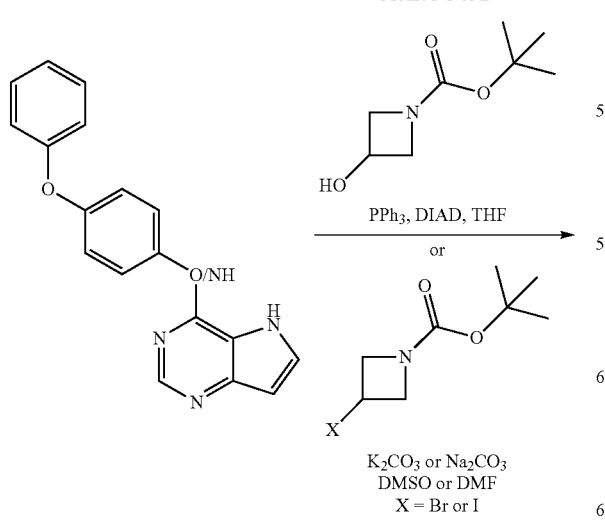
Scheme 3
Method J
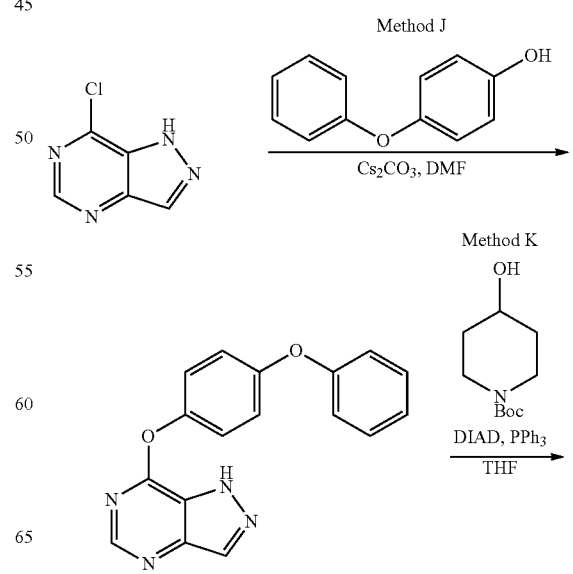

93

-continued

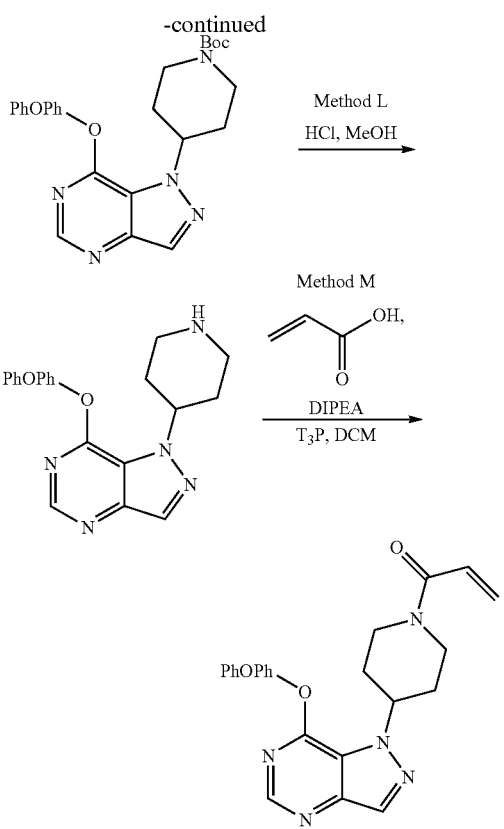

Example 1

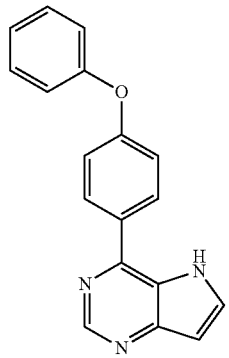 [SMILES: c1ccc(Oc2ccc(-c3ncnc4cc[nH]c34)cc2)cc1]

4-(4-phenoxyphenyl)-5H-pyrrolo[3,2-d]pyrimidine
(Method A)

Into a 20-mL vial was placed 4-chloro-5H-pyrrolo[3,2-d]
pyrimidine (250.00 mg; 1.63 mmol), (4-phenoxyphenyl)
boronic acid (522.64 mg: 2.44 mmol), palladium acetate
(18.27 mg; 0.08 mmol), 2-dicyclohexylphosphino-2',6'-di-
methoxybiphenyl (66.83 mg; 0.16 mmol), potassium car-
bonate (674.97 mg; 0.16 mmol) suspended in dioxane (3.00
ml) and water (0.30 ml). The reaction mixture was heated at
150° C. for 3 hours. The reaction mixture was allowed to
cool to rt. The crude mixture was purified using flash column
chromatography. Fractions containing the desired product
were combined and concentrated under reduced pressure.
The product was then lyophilized overnight to afford 4-(4-
phenoxyphenyl)-5H-pyrrolo[3,2-d]pyrimidine (422.40 mg,
90% yield) as a yellow solid. MS: m/z=288 [M+H]$^+$.

94

Example 2

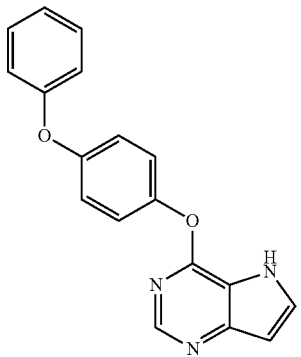 [SMILES: c1ccc(Oc2ccc(Oc3ncnc4cc[nH]c34)cc2)cc1]

4-(4-phenoxyphenoxy)-5H-pyrrolo[3,2-d]pyrimidine
(Method B)

Into a 20-mL vial was placed 4-chloro-5H-pyrrolo[3,2-d]
pyrimidine (500.00 mg; 3.26 mmol), cesium carbonate (3.18
g: 9.77 mmol), and 4-phenoxyphenol (909.40 mg; 4.88
mmol) suspended in DMF (6.00 ml). The reaction mixture
was heated at 160° C. for 3 hours. The reaction mixture was
allowed to cool to rt. The mixture was purified using flash
column chromatography. Fractions containing the desired
product were combined and concentrated under reduced
pressure. The product was then lyophilized overnight to
afford 4-(4-phenoxyphenoxy)-5H-pyrrolo[3,2-d]pyrimidine
(611.4 mg, 62% yield) as a yellow solid. MS: m/z=288
[M+H]$^+$.

Example 3

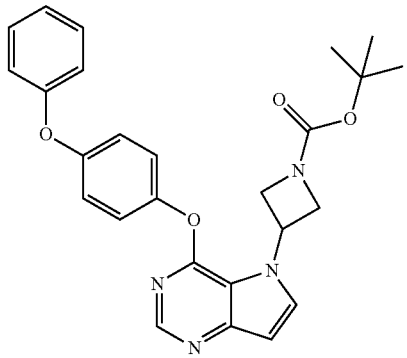 [SMILES: CC(C)(C)OC(=O)N1CC(n2ccc3ncnc(Oc4ccc(Oc5ccccc5)cc4)c32)C1]

tert-butyl 3-(4-(4-phenoxyphenoxy)-5H-pyrrolo[3,2-
d]pyrimidin-5-yl)azetidine-1-carboxylate (Method
C)

Into a 20-mL vial was placed 4-(4-phenoxyphenoxy)-5H-
pyrrolo[3,2-d]pyrimidine (200.00 mg; 0.66 mmol.), tert-
butyl 3-hydroxyazetidine-1-carboxylate (456.85 mg; 2.64
mmol), triphenylphosphine (1.04 g; 3.96 mmol), and diiso-
propyl azodicarboxylate (800.00 mg; 3.96 mmol) suspended
in THF (4.00 ml). The reaction mixture was heated at 40 OC
overnight. The reaction mixture was allowed to cool to rt.
The crude mixture was purified using flash column chroma-
tography. Fractions containing the desired product were
combined and concentrated under reduced pressure. The
mixture was then purified using preparative HPLC. Frac-
tions containing the desired product were combined and
lyophilized overnight to afford tert-butyl 3-(4-(4-phenoxy-
phenoxy)-5H-pyrrolo[3,2-d]pyrimidin-5-yl)azetidine-1-carboxylate (TFA salt, 188.00 mg, 50% yield) as a yellow solid. MS: m/z=459 [M+H]+.

Example 4

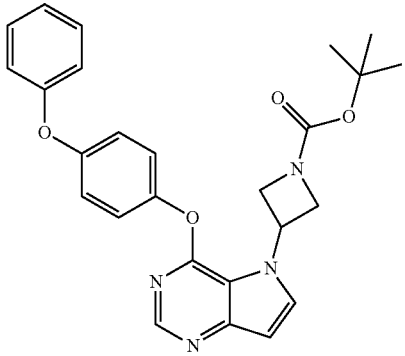 [SMILES: CC(C)(C)OC(=O)N1CC(n2ccc3ncnc(Oc4ccc(Oc5ccccc5)cc4)c32)C1]

tert-butyl 3-(4-(4-phenoxyphenoxy)-5H-pyrrolo[3,2-d]pyrimidin-5-yl)azetidine-1-carboxylate (Method D)

Into a 20-mL vial was placed 4-(4-phenoxyphenoxy)-5H-pyrrolo[3,2-d]pyrimidine (600.00 mg; 1.98 mmol), tert-butyl 3-bromoazetidine-1-carboxylate (934.10 mg, 3.96 mmol), and sodium tert-butoxide (760.42 mg, 7.91 mmol) suspended in DMF (8.00 ml). The reaction mixture was heated to 100° C. for 2 days. The reaction mixture was purified using flash column chromatography. Fractions containing the desired product were combined and concentrated under reduced pressured. The product was then lyophilized overnight to afford tert-butyl 3-(4-(4-phenoxyphenoxy)-5H-pyrrolo[3,2-d]pyrimidin-5-yl)azetidine-1-carboxylate (918.00 mg, 100% yield) as a yellow, viscous liquid. MS: m/z=459 [M+H]+.

Example 5

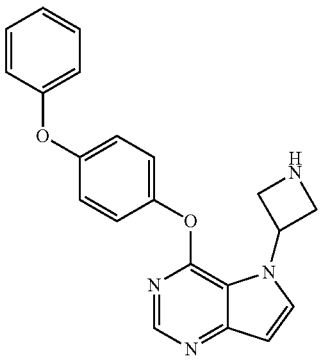 [SMILES: c1ccc(Oc2ccc(Oc3ncnc4ccn(C5CNC5)c34)cc2)cc1]

5-(azetidin-3-yl)-4-(4-phenoxyphenoxy)-5H-pyrrolo[3,2-d]pyrimidine (Method E)

Into a 20-mL vial was placed tert-butyl 3-(4-(4-phenoxyphenoxy)-5H-pyrrolo[3,2-d]pyrimidin-5-yl)azetidine-1-carboxylate (910.00 mg; 1.98 mmol) dissolved in methanol (5.00 ml). Hydrogen chloride (2.0 M solution in Et₂O) (4.96 ml) was added to the mixture. The reaction mixture was stirred at rt overnight. The reaction mixture was concentrated under reduced pressured and subsequently lyophilized overnight to afford 5-(azetidin-3-yl)-4-(4-phenoxyphenoxy)-5H-pyrrolo[3,2-d]pyrimidine as a yellow solid crude. MS: m/z=359 [M+H]+.

Example 6

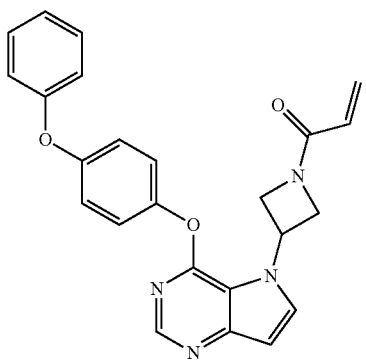

1-(3-(4-(4-phenoxyphenoxy)-5H-pyrrolo[3,2-d]pyrimidin-5-yl)azetidin-1-yl)prop-2-en-1-one (3) (Method F)

Into a 20-mL vial was added 5-(azetidin-3-yl)-4-(4-phenoxyphenoxy)-5H-pyrrolo[3,2-d]pyrimidine (15.00 mg; 0.04 mmol), sodium bicarbonate (10.55 mg; 0.13 mmol) suspended in THF (2.00 ml) and water (0.20 ml). Acryloyl chloride (0.01 ml; 0.06 mmol) was added. The reaction mixture was stirred at rt overnight. The crude mixture waspurified using flash column chromatography. Fractions containing the desired product were combined and concentrated under reduced pressure. The material was then purified using preparative HPLC. Fractions containing the desired product were combined and lyophilized overnight to afford 1-(3-(4-(4-phenoxyphenoxy)-5H-pyrrolo[3,2-d]pyrimidin-5-yl)azetidin-1-yl)prop-2-en-1-one (TFA salt, 12.00 mg, 55% yield) as a white solid. HPLC: 85%, RT=3.749 min. MS: m/z=413 [M+H]+, RT=2.553 min. ¹H-NMR (DMSO-D6) δ 8.38 (s, 1H), 8.20 (d, 1H), 7.42 (t, 2H), 7.34 (d, 2H), 7.15 (t, 1H), 7.09 (d, 2H), 7.05 (d, 2H), 6.74 (d, 1H), 6.32 (dd, 1H), 6.06 (d, 1H), 5.79 (m, 1H), 5.65 (d, 1H), 4.78 (t, 1H), 4.08 (m, 1H), 4.50-4.40 (m, 2H).

Example 7

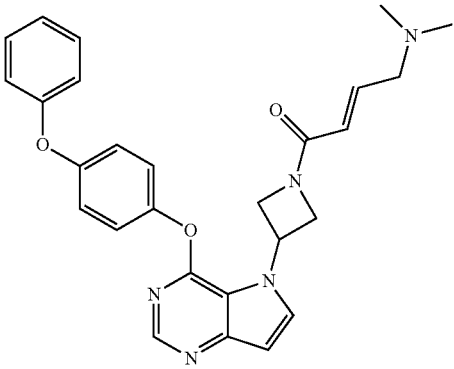 [SMILES: CN(C)C/C=C/C(=O)N1CC(n2ccc3ncnc(Oc4ccc(Oc5ccccc5)cc4)c32)C1]

(E)-4-(dimethylamino)-1-(3-(4-(4-phenoxyphenoxy)-5H-pyrrolo[3,2-d]pyrimidin-5-yl)azetidin-1-yl)but-2-en-1-one (19) (Method G)

Into a 20-mL vial was added (E)-4-(dimethylamino)but-2-enoic acid (78.50 mg; 0.61 mmol), and bis(2-oxo-3-oxazolidinyl)phosphinic chloride (232.09 mg; 0.91 mmol), and N,N-diisopropylethylamine (0.21 ml; 1.22 mmol) suspended in dioxane (3.00 ml). The reaction mixture was stirred at rt for 1 h. 5-(azetidin-3-yl)-4-(4-phenoxyphenoxy)-

5H-pyrrolo[3,2-d]pyrimidine (120.00 mg; 0.30 mmol) was then added. The reaction mixture was stirred at rt overnight. The crude mixture was purified using flash column chromatography. Fractions containing the desired product were combined and concentrated under reduced pressure. The residue was then purified using preparative HPLC. Fractions containing the desired product were combined and lyophilized overnight to afford (E)-4-(dimethylamino)-1-(3-(4-(4-phenoxyphenoxy)-5H-pyrrolo[3,2-d]pyrimidin-5-yl)azetidin-1-yl)but-2-en-1-one (69.00 mg, 48% yield) as a white solid. HPLC: 95%, RT=2.879 min. MS: m/z=470 [M+H]+, RT=2.016 min. $^1$H-NMR (DMSO-D6) δ 8.37 (s, 1H), 8.18 (d, 1H), 7.43 (t, 2H), 7.34 (d, 2H), 7.19-7.04 (m, 5H), 6.74 (d, 1H), 6.54 (doublet of triplet, 1H), 6.11 (d, 1H), 5.78 (m, 1H), 4.79-4.66 (m, 2H), 4.49-4.38 (m, 2H), 2.98 (d, 2H), 2.12 (s, 6H).

Example 8

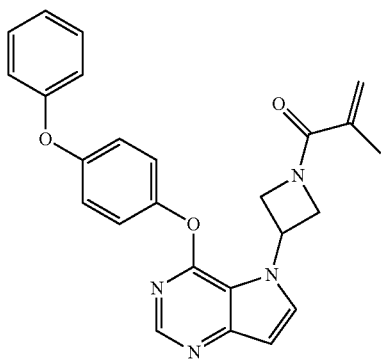 [SMILES: C=C(C)C(=O)N1CC(n2ccc3ncnc(Oc4ccc(Oc5ccccc5)cc4)c32)C1]

2-methyl-1-(3-(4-(4-phenoxyphenoxy)-5H-pyrrolo[3,2-d]pyrimidin-5-yl)azetidin-1-yl)prop-2-en-1-one (51) (Method H)

Into a 20-mL vial was added 5-(azetidin-3-yl)-4-(4-phenoxyphenoxy)-5H-pyrrolo[3,2-d]pyrimidine (70.00 mg, 0.18 mmol), methacrylic acid (30.52 mg, 0.35 mmol), 2,4,6-tripropyl-1,3,5,2,4,6-trioxatriphosphinane 2,4,6-trioxide (338.44 mg, 0.53 mmol), N,N-diisopropylethylamine (0.09 ml, 0.53 mmol) suspended in DCM (3 mL). The mixture was stirred at rt for 3 hours. The crude mixture was purified using flash column chromatography. The fractions containing the desired product were combined and concentrated under reduced pressure. The material was then purified using preparative HPLC. Fractions containing the desired product were combined and lyophilized overnight to afford 2-methyl-1-(3-(4-(4-phenoxyphenoxy)-5H-pyrrolo[3,2-d]pyrimidin-5-yl)azetidin-1-yl)prop-2-en-1-one (20.00 mg, 26% yield) as a white solid. HPLC: 93%, RT=3.838 min. MS: m/z=427 [M+H]+, RT=2.732 min.

Example 9

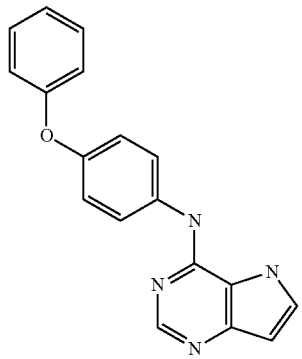 [SMILES: c1ccc(Oc2ccc(Nc3ncnc4cc[nH]c34)cc2)cc1]

N-(4-phenoxyphenyl)-5H-pyrrolo[3,2-d]pyrimidin-4-amine (Method I)

Into a 20-mL vial was placed 4-chloro-5H-pyrrolo[3,2-d]pyrimidine (250.00 mg; 1.63 mmol), and 4-phenoxyaniline (452.29 mg; 2.44 mmol) suspended in acetonitrile (3.00 ml). The reaction mixture was heated at 100 ºC overnight. The murky reaction mixture was allowed to cool to rt. The solid was filtered and washed with acetonitrile. The solid was dried under vacuum to afford N-(4-phenoxyphenyl)-5H-pyrrolo[3,2-d]pyrimidin-4-amine (580.00 mg, 100% yield) as a yellow solid. MS: m/z=303 [M+H]+.

Example 10

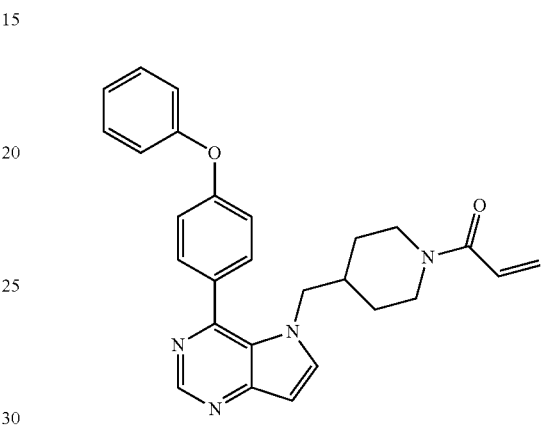

1-(4-((4-(4-phenoxyphenyl)-5H-pyrrolo[3,2-d]pyrimidin-5-yl)methyl)piperidin-1-yl)prop-2-en-1-one (47)

1-(4-((4-(4-phenoxyphenyl)-5H-pyrrolo[3,2-d]pyrimidin-5-yl)methyl)piperidin-1-yl)prop-2-en-1-one was prepared from 4-chloro-5H-pyrrolo[3,2-d]pyrimidine, (4-phenoxyphenyl)boronic acid, tert-butyl 4-(hydroxymethyl)piperidine-1-carboxylate, and acryloyl chloride using procedures similar to those described in methods A, C, E and F. HPLC: 96%. MS: m/z=439 [M+H]+. $^1$H-NMR (DMSO-D6) δ 8.91 (s, 1H), 8.00 (d, 1H), 7.70 (d, 2H), 7.48 (t, 2H), 7.25-7.19 (m, 3H), 7.11 (d, 1H), 6.77-6.69 (m, 2H), 6.04 (d, 1H), 5.62 (d, 1H), 4.25 (d, 1H), 3.93-3.87 (m, 3H), 2.68 (m, 1H), 2.30 (m, 1H), 1.34 (m, 1H), 0.92-0.75 (m, 4H).

Example 11

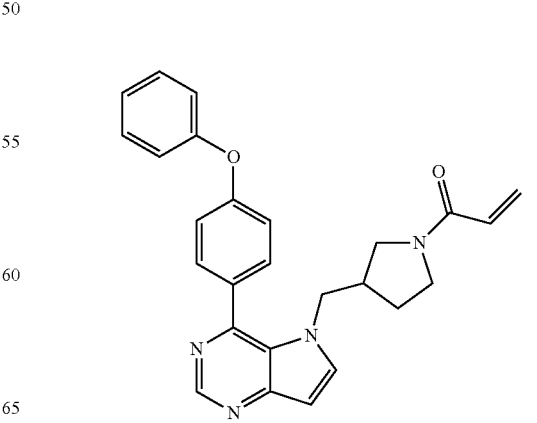

1-(3-((4-(4-phenoxyphenyl)-5H-pyrrolo[3,2-d]pyrimidin-5-yl)methyl)pyrrolidin-1-yl)prop-2-en-1-one (46)

1-(3-((4-(4-phenoxyphenyl)-5H-pyrrolo[3,2-d]pyrimidin-5-yl)methyl)pyrrolidin-1-yl)prop-2-en-1-one was prepared from 4-chloro-5H-pyrrolo[3,2-d]pyrimidine, (4-phenoxyphenyl)boronic acid, tert-butyl 3-(hydroxymethyl)pyrrolidine-1-carboxylate, and acryloyl chloride using procedures similar to those described in methods A, C, E, and F. HPLC: 96%. MS: m/z=425 [M+H]$^+$.

Example 12

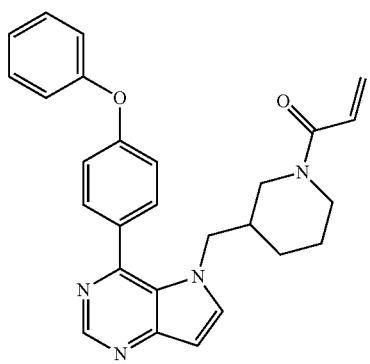 [SMILES: C=CC(=O)N1CCCC(Cn2ccc3ncnc(-c4ccc(Oc5ccccc5)cc4)c32)C1]

1-(3-((4-(4-phenoxyphenyl)-5H-pyrrolo[3,2-d]pyrimidin-5-yl)methyl)piperidin-1-yl)prop-2-en-1-one (48)

1-(3-((4-(4-phenoxyphenyl)-5H-pyrrolo[3,2-d]pyrimidin-5-yl)methyl)piperidin-1-yl)prop-2-en-1-one was prepared from 4-chloro-5H-pyrrolo[3,2-d]pyrimidine, (4-phenoxyphenyl)boronic acid, tert-butyl 3-(hydroxymethyl)piperidine-1-carboxylate, and acryloyl chloride using procedures similar to those described in methods A, C, E and F. HPLC: 94%. MS: m/z=439 [M+H]$^+$.

Example 13

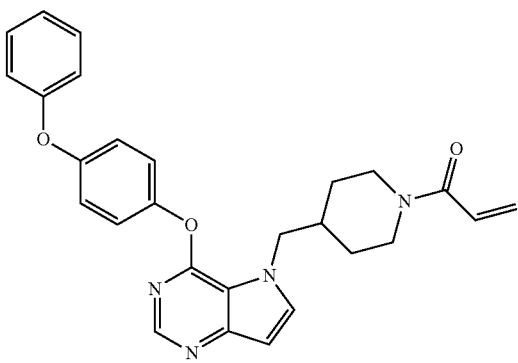 [SMILES: C=CC(=O)N1CCC(Cn2ccc3ncnc(Oc4ccc(Oc5ccccc5)cc4)c32)CC1]

1-(4-((4-(4-phenoxyphenoxy)-5H-pyrrolo[3,2-d]pyrimidin-5-yl)methyl)piperidin-1-yl)prop-2-en-1-one (37)

1-(4-((4-(4-phenoxyphenoxy)-5H-pyrrolo[3,2-d]pyrimidin-5-yl)methyl)piperidin-1-yl)prop-2-en-1-one was prepared from 4-chloro-5H-pyrrolo[3,2-d]pyrimidine, 4-phenoxyphenol, tert-butyl 4-(hydroxymethyl)piperidine-1-carboxylate, and acryloyl chloride using procedures similar to those described in methods B, C, E and F. HPLC: 99%. MS: m/z=455 [M+H]$^+$. $^1$H-NMR (DMSO-D6) δ 8.40 (s, 1H), 7.89 (d, 1H), 7.44 (t, 2H), 7.36 (d, 2H), 7.22-7.07 (m, 5H), 6.78 (dd, 1H), 6.67 (d, 1H), 6.07 (d, 1H), 5.64 (d, 1H), 4.43-4.36 (m, 3H), 4.05 (d, 1H), 3.00 (t, 1H), 2.59 (t, 1H), 2.21 (m, 1H), 1.59-1.47 (m, 2H), 1.26-1.09 (m, 2H).

Example 14

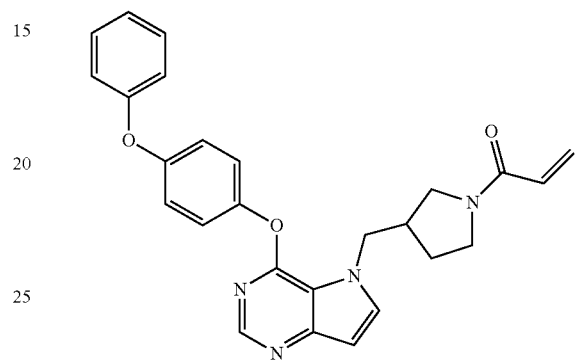

1-(3-((4-(4-phenoxyphenoxy)-5H-pyrrolo[3,2-d]pyrimidin-5-yl)methyl)pyrrolidin-1-yl)prop-2-en-1-one (29)

1-(3-((4-(4-phenoxyphenoxy)-5H-pyrrolo[3,2-d]pyrimidin-5-yl)methyl)pyrrolidin-1-yl)prop-2-en-1-one was prepared from 4-chloro-5H-pyrrolo[3,2-d]pyrimidine, 4-phenoxyphenol, tert-butyl 3-(hydroxymethyl)pyrrolidine-1-carboxylate, and acryloyl chloride using procedures similar to those described in methods B, C, E and F. HPLC: 94%. MS: m/z=441 [M+H]$^+$.

Example 15

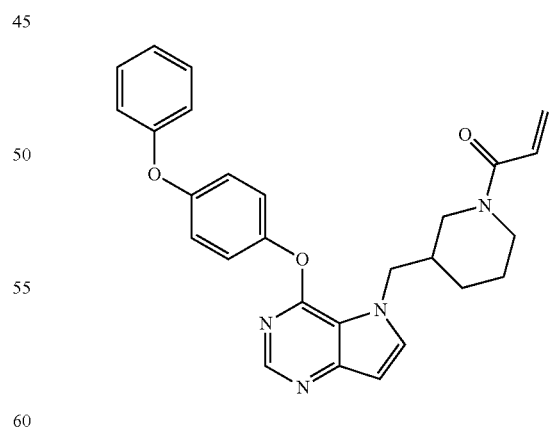

1-(3-((4-(4-phenoxyphenoxy)-5H-pyrrolo[3,2-d]pyrimidin-5-yl)methyl)piperidin-1-yl)prop-2-en-1-one (15)

1-(3-((4-(4-phenoxyphenoxy)-5H-pyrrolo[3,2-d]pyrimidin-5-yl)methyl)piperidin-1-yl)prop-2-en-1-one was prepared from 4-chloro-5H-pyrrolo[3,2-d]pyrimidine, 4-phenoxyphenol, tert-butyl 3-(hydroxymethyl)piperidine-1-carboxylate, and acryloyl chloride using procedures similar to those described in methods B, C, E, and F. HPLC: 86%. MS: m/z=455 [M+H]⁺.

Example 16

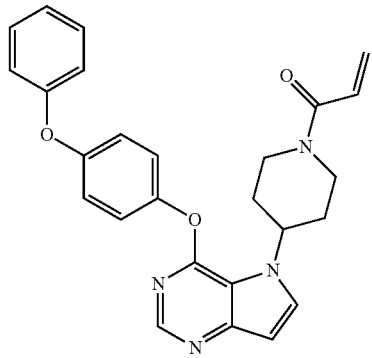 [SMILES: C=CC(=O)N1CCC(n2ccc3ncnc(Oc4ccc(Oc5ccccc5)cc4)c32)CC1]

1-(4-(4-(4-phenoxypheny)-5H-pyrrolo[3,2-d]pyrimidin-5-yl)piperidin-1-yl)prop-2-en-1-one (2)

1-(4-(4-(4-phenoxyphenoxy)-5H-pyrrolo[3,2-d]pyrimidin-5-yl)piperidin-1-yl)prop-2-en-1-one was prepared from 4-chloro-5H-pyrrolo[3,2-d]pyrimidine, 4-phenoxyphenol, tert-butyl 4-hydroxypiperidine-1-carboxylate, and acryloyl chloride using procedures similar to those described in methods B, C, E, and F. HPLC: 98%. MS: m/z=441 [M+H]⁺.

Example 17

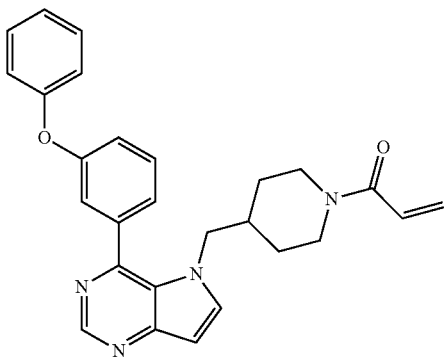 [SMILES: C=CC(=O)N1CCC(Cn2ccc3ncnc(-c4cccc(Oc5ccccc5)c4)c32)CC1]

1-(4-((4-(3-phenoxyphenyl)-5H-pyrrolo[3,2-d]pyrimidin-5-yl)methyl)piperidin-1-yl)prop-2-en-1-one (45)

1-(4-((4-(3-phenoxyphenyl)-5H-pyrrolo[3,2-d]pyrimidin-5-yl)methyl)piperidin-1-yl)prop-2-en-1-one was prepared from 4-chloro-5H-pyrrolo[3,2-d]pyrimidine, (3-phenoxyphenyl)boronic acid, tert-butyl 4-(hydroxymethyl)piperidine-1-carboxylate, and acryloyl chloride using procedures similar to those described in methods A, C, E, and F. HPLC: 98%. MS: m/z=439 [M+H]⁺. ¹H-NMR (DMSO-D6) δ 8.92 (s, 1H), 8.03 (d, 1H), 7.61 (t, 1H), 7.47-7.42 (m, 3H), 7.27-7.24 (m, 2H), 7.20 (t, 1H), 7.09 (d, 2H), 6.78 (d, 1H), 6.72 (dd, 1H), 6.05 (d, 1H), 5.63 (d, 1H), 4.26 (d, 1H), 3.95-3.85 (m, 3H), 2.70 (m, 1H), 2.30 (m, 1H), 1.40 (m, 1H), 0.94-0.75 (m, 4H).

Example 18

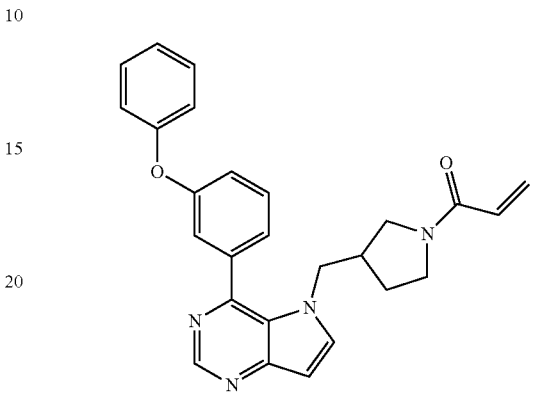

1-(3-((4-(3-phenoxyphenyl)-5H-pyrrolo[3,2-d]pyrimidin-5-yl)methyl)pyrrolidin-1-yl)prop-2-en-1-one (40)

1-(3-((4-(3-phenoxyphenyl)-5H-pyrrolo[3,2-d]pyrimidin-5-yl)methyl)pyrrolidin-1-yl)prop-2-en-1-one was prepared from 4-chloro-5H-pyrrolo[3,2-d]pyrimidine, (3-phenoxyphenyl)boronic acid, tert-butyl 3-(hydroxymethyl)pyrrolidine-1-carboxylate, and acryloyl chloride using procedures similar to those described in methods A, C, E, and F. HPLC: 90%. MS: m/z=425 [M+H]⁺.

Example 19

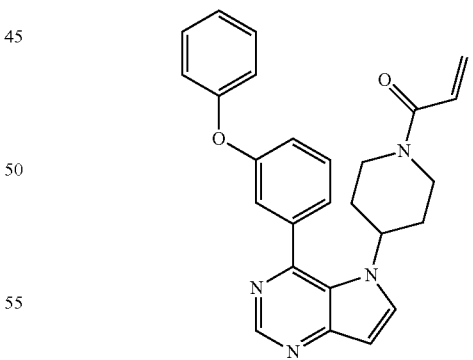

1-(4-(4-(3-phenoxyphenyl)-5H-pyrrolo[3,2-d]pyrimidin-5-yl)piperidin-1-yl)prop-2-en-1-one (50)

1-(4-(4-(3-phenoxyphenyl)-5H-pyrrolo[3,2-d]pyrimidin-5-yl)piperidin-1-yl)prop-2-en-1-one was prepared from 4-chloro-5H-pyrrolo[3,2-d]pyrimidine, (3-phenoxyphenyl)boronic acid, tert-butyl 4-hydroxypiperidine-1-carboxylate, and acryloylchloride using procedures similar to those described in methods A, C, E and F. HPLC: 100%. MS: m/z=425 [M+H]+.

Example 20

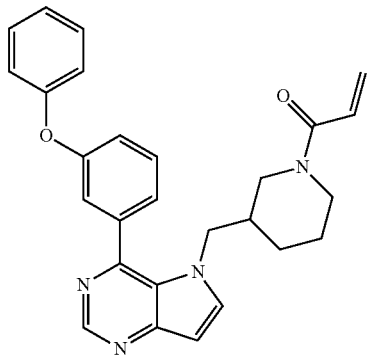 [SMILES: C=CC(=O)N1CCCC(Cn2ccc3ncnc(-c4cccc(Oc5ccccc5)c4)c32)C1]

1-(3-((4-(3-phenoxyphenyl)-5H-pyrrolo[3,2-d]pyrimidin-5-yl)methyl)piperidin-1-yl)prop-2-en-1-one (44)

1-(3-((4-(3-phenoxyphenyl)-5H-pyrrolo[3,2-d]pyrimidin-5-yl)methyl)piperidin-1-yl)prop-2-en-1-one was prepared from 4-chloro-5H-pyrrolo[3,2-d]pyrimidine, (3-phenoxyphenyl)boronic acid, tert-butyl 3-(hydroxymethyl)piperidine-1-carboxylate, and acryloyl chloride using procedures similar to those described in methods A, C, E, and F. HPLC: 98%. MS: m/z=439 [M+H]+.

Example 21

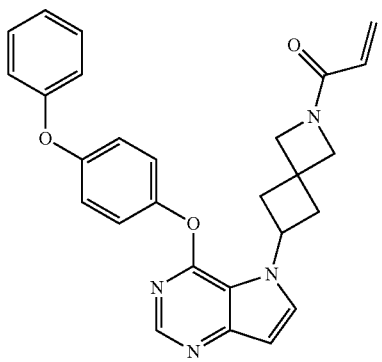 [SMILES: C=CC(=O)N1CC2(CC(n3ccc4ncnc(Oc5ccc(Oc6ccccc6)cc5)c43)C2)C1]

1-(6-(4-(4-phenoxyphenoxy)-5H-pyrrolo[3,2-d]pyrimidin-5-yl)-2-azaspiro[3.3]heptan-2-yl)prop-2-en-1-one (28)

1-(6-(4-(4-phenoxyphenoxy)-5H-pyrrolo[3,2-d]pyrimidin-5-yl)-2-azaspiro[3.3]heptan-2-yl)prop-2-en-1-one was prepared from 4-chloro-5H-pyrrolo[3,2-d]pyrimidine, 4-phenoxyphenol, tert-butyl 6-hydroxy-2-azaspiro[3.3]heptane-2-carboxylate, and acryloyl chloride using procedures similar to those described in methods B, C, E, and F. HPLC: 92%. MS: m/z=453 [M+H]+. 1H-NMR (DMSO-D6) δ 8.35 (s, 1H), 8.09 (d, 1H), 7.44 (t, 2H), 7.36 (d, 2H), 7.19-7.07 (m, 5H), 6.69 (d, 1H), 6.33-6.23 (m, 1H), 6.08 (d, 1H), 5.66 (d, 1H), 5.27 (m, 1H), 4.38 (s, 1H), 4.22 (s, 1H), 4.08 (s, 1H), 3.92 (s, 1H), 2.90-2.77 (m, 4H).

Example 22

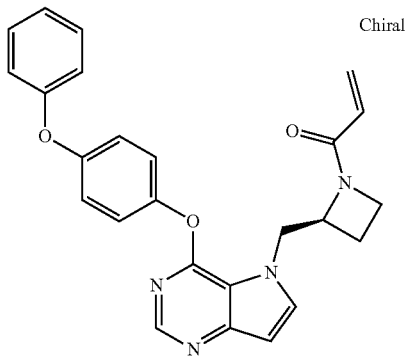 [SMILES: C=CC(=O)N1CC[C@H]1Cn1ccc2ncnc(Oc3ccc(Oc4ccccc4)cc3)c21]

(S)-1-(2-((4-(4-phenoxyphenoxy)-5H-pyrrolo[3,2-d]pyrimidin-5-yl)methyl)azetidin-1-yl)prop-2-en-1-one (25)

(S)-1-(2-((4-(4-phenoxyphenoxy)-5H-pyrrolo[3,2-d]pyrimidin-5-yl)methyl)azetidin-1-yl)prop-2-en-1-one was prepared from 4-chloro-5H-pyrrolo[3,2-d]pyrimidine, 4-phenoxyphenol, (S)-tert-butyl 2-(hydroxymethyl)azetidine-1-carboxylate, and acryloyl chloride using procedures similar to those described in methods B, C, E, and F. HPLC: 80%. MS: m/z=427 [M+H]+.

Example 23

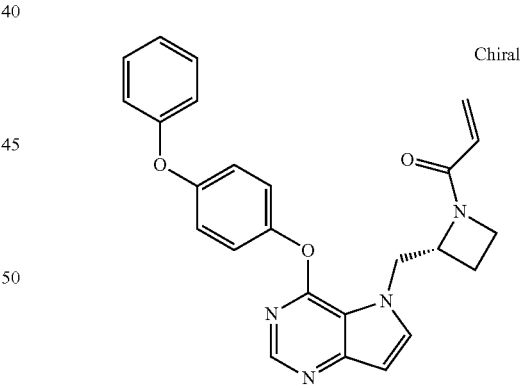

(R)-1-(2-((4-(4-phenoxyphenoxy)-5H-pyrrolo[3,2-d]pyrimidin-5-yl)methyl)azetidin-1-yl)prop-2-en-1-one (9)

(R)-1-(2-((4-(4-phenoxyphenoxy)-5H-pyrrolo[3,2-d]pyrimidin-5-yl)methyl)azetidin-1-yl)prop-2-en-1-one was prepared from 4-chloro-5H-pyrrolo[3,2-d]pyrimidine, 4-phenoxyphenol, (R)-tert-butyl 2-(hydroxymethyl)azetidine-1-carboxylate, and acryloyl chloride using procedures similar to those described in methods B, C, E, and F. HPLC: 84%. MS: m/z=427 [M+H]+.

Example 24

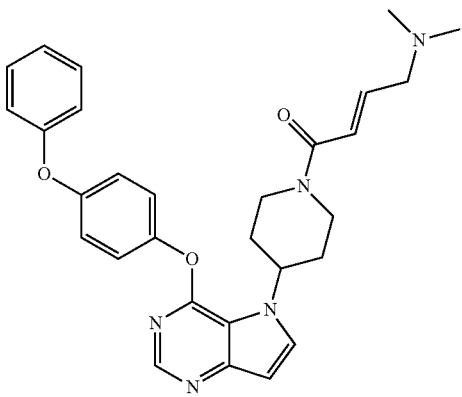 [SMILES: CN(C)C/C=C/C(=O)N1CCC(n2ccc3ncnc(Oc4ccc(Oc5ccccc5)cc4)c32)CC1]

(E)-4-(dimethylamino)-1-(4-(4-(4-phenoxyphenoxy)-5H-pyrrolo[3,2-d]pyrimidin-5-yl)piperidin-1-yl)but-2-en-1-one (1)

(E)-4-(dimethylamino)-1-(4-(4-(4-phenoxyphenoxy)-5H-pyrrolo[3,2-d]pyrimidin-5-yl)piperidin-1-yl)but-2-en-1-one was prepared from 4-chloro-5H-pyrrolo[3,2-d]pyrimidine, 4-phenoxyphenol, tert-butyl 4-hydroxypiperidine-1-carboxylate, and (E)-4-(dimethylamino)but-2-enoic acid using procedures similar to those described in methods B, C, E, and G. HPLC: 99%. MS: m/z=498 [M+H]$^+$.

Example 25

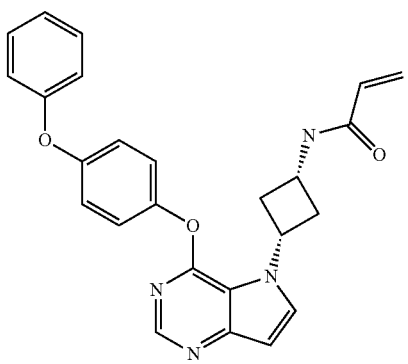 [SMILES: C=CC(=O)N[C@H]1C[C@@H](n2ccc3ncnc(Oc4ccc(Oc5ccccc5)cc4)c32)C1]

N-(cis-3-(4-(4-phenoxyphenoxy)-5H-pyrrolo[3,2-d]pyrimidin-5-yl)cyclobutyl)acrylamide (10)

N-(cis-3-(4-(4-phenoxyphenoxy)-5H-pyrrolo[3,2-d]pyrimidin-5-yl)cyclobutyl)acrylamide was prepared from 4-chloro-5H-pyrrolo[3,2-d]pyrimidine, 4-phenoxyphenol, tert-butyl(trans-3-hydroxycyclobutyl)carbamate, and acryloyl chloride using procedures similar to those described in methods B, C, E, and F. HPLC: 99%. MS: m/z=427 [M+H]$^+$.

Example 26

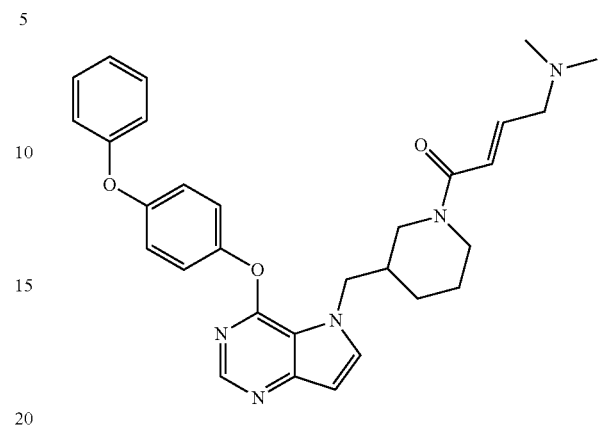

(E)-4-(dimethylamino)-1-(3-((4-(4-phenoxyphenoxy)-5H-pyrrolo[3,2-d]pyrimidin-5-yl)methyl)piperidin-1-yl)but-2-en-1-one (30)

(E)-4-(dimethylamino)-1-(3-((4-(4-phenoxyphenoxy)-5H-pyrrolo[3,2-d]pyrimidin-5-yl)methyl)piperidin-1-yl)but-2-en-1-one was prepared from 4-chloro-5H-pyrrolo[3,2-d]pyrimidine, 4-phenoxyphenol, tert-butyl 3-(hydroxymethyl)piperidine-1-carboxylate, and (E)-4-(dimethylamino)but-2-enoic acid using procedures similar to those described in methods B, C, E, and G. HPLC: 100%. MS: m/z=512 [M+H]$^+$.

Example 27

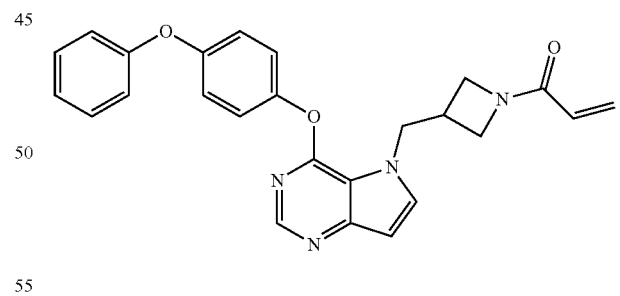

1-(3-((4-(4-phenoxyphenoxy)-5H-pyrrolo[3,2-d]pyrimidin-5-yl)methyl)azetidin-1-yl)prop-2-en-1-one (20)

1-(3-((4-(4-phenoxyphenoxy)-5H-pyrrolo[3,2-d]pyrimidin-5-yl)methyl)azetidin-1-yl)prop-2-en-1-one was prepared from 4-chloro-5H-pyrrolo[3,2-d]pyrimidine, 4-phenoxyphenol, tert-butyl 3-(hydroxymethyl)azetidine-1- carboxylate, and acryloyl chloride using procedures similar to those described in methods B, C, E, and F. HPLC: 74%. MS: m/z=427 [M+H]⁺.

Example 28

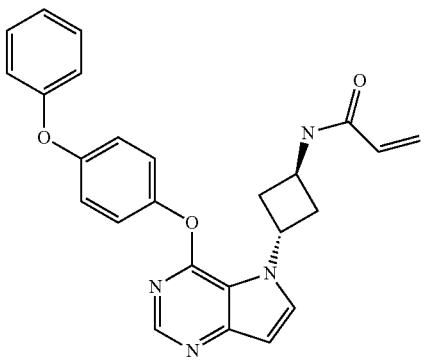 [SMILES: C=CC(=O)N[C@H]1C[C@H](n2ccc3ncnc(Oc4ccc(Oc5ccccc5)cc4)c32)C1]

N-(trans-3-(4-(4-phenoxyphenoxy)-5H-pyrrolo[3,2-d]pyrimidin-5-yl)cyclobutyl)acrylamide (8)

N-(trans-3-(4-(4-phenoxyphenoxy)-5H-pyrrolo[3,2-d]pyrimidin-5-yl)cyclobutyl)acrylamide was prepared from 4-chloro-5H-pyrrolo[3,2-d]pyrimidine, 4-phenoxyphenol, tert-butyl (cis-3-hydroxycyclobutyl)carbamate, and acryloyl chloride using procedures similar to those described in methods B, C, E, and F. HPLC: 97%. MS: m/z=427 [M+H]⁺. ¹H-NMR (DMSO-D6) δ 8.66 (s, 1H), 8.36 (s, 1H), 8.21 (d, 1H), 7.43 (t, 2H), 7.35 (d, 2H), 7.19-7.06 (m, 5H), 6.72 (d, 1H), 6.23 (dd, 1H), 6.10 (d, 1H), 5.62-5.56 (m, 2H), 4.39 (m, 1H), 2.97-2.90 (m, 2H), 2.64-2.56 (m, 2H).

Example 29

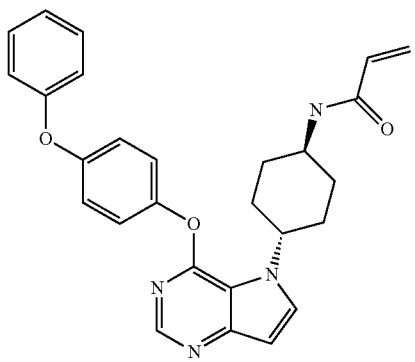 [SMILES: C=CC(=O)N[C@H]1CC[C@H](n2ccc3ncnc(Oc4ccc(Oc5ccccc5)cc4)c32)CC1]

N-(trans-4-(4-(4-phenoxyphenoxy)-5H-pyrrolo[3,2-d]pyrimidin-5-yl)cyclohexyl)acrylamide (39)

N-(trans-4-(4-(4-phenoxyphenoxy)-5H-pyrrolo[3,2-d]pyrimidin-5-yl)cyclohexyl)acrylamide was prepared from 4-chloro-5H-pyrrolo[3,2-d]pyrimidine, 4-phenoxyphenol, tert-butyl (cis-4-hydroxycyclohexyl)carbamate, and acryloyl chloride using procedures similar to those described in methods B, C, E, and F. HPLC: 99%. MS: m/z=455 [M+H]⁺. ¹H-NMR (DMSO-D6) δ 8.35 (s, 1H), 8.04-7.99 (m, 2H), 7.43 (t, 2H), 7.37 (d, 2H), 7.19-7.06 (m, 5H), 6.68 (d, 1H), 6.21-6.06 (m, 2H), 5.58 (d, 1H), 4.83 (m, 1H), 3.77 (m, 1H), 2.22-2.14 (m, 2H), 2.05-1.96 (m, 4H), 1.50-1.38 (m, 2H).

Example 30

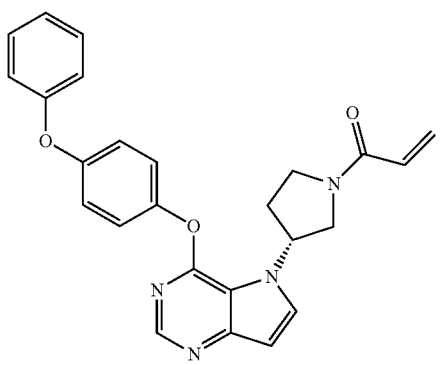

Chiral (R)-1-(3-(4-(4-phenoxyphenoxy)-5H-pyrrolo[3,2-d]pyrimidin-5-yl)pyrrolidin-1-yl)prop-2-en-1-one (34)

(R)-1-(3-(4-(4-phenoxyphenoxy)-5H-pyrrolo[3,2-d]pyrimidin-5-yl)pyrrolidin-1-yl)prop-2-en-1-one was prepared from 4-chloro-5H-pyrrolo[3,2-d]pyrimidine, 4-phenoxyphenol, (S)-tert-butyl 3-hydroxypyrrolidine-1-carboxylate, and acryloyl chloride using procedures similar to those described in methods B, C, E, and F. HPLC: 100%. MS: m/z=427 [M+H]⁺.

Example 31

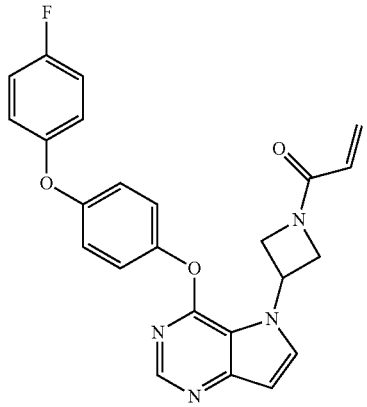 [SMILES: C=CC(=O)N1CC(n2ccc3ncnc(Oc4ccc(Oc5ccc(F)cc5)cc4)c32)C1]

1-(3-(4-(4-(4-fluorophenoxy)phenoxy)-5H-pyrrolo[3,2-d]pyrimidin-5-yl)azetidin-1-yl)prop-2-en-1-one (27)

1-(3-(4-(4-(4-fluorophenoxy)phenoxy)-5H-pyrrolo[3,2-d]pyrimidin-5-yl)azetidin-1-yl)prop-2-en-1-one was prepared from 4-chloro-5H-pyrrolo[3,2-d]pyrimidine, 4-(4-fluorophenoxy)phenol, tert-butyl 3-hydroxyazetidine-1-carboxylate, and acryloyl chloride using procedures similar to those described in methods B, C, E, and F. HPLC: 98%. MS: m/z=431 [M+H]$^+$. $^1$H-NMR (DMSO-D6) δ 8.37 (s, 1H), 8.19 (d, 1H), 7.35-7.24 (m, 4H), 7.14-7.06 (m, 4H), 6.74 (d, 1H), 6.32 (dd, 1H), 6.07 (d, 1H), 5.79 (m, 1H), 5.66 (d, 1H), 4.78 (t, 1H), 4.69 (m, 1H), 4.51-4.41 (m, 2H).

Example 32

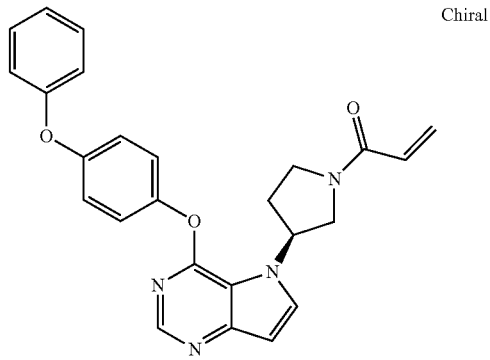 [SMILES: C=CC(=O)N1CC[C@H](n2ccc3ncnc(Oc4ccc(Oc5ccccc5)cc4)c32)C1]

Chiral (S)-1-(3-(4-(4-phenoxyphenoxy)-5H-pyrrolo[3,2-d]pyrimidin-5-yl)pyrrolidin-1-yl)prop-2-en-1-one (5)

(S)-1-(3-(4-(4-phenoxyphenoxy)-5H-pyrrolo[3,2-d]pyrimidin-5-yl)pyrrolidin-1-yl)prop-2-en-1-one was prepared from 4-chloro-5H-pyrrolo[3,2-d]pyrimidine, 4-phenoxyphenol, (R)-tert-butyl 3-hydroxypyrrolidine-1-carboxylate, and acryloyl chloride using procedures similar to those described in methods B, C, E, and F. HPLC: 100%. MS: m/z=427 [M+H]$^+$.

Example 33

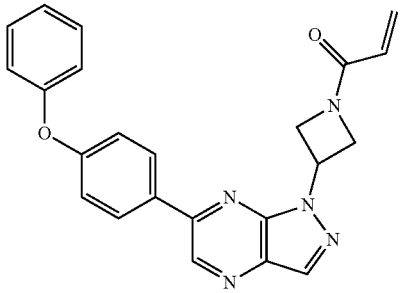 [SMILES: C=CC(=O)N1CC(n2ncc3ncc(-c4ccc(Oc5ccccc5)cc4)nc32)C1]

1-(3-(6-(4-phenoxyphenyl)-1H-pyrazolo[3,4-b]pyrazin-1-yl)azetidin-1-yl)prop-2-en-1-one (23)

1-(3-(6-(4-phenoxyphenyl)-1H-pyrazolo[3,4-b]pyrazin-1-yl)azetidin-1-yl)prop-2-en-1-one was prepared from 6-chloro-1H-pyrazolo[3,4-b]pyrazine, (4-phenoxyphenyl)boronic acid, tert-butyl 3-hydroxyazetidine-1-carboxylate, and acryloyl chloride using procedures similar to those described in methods A, C, E, and F. HPLC: 100%. MS: m/z=398 [M+H]$^+$. $^1$H-NMR (DMSO-D6) δ 9.32 (s, 1H), 8.60 (s, 1H), 8.32 (d, 2H), 7.47 (t, 2H), 7.26-7.12 (m, 5H), 6.43 (dd, 1H), 6.19 (d, 1H), 5.91 (m, 1H), 5.74 (d, 1H), 4.86 (t, 1H), 4.73 (m, 1H), 4.55 (t, 1H), 4.46 (m, 1H).

Example 34

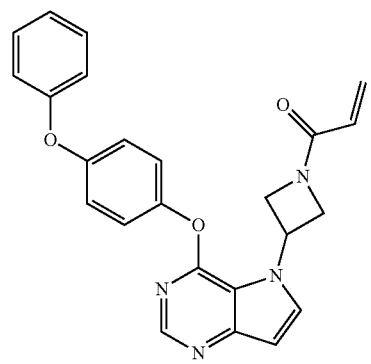

1-(3-(4-((4-phenoxyphenyl)amino)-5H-pyrrolo[3,2-d]pyrimidin-5-yl)azetidin-1-yl)prop-2-en-1-one (6)

1-(3-(4-((4-phenoxyphenyl)amino)-5H-pyrrolo[3,2-d]pyrimidin-5-yl)azetidin-1-yl)prop-2-en-1-one was prepared from 4-chloro-5H-pyrrolo[3,2-d]pyrimidine, 4-phenoxyaniline, tert-butyl 3-iodoazetidine-1-carboxylate, and acryloyl chloride using procedures similar to those described in methods I, D, E, and F. HPLC: 87%. MS: m/z=412 [M+H]$^+$.

Example 35

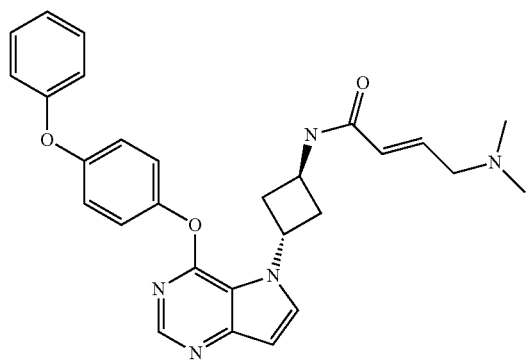 [SMILES: CN(C)C/C=C/C(=O)N[C@H]1C[C@H](n2ccc3ncnc(Oc4ccc(Oc5ccccc5)cc4)c32)C1]

(E)-4-(dimethylamino)-N-(trans-3-(4-(4-phenoxyphenoxy)-5H-pyrrolo[3,2-d]pyrimidin-5-yl)cyclobutyl)but-2-enamide (33)

(E)-4-(dimethylamino)-N-(trans-3-(4-(4-phenoxyphenoxy)-5H-pyrrolo[3,2-d]pyrimidin-5-yl)cyclobutyl)but-2- enamide was prepared from 4-chloro-5H-pyrrolo[3,2-d]pyrimidine, 4-phenoxyphenol, tert-butyl (cis-3-hydroxycyclobutyl)carbamate, and (E)-4-(dimethylamino)but-2-enoic acid using procedures similar to those described in methods B, C, E, and G. HPLC: 100%. MS: m/z=484 [M+H]+. 1H-NMR (DMSO-D6) δ 8.57 (d, 1H), 8.33 (s, 1H), 8.18 (d, 1H), 7.43 (t, 2H), 7.34 (d, 2H), 7.19-7.06 (m, 5H), 6.70 (d, 1H), 6.57 (doublet of triplet, 1H), 6.06 (d, 1H), 5.57 (pentet, 1H), 4.37 (m, 1H), 3.08-2.99 (m, 2H), 2.97-2.87 (m, 2H), 2.63-2.55 (m. 2H), 2.17 (s, 6H).

Example 36

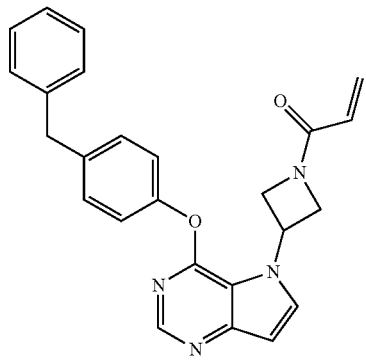 [SMILES: C=CC(=O)N1CC(n2ccc3ncnc(Oc4ccc(Cc5ccccc5)cc4)c32)C1]

1-(3-(4-(4-benzylphenoxy)-5H-pyrrolo[3,2-d]pyrimidin-5-yl)azetidin-1-yl)prop-2-en-1-one (17)

1-(3-(4-(4-benzylphenoxy)-5H-pyrrolo[3,2-d]pyrimidin-5-yl)azetidin-1-yl)prop-2-en-1-one was prepared from 4-chloro-5H-pyrrolo[3,2-d]pyrimidine, 4-benzylphenol, tert-butyl 3-hydroxyazetidine-1-carboxylate, and acryloyl chloride using procedures similar to those described in methods B, C, E, and F. HPLC: 100%. MS: m/z=411 [M+H]+. 1H-NMR (DMSO-D6) δ 8.32 (s, 1H), 8.19 (d, 1H), 7.33-7.28 (m, 6H), 7.23-7.20 (m, 3H), 6.73 (d, 1H), 6.31 (dd, 1H), 6.05 (d, 1H), 5.78 (m, 1H), 5.63 (d, 1H), 4.77 (m, 1H), 4.67 (m, 1H), 4.50-4.38 (m, 2H), 3.99 (s, 2H).

Example 37

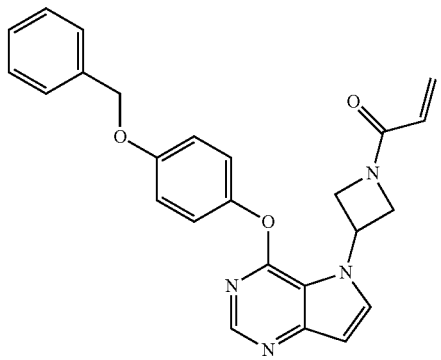 [SMILES: C=CC(=O)N1CC(n2ccc3ncnc(Oc4ccc(OCc5ccccc5)cc4)c32)C1]

1-(3-(4-(4-(benzyloxy)phenoxy)-5H-pyrrolo[3,2-d]pyrimidin-5-yl)azetidin-1-yl)prop-2-en-1-one (16)

1-(3-(4-(4-(benzyloxy)phenoxy)-5H-pyrrolo[3,2-d]pyrimidin-5-yl)azetidin-1-yl)prop-2-en-1-one was prepared from 4-chloro-5H-pyrrolo[3,2-d]pyrimidine, 4-(benzyloxy)phenol, tert-butyl 3-hydroxyazetidine-1-carboxylate, and acryloyl chloride using procedures similar to those described in methods B, C, E, and F. HPLC: 100%. MS: m/z=427 [M+H]+. 1H-NMR (DMSO-d6) δ 8.33 (s, 1H), 8.18 (d, 1H), 7.51-7.32 (m, 5H), 7.24 (d, 2H), 7.08 (d, 2H), 6.73 (d, 1H), 6.32 (dd, 1H), 6.06 (d, 1H), 5.79 (m, 1H), 5.65 (d, 1H), 5.15 (s, 2H), 4.78 (t, 1H), 4.68 (m, 1H), 4.52-4.38 (m, 2H).

Example 38

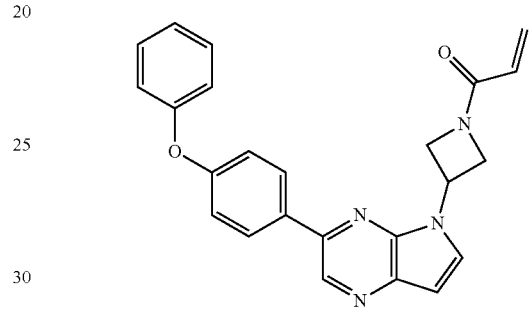

1-(3-(3-(4-phenoxyphenyl)-5H-pyrrolo[2,3-b]pyrazin-5-yl)azetidin-1-yl)prop-2-en-1-one (7)

1-(3-(3-(4-phenoxyphenyl)-5H-pyrrolo[2,3-b]pyrazin-5-yl)azetidin-1-yl)prop-2-en-1-one was prepared from 3-bromo-5H-pyrrolo[2,3-b]pyrazine, (4-phenoxyphenyl)boronic acid, tert-butyl 3-iodoazetidine-1-carboxylate, and acryloyl chloride using procedures similar to those described in methods A, D, E, and F. HPLC: 100%. MS: m/z=397 [M+H]+. 1H-NMR (DMSO-d6) δ 9.08 (s, 1H), 8.22-8.16 (m, 3H), 7.45 (t, 2H), 7.21 (t, 1H), 7.13-7.07 (m, 4H), 6.76 (d, 1H), 6.43 (dd, 1H), 6.19 (d, 1H), 5.76-5.63 (m, 2H), 4.81 (d, 2H), 4.51 (d, 2H).

Example 39

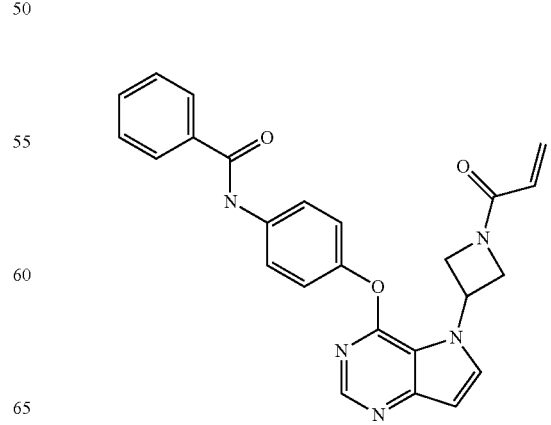

N-(4-((5-(1-acryloylazetidin-3-yl)-5H-pyrrolo[3,2-d]pyrimidin-4-yl)oxy)phenyl)benzamide (35)

N-(4-((5-(1-acryloylazetidin-3-yl)-5H-pyrrolo[3,2-d]pyrimidin-4-yl)oxy)phenyl)benzamide was prepared from 4-chloro-5H-pyrrolo[3,2-d]pyrimidine, N-(4-hydroxyphenyl)benzamide, tert-butyl 3-iodoazetidine-1-carboxylate, and acryloyl chloride using procedures similar to those described in methods B, D, E, and F. HPLC: 94%. MS: m/z=440 [M+H]+. 1H-NMR (DMSO-d6) δ 10.34 (s, 1H), 8.36 (s, 1H), 8.20 (d, 1H), 7.99 (d, 2H), 7.85 (d, 2H), 7.65-7.52 (m, 3H), 7.31 (d, 2H), 6.75 (d, 1H), 6.34 (dd, 1H), 6.08 (d, 1H), 5.81 (m, 1H), 5.67 (d, 1H), 4.85-4.66 (m, 2H), 4.55-4.40 (m, 2H).

Example 40

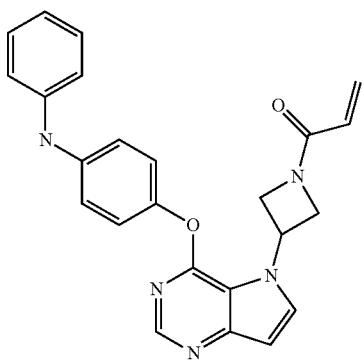

1-(3-(4-(4-(phenylamino)phenoxy)-5H-pyrrolo[3,2-d]pyrimidin-5-yl)azetidin-1-yl)prop-2-en-1-one (22)

1-(3-(4-(4-(phenylamino)phenoxy)-5H-pyrrolo[3,2-d]pyrimidin-5-yl)azetidin-1-yl)prop-2-en-1-one was prepared from 4-chloro-5H-pyrrolo[3,2-d]pyrimidine, 4-(phenylamino)phenol, tert-butyl 3-hydroxyazetidine-1-carboxylate, and acryloyl chloride using procedures similar to those described in methods B, C, E, and F. HPLC: 100%. MS: m/z=412 [M+H]+. 1H-NMR (DMSO-d6) δ 8.35 (s, 1H), 8.20-8.16 (m, 2H), 7.28-7.05 (m, 8H), 6.83 (t, 1H), 6.73 (d, 1H), 6.34 (dd, 1H), 6.08 (d, 1H), 5.80 (m, 1H), 5.67 (d, 1H), 4.79 (t, 1H), 4.69 (m, 1H), 4.54-4.38 (m, 2H).

Example 41

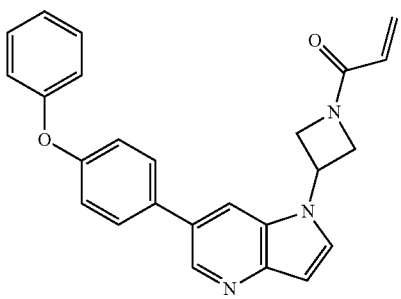

1-(3-(6-(4-phenoxyphenyl)-1H-pyrrolo[3,2-b]pyridin-1-yl)azetidin-1-yl)prop-2-en-1-one (4)

1-(3-(6-(4-phenoxyphenyl)-1H-pyrrolo[3,2-b]pyridin-1-yl)azetidin-1-yl)prop-2-en-1-one was prepared from 6-chloro-1H-pyrrolo[3,2-b]pyridine, (4-phenoxyphenyl)boronic acid, tert-butyl 3-iodoazetidine-1-carboxylate, and acryloyl chloride using procedures similar to those described in methods A, D, E, and F. HPLC: 98%. MS: m/z=396 [M+H]+. 1H-NMR (DMSO-d6) δ 8.69 (s, 1H), 8.18 (s, 1H), 8.11 (d, 1H), 7.79 (d, 2H), 7.43 (t, 3H), 7.21-7.05 (m, 5H), 6.72 (d, 1H), 6.42 (dd, 1H), 6.19 (d, 1H), 5.78-5.62 (m, 2H), 4.81 (t, 1H), 4.66-4.49 (m, 2H), 4.32 (m, 1H).

Example 42

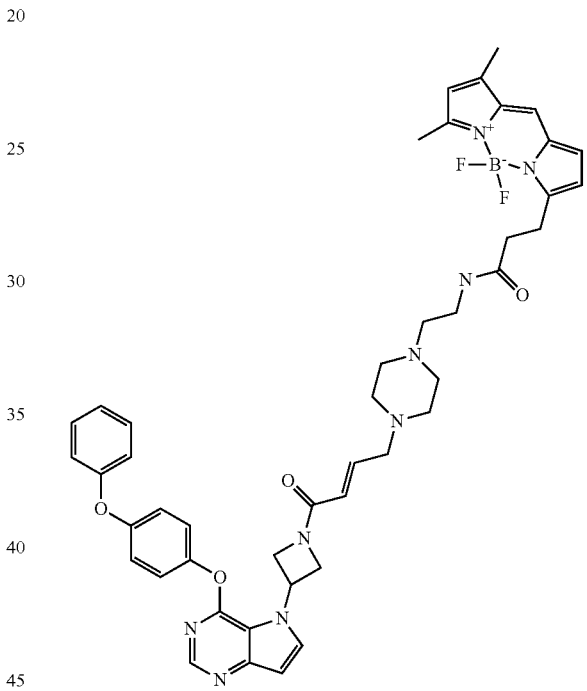

(E)-5,5-difluoro-1,3-dimethyl-7-(3-oxo-3-((2-(4-(4-oxo-4-(3-(4-(4-phenoxyphenoxy)-5H-pyrrolo[3,2-d]pyrimidin-5-yl)azetidin-1-yl)but-2-en-1-yl)piperazin-1-yl)ethyl)amino)propyl)-5H-dipyrrolo[1,2-c:2',1'-f][1,3,2]diazaborinin-4-ium-5-uide (32)

(E)-5,5-difluoro-1,3-dimethyl-7-(3-oxo-3-((2-(4-(4-oxo-4-(3-(4-(4-phenoxyphenoxy)-5H-pyrrolo[3,2-d]pyrimidin-5-yl)azetidin-1-yl)but-2-en-1-yl)piperazin-1-yl)ethyl)amino)propyl)-5H-dipyrrolo[1,2-c:2',1'-f][1,3,2]diazaborinin-4-ium-5-uide was prepared from 4-chloro-5H-pyrrolo[3,2-d]pyrimidine, 4-phenoxyphenol, tert-butyl 3-hydroxyazetidine-1-carboxylate, (E)-4-(4-(2-((tert-butoxycarbonyl)amino)ethyl)piperazin-1-yl)but-2-enoic acid, and 7-(2-carboxyethyl)-5,5-difluoro-1,3-dimethyl-5H-dipyrrolo[1,2-c:2',1'-f][1,3,2]diazaborinin-4-ium-5-uide using procedures similar to those described in methods B, C, E, G, E, and G. HPLC: 95%. MS: m/z=829 [M+H]+.

Example 43

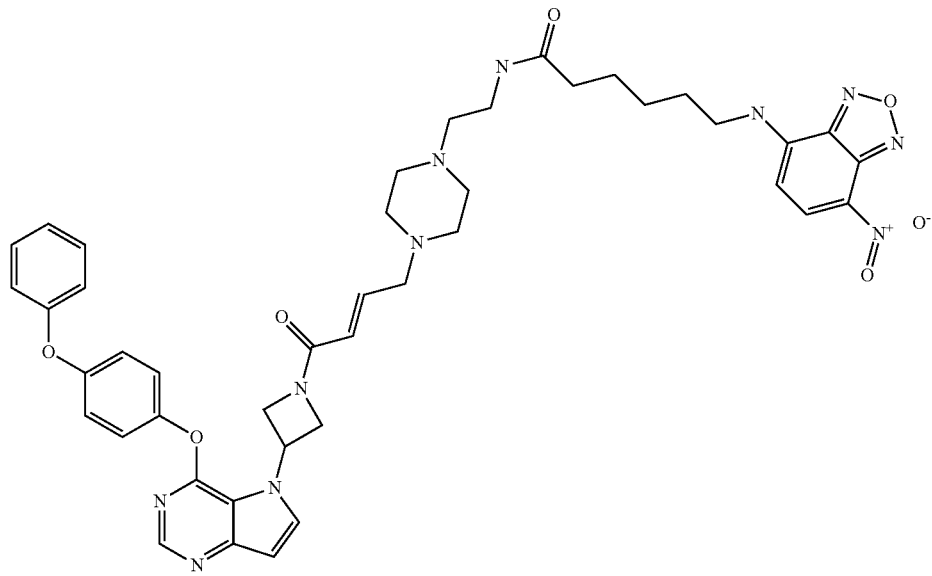

(E)-6-((7-nitrobenzo[c][1,2,5]oxadiazol-4-yl)amino)-
N-(2-(4-(4-oxo-4-(3-(4-(4-phenoxyphenoxy)-5H-
pyrrolo[3,2-d]pyrimidin-5-yl)azetidin-1-yl)but-2-en-
1-yl)piperazin-1-yl)ethyl)hexanamide (31)

(E)-6-((7-nitrobenzo[c][1,2,5]oxadiazol-4-yl)amino)-N-(2-(4-(4-oxo-4-(3-(4-(4-phenoxyphenoxy)-5H-pyrrolo[3,2-d]pyrimidin-5-yl)azetidin-1-yl)but-2-en-1-yl)piperazin-1-yl)ethyl)hexanamide was prepared from 4-chloro-5H-pyrrolo[3,2-d]pyrimidine, 4-phenoxyphenol, tert-butyl 3-iodoazetidine-1-carboxylate, (E)-4-(4-(2-((tert-butoxycarbonyl)amino)ethyl)piperazin-1-yl)but-2-enoic acid, and 6-((7-nitrobenzo[c][1,2,5]oxadiazol-4-yl)amino)hexanoic acid using procedures similar to those described in methods B, D, E, G, E, and H. HPLC: 95%. MS: m/z=830 [M+H]+.

Example 44

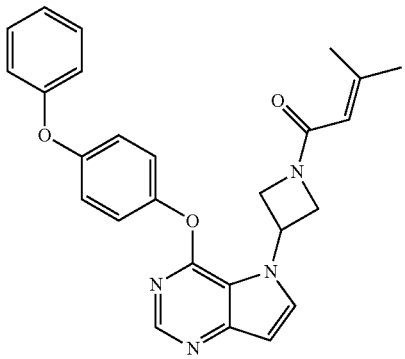 [SMILES: CC(C)=CC(=O)N1CC(n2ccc3ncnc(Oc4ccc(Oc5ccccc5)cc4)c32)C1]

3-methyl-1-(3-(4-(4-phenoxyphenoxy)-5H-pyrrolo
[3,2-d]pyrimidin-5-yl)azetidin-1-yl)but-2-en-1-one
(49)

3-methyl-1-(3-(4-(4-phenoxyphenoxy)-5H-pyrrolo[3,2-d]pyrimidin-5-yl)azetidin-1-yl)but-2-en-1-one was prepared from 4-chloro-5H-pyrrolo[3,2-d]pyrimidine, 4-phenoxyphenol, tert-butyl 3-bromoazetidine-1-carboxylate, and 3-methylbut-2-enoyl chloride using procedures similar to those described in methods B, D, E, and F. HPLC: 100%. MS: m/z=441 [M+H]+. 1H-NMR (DMSO-d6) δ 8.36 (s, 1H), 8.16 (d, 1H), 7.43 (t, 2H), 7.33 (d, 2H), 7.20-7.04 (m, 5H), 6.73 (d, 1H), 5.78-5.67 (m, 2H), 4.70-4.55 (m, 2H), 4.45-4.31 (m, 2H), 2.00 (s, 3H), 1.81 (s, 3H).

Example 45

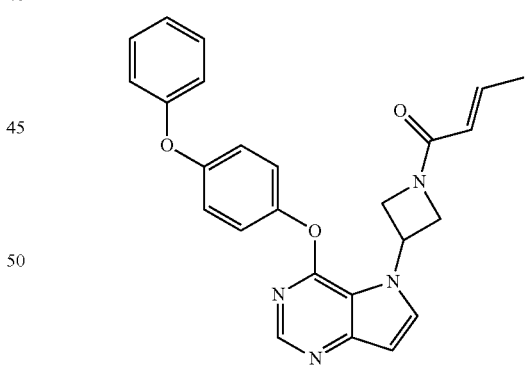

(E)-1-(3-(4-(4-phenoxyphenoxy)-5H-pyrrolo[3,2-d]
pyrimidin-5-yl)azetidin-1-yl)but-2-en-1-one (38)

(E)-1-(3-(4-(4-phenoxyphenoxy)-5H-pyrrolo[3,2-d]pyrimidin-5-yl)azetidin-1-yl)but-2-en-1-one was prepared from 4-chloro-5H-pyrrolo[3,2-d]pyrimidine, 4-phenoxyphenol, tert-butyl 3-bromoazetidine-1-carboxylate, and (E)-but-2-enoic acid using procedures similar to those described in methods B, D, E, and H. HPLC: 98%. MS: m/z=427 [M+H]+. 1H-NMR (DMSO-d6) δ 8.37 (s, 1H), 8.18 (d, 1H), 7.43 (t, 2H), 7.34 (d, 2H), 7.17 (t, 1H), 7.12-7.04 (m, 4H), 6.74 (d, 1H), 6.61 (m, 1H), 6.02 (d, 1H), 5.78 (m, 1H), 4.78-4.61 (m, 2H), 4.50-4.34 (m, 2H), 1.81 (d, 3H).

7.21-7.04 (m, 5H), 6.63 (d, 1H), 6.19-6.00 (m, 2H), 5.54 (d, 1H), 4.48 (t, 2H), 3.20-3.09 (m, 2H), 2.05 (pentet, 2H).

Example 46

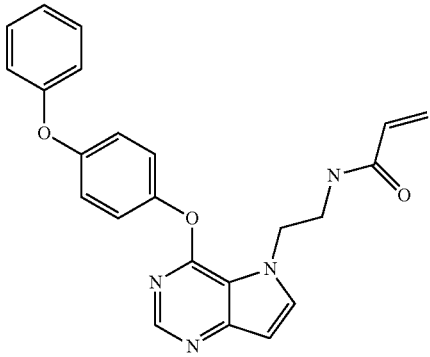 [SMILES: C=CC(=O)NCCn1ccc2ncnc(Oc3ccc(Oc4ccccc4)cc3)c21]

N-(2-(4-(4-phenoxyphenoxy)-5H-pyrrolo[3,2-d]pyrimidin-5-yl)ethyl)acrylamide (42)

N-(2-(4-(4-phenoxyphenoxy)-5H-pyrrolo[3,2-d]pyrimidin-5-yl)ethyl)acrylamide was prepared from 4-chloro-5H-pyrrolo[3,2-d]pyrimidine, 4-phenoxyphenol, tert-butyl(2-iodoethyl)carbamate, and acrylic acid using procedures similar to those described in methods B, D, E, and H. HPLC: 99%. MS: m/z=401 [M+H]$^+$. $^1$H-NMR (DMSO-d6) δ 8.32 (s, 1H), 8.19 (t, 1H), 7.74 (d, 1H), 7.43 (t, 2H), 7.34 (d, 2H), 7.20-7.04 (m, 5H), 6.62 (d, 1H), 6.13 (dd, 1H), 6.02 (d, 1H), 5.56 (d, 1H), 4.54 (t, 2H), 3.65 (q, 2H).

Example 47

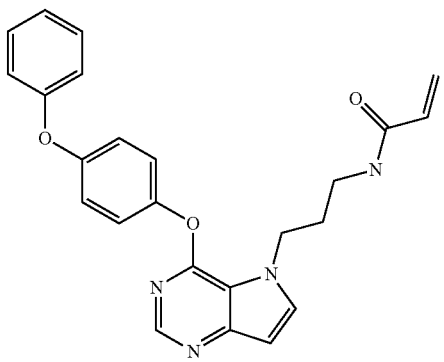 [SMILES: C=CC(=O)NCCCn1ccc2ncnc(Oc3ccc(Oc4ccccc4)cc3)c21]

N-(3-(4-(4-phenoxyphenoxy)-5H-pyrrolo[3,2-d]pyrimidin-5-yl)propyl)acrylamide (26)

N-(3-(4-(4-phenoxyphenoxy)-5H-pyrrolo[3,2-d]pyrimidin-5-yl)propyl)acrylamide was prepared from 4-chloro-5H-pyrrolo[3,2-d]pyrimidine, 4-phenoxyphenol, tert-butyl (3-iodopropyl)carbamate, acrylic acid using procedures similar to those described in methods B, D, E, and H. HPLC: 97%. MS: m/z=415 [M+H]$^+$. $^1$H-NMR (DMSO-d6) δ 8.32 (s, 1H), 8.14 (t, 1H), 7.89 (d, 1H), 7.43 (t, 2H), 7.34 (d, 2H),

Example 48

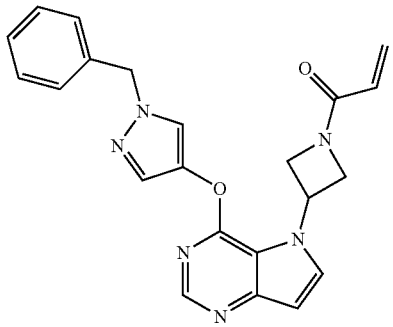 [SMILES: C=CC(=O)N1CC(n2ccc3ncnc(Oc4cnn(Cc5ccccc5)c4)c32)C1]

1-(3-(4-((1-benzyl-1H-pyrazol-4-yl)oxy)-5H-pyrrolo[3,2-d]pyrimidin-5-yl)azetidin-1-yl)prop-2-en-1-one (43)

1-(3-(4-((1-benzyl-1H-pyrazol-4-yl)oxy)-5H-pyrrolo[3,2-d]pyrimidin-5-yl)azetidin-1-yl)prop-2-en-1-one was prepared from 4-chloro-5H-pyrrolo[3,2-d]pyrimidine, 1-benzyl-1H-pyrazol-4-ol, tert-butyl 3-bromoazetidine-1-carboxylate, acrylic acid using procedures similar to those described in methods B, D, E, and H. HPLC: 88%. MS: m/z=401 [M+H]$^+$.

Example 49

(E)-4-(dimethylamino)-1-(3-(6-(4-phenoxyphenyl)-1H-pyrrolo[3,2-b]pyridin-1-yl)azetidin-1-yl)but-2-en-1-one (13)

(E)-4-(dimethylamino)-1-(3-(6-(4-phenoxyphenyl)-1H-pyrrolo[3,2-b]pyridin-1-yl)azetidin-1-yl)but-2-en-1-one was prepared from 6-chloro-1H-pyrrolo[3,2-b]pyridine, (4-phenoxyphenyl)boronic acid, tert-butyl 3-iodoazetidine-1-carboxylate, and (E)-4-(dimethylamino)but-2-enoic acid using procedures similar to those described in methods A, D, E, and H. HPLC: 98%. MS: m/z=453 [M+H]$^+$. $^1$H-NMR (DMSO-d6) δ 8.69 (s, 1H), 8.16 (s, 1H), 8.10 (d, 1H), 7.78 (pentet, 1H), 4.79 (t, 1H), 4.64-4.47 (m, 2H), 4.29 (m, 1H), 3.19 (d, 2H), 2.25 (s, 6H).

Example 50

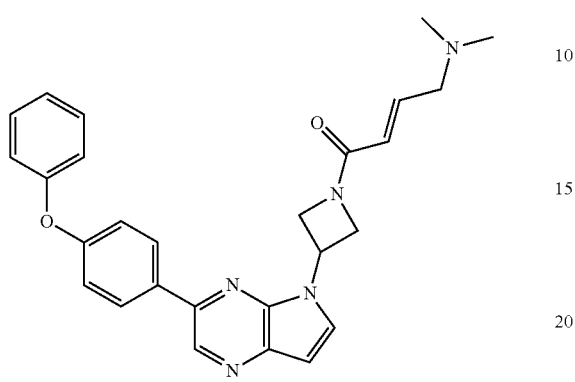

(E)-4-(dimethylamino)-1-(3-(3-(4-phenoxyphenyl)-5H-pyrrolo[2,3-b]pyrazin-5-yl)azetidin-1-yl)but-2-en-1-one (24)

(E)-4-(dimethylamino)-1-(3-(3-(4-phenoxyphenyl)-5H-pyrrolo[2,3-b]pyrazin-5-yl)azetidin-1-yl)but-2-en-1-one was prepared from 3-bromo-5H-pyrrolo[2,3-b]pyrazine, (4-phenoxyphenyl)boronic acid, tert-butyl 3-iodoazetidine-1-carboxylate, and (E)-4-(dimethylamino)but-2-enoic acid using procedures similar to those described in methods A, D, E, and H. HPLC: 95%. MS: m/z=454 [M+H]⁺. ¹H-NMR (DMSO-d6) δ 9.07 (s, 1H), 8.23-8.13 (m, 3H), 7.45 (t, 2H), 7.21 (t, 1H), 7.10 (t, 4H), 6.78-6.62 (m, 2H), 6.23 (d, 1H), 5.64 (pentet, 1H), 4.79 (d, 2H), 4.48 (d, 2H), 3.08 (d, 2H), 2.16 (s, 6H).

Example 51

Chiral

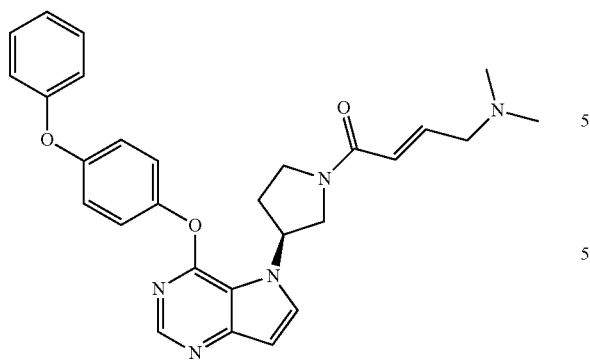

(S,E)-4-(dimethylamino)-1-(3-(4-(4-phenoxyphenoxy)-5H-pyrrolo[3,2-d]pyrimidin-5-yl)pyrrolidin-1-yl)but-2-en-1-one (18)

(S,E)-4-(dimethylamino)-1-(3-(4-(4-phenoxyphenoxy)-5H-pyrrolo[3,2-d]pyrimidin-5-yl)pyrrolidin-1-yl)but-2-en-1-one from 4-chloro-5H-pyrrolo[3,2-d]pyrimidine, 4-phenoxyphenol, (R)-tert-butyl 3-hydroxypyrrolidine-1-carboxylate, and (E)-4-(dimethylamino)but-2-enoic acid using procedures similar to those described in methods B, C, E, and H. HPLC: 100%. MS: m/z=484 [M+H]⁺. ¹H-NMR (DMSO-d6) δ 10.20 (s, 1H), 8.20 (s, 1H), 8.00 (s, 1H), 7.75-7.29 (m, 8H), 6.93-6.58 (m, 3H), 6.42 (dd, 1H), 6.25 (d, 1H), 5.77 (d, 1H), 5.49 (s, 2H).

Example 52

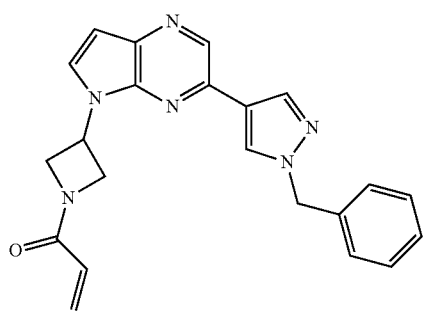 [SMILES: C=CC(=O)N1CC(n2ccc3ncc(-c4cnn(Cc5ccccc5)c4)nc32)C1]

1-(3-(3-(1-benzyl-1H-pyrazol-4-yl)-5H-pyrrolo[2,3-b]pyrazin-5-yl)azetidin-1-yl)prop-2-en-1-one (52)

1-(3-(3-(1-benzyl-1H-pyrazol-4-yl)-5H-pyrrolo[2,3-b]pyrazin-5-yl)azetidin-1-yl)prop-2-en-1-one was prepared from 3-bromo-5H-pyrrolo[2,3-b]pyrazine, 1-benzyl-4-(4,4,5,5-tetramethyl-1,3,2-dioxaborolan-2-yl)-1H-pyrazole, tert-butyl 3-iodoazetidine-1-carboxylate, and acryloyl chloride using procedures similar to those described in methods A, D, E, and F. HPLC: 98%. MS: m/z=385 [M+H]⁺. ¹H-NMR (DMSO-d6) δ 8.83 (s, 1H), 8.48 (s, 1H), 8.13 (s, 1H), 8.08 (d, 1H), 7.40-7.29 (m, 5H), 6.70 (d, 1H), 6.42 (dd, 1H), 6.20 (d, 1H), 5.72 (d, 1H), 5.61 (quintet, 1H), 5.40 (s, 2H), 4.81-4.70 (m, 2H), 4.49 (d, 2H).

Example 53

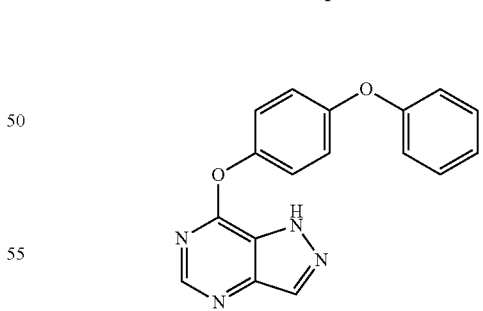

7-(4-phenoxyphenoxy)-1H-pyrazolo[4,3-d]pyrimidine (Method J)

In a microwave vial containing 7-Chloro-1H-pyrazolo[4,3-d]pyrimidine (1.00 g; 6.47 mmol; 1.00 eq.), 4-Phenoxyphenol (1807.17 mg; 9.71 mmol; 1.50 eq.), cesium carbonate (4216.18 mg; 12.94 mmol; 2.00 eq.) was added DMF (15.00 ml; 194.54 mmol; 30.07 eq.). The mixture was stirred at 50° C. for 16 h before it was concentrated and purified with 50 g KPNH column (gradient 65-100% EtOAc in EOAc/Hexane) to afford the desired product as a yellow solid (830.7 mg, 42%). $^1$H NMR (CD$_3$OD) δ 8.49 (s, 1H), 8.27 (s, 1H), 7.27-7.46 (m, 4H), 7.04-7.23 (m, 5H). HPLC: 98%. MS: m/z=305 [M+H]+

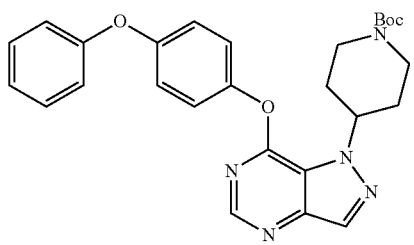 [SMILES: CC(C)(C)OC(=O)N1CCC(n2ncc3ncnc(Oc4ccc(Oc5ccccc5)cc4)c32)CC1]

tert-butyl 4-(7-(4-phenoxyphenoxy)-1H-pyrazolo[4, 3-d]pyrimidin-1-yl)piperidine-1-carboxylate
(Method K)

In a 10 mL microwave vial containing 7-(4-Phenoxyphenoxy)-1H-pyrazolo[4,3-d]pyrimidine (20.00 mg; 0.07 mmol; 1.00 eq.), triphenylphosphine (51.72 mg; 0.20 mmol; 3.00 eq.) and 4-Hydroxy-piperidine-1-carboxylic acid tert-butyl ester (26.46 mg; 0.13 mmol; 2.00 eq.) was added THF (1.00 ml; 37.03 mmol; 563.40 eq.) followed by diisopropyl (E)-diazene-1,2-dicarboxylate (0.04 ml; 0.20 mmol; 3.00 eq.). The solution was stirred at rt for 1 h before it was concentrated and carried to the next step without purification.

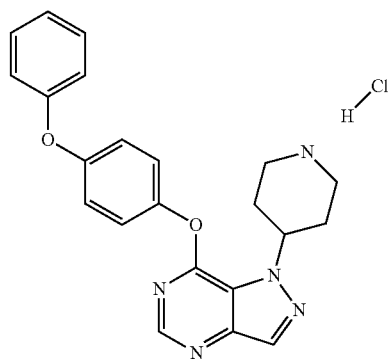

7-(4-phenoxyphenoxy)-1-(piperidin-4-yl)-1H-pyrazolo[4,3-d]pyrimidine hydrochloride (Method L)

In a 10 mL microwave vial containing 4-[7-(4-Phenoxyphenoxy)-pyrazolo[4,3-d]pyrimidin-1-yl]-piperidine-1-carboxylic acid tert-butyl ester (1360.26 mg; 2.79 mmol; 1.00 eq.) in methanol (5.00 ml) was added hydrogen chloride (4.0N in dioxane, 3.00 ml; 13.95 mmol; 5.00 eq.). The solution was stirred at rt for 1 h before it was concentrated and carried to the next step without purification.

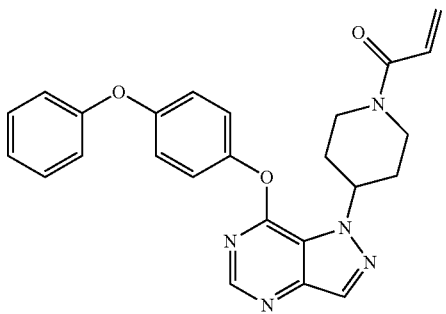 [SMILES: C=CC(=O)N1CCC(n2ncc3ncnc(Oc4ccc(Oc5ccccc5)cc4)c32)CC1]

1-(4-(7-(4-phenoxyphenoxy)-1H-pyrazolo[4,3-d]pyrimidin-1-yl)piperidin-1-yl)prop-2-en-1-one (12)
(Method M)

To a 10 mL reaction vial was added 7-(4-phenoxyphenoxy)-1-piperidin-4-yl-1H-pyrazolo[4,3-d]pyrimidine hydrochloride (80.00 mg; 0.19 mmol; 1.00 eq.), acrylic acid (12.04 μl; 0.19 mmol; 1.00 eq.), ethyl-diisopropyl-amine (0.16 ml; 0.94 mmol; 5.00 eq.) and 1,2-dichloroethane (2.00 ml; 25.26 mmol; 133.86 eq.). The mixture was stirred for 5 min before 2,4,6-tripropyl-[1,3,5,2,4,6]trioxatriphosphinane 2,4,6-trioxide (75.00 μl; 0.19 mmol; 1.00 eq.) was slowly added. The obtained mixture was stirred at rt for 1 h before it was concentrated and purified using prep-HPLC (eluting from 50-80% CH$_3$CN in 0.1% NH$_4$OH/H$_2$O) to afford the desire product as a white solid after lyophilization (2.8 mg, 3.2%). HPLC: 96%. MS: m/z=442[M+H]$^+$. $^1$H-NMR (MeOH-d4) δ 8.31 (s, 1H), 8.13 (s, 1H), 7.25 (m, 4H), 7.0 (m, 5H), 6.76 (d, 1H), 6.12 (d, 1H), 5.64 (d, 1H), 5.25 (s, 1H), 4.61 (d, 1H), 4.23 (d, 1H), 3.28 (m, 1H), 2.99 (t, 1H), 2.19 (m, 4H).

Example 54

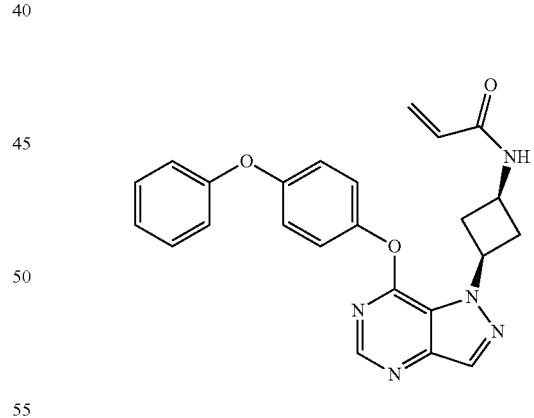

N-((1s,3s)-3-(7-(4-phenoxyphenoxy)-1H-pyrazolo[4, 3-d]pyrimidin-1-yl)cyclobutyl)acrylamide (11)
(relative configuration)

N-((1 s,3s)-3-(7-(4-phenoxyphenoxy)-1H-pyrazolo[4,3-d]pyrimidin-1-yl)cyclobutyl)acrylamide was prepared from 7-chloro-1H-pyrazolo[4,3-d]pyrimidine, 4-phenoxyphenol, tert-butyl ((1s,3s)-3-aminocyclobutyl)carbamate and acrylic acid using procedures similar to those provided in methods J, K, L and M. HPLC: 99%. MS: m/z=428 [M+H]$^+$. $^1$H NMR (CDCl$_3$) δ 8.56 (s, 1H), 7.39 (s, 1H), 7.11-7.41 (m, 11H), 6.36 (d, 1H), 6.08 (m, 2H), 5.73 (m, 1H), 5.47 (m, 1H), 4.56 (m, 1H), 3.17 (m, 2H), 2.79 (m, 2H).

Example 55

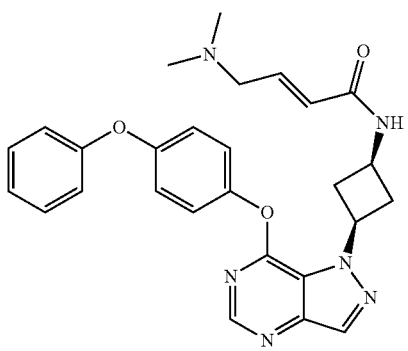 [SMILES: CN(C)C/C=C/C(=O)N[C@H]1C[C@@H](n2ncc3ncnc(Oc4ccc(Oc5ccccc5)cc4)c32)C1]

(E)-4-(dimethylamino)-N-((1s,3s)-3-(7-(4-phenoxyphenoxy)-1H-pyrazolo[4,3-d]pyrimidin-1-yl)cyclobutyl)but-2-enamide (36) (relative configuration)

(E)-4-(dimethylamino)-N-((1s,3 s)-3-(7-(4-phenoxyphenoxy)-1H-pyrazolo[4,3-d]pyrimidin-1-yl)cyclobutyl)but-2-enamide was prepared from 7-chloro-1H-pyrazolo[4,3-d]pyrimidine, 4-phenoxyphenol, tert-butyl ((1s,3s)-3-aminocyclobutyl)carbamate and (E)-4-(dimethylamino)but-2-enoic acid hydrochloride using procedures similar to those provided in methods J, K, L and M.

HPLC: 93%. MS: m/z=485[M+H]$^+$. $^1$H NMR (CDCl$_3$) δ 8.56 (s, 1H), 8.37 (s, 1H), 7.11-7.41 (m, 11H), 6.40 (m, 1H), 5.48 (m, 1H), 5.02 (m, 2H), 4.47 (m, 1H), 3.86 (m, 1H), 3.17 (m, 2H), 2.94 (m, 8H).

Example 56

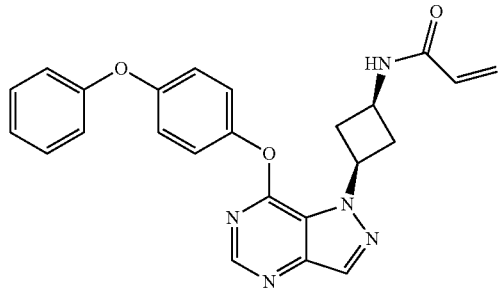 [SMILES: C=CC(=O)N[C@H]1C[C@@H](n2ncc3ncnc(Oc4ccc(Oc5ccccc5)cc4)c32)C1]

N-((1r,3r)-3-(7-(4-phenoxyphenoxy)-1H-pyrazolo[4,3-d]pyrimidin-1-yl)cyclobutyl)acrylamide (21) (relative configuration)

N-((1 r,3 r)-3-(7-(4-phenoxyphenoxy)-1H-pyrazolo[4,3-d]pyrimidin-1-yl)cyclobutyl)-3-(piperidin-1-yl)propanamide was prepared from 7-chloro-1H-pyrazolo[4,3-d]pyrimidine, 4-phenoxyphenol, tert-butyl ((1r,3r)-3-aminocyclobutyl)carbamate and acrylic acid using procedures similar to those provided in methods J, K, L, and M. HPLC: 99%. MS: m/z=428 [M+H]$^+$. $^1$H NMR (CDCl$_3$) δ 8.54 (s, 1H), 8.36 (s, 1H), 7.11-7.41 (m, 11H), 6.33 (d, 1H), 6.15 (m, 1H), 5.92 (m, 1H), 5.72 (m, 1H), 3.27 (m, 2H), 2.80 (m, 2H).

Example 57

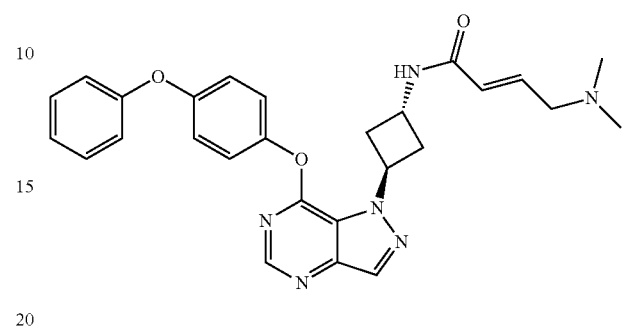

(E)-4-(dimethylamino)-N-((1r,3r)-3-(7-(4-phenoxyphenoxy)-1H-pyrazolo[4,3-d]pyrimidin-1-yl)cyclobutyl)but-2-enamide (41) (relative configuration)

(E)-4-(dimethylamino)-N-((1 r,3r)-3-(7-(4-phenoxyphenoxy)-1H-pyrazolo[4,3-d]pyrimidin-1-yl)cyclobutyl)but-2-enamide was prepared from 7-chloro-1H-pyrazolo[4,3-d]pyrimidine, 4-phenoxyphenol, tert-butyl ((1r,3r)-3-aminocyclobutyl)carbamate and (E)-4-(dimethylamino)but-2-enoic acid hydrochloride using procedures similar to those provided in methods J, K, L, and M. HPLC: 99%. MS: m/z=485 [M+H]$^+$. $^1$H NMR (CDCl$_3$) δ 8.55 (s, 1H), 8.29 (s, 1H), 7.11-7.41 (m, 11H), 6.79 (d, 1H), 6.43 (m, 2H), 5.81 (m, 1H), 5.00 (m, 1H), 4.75 (m, 1H), 3.75 (m, 2H), 3.19 (m, 2H), 2.89 (s, 6H).

Example 58

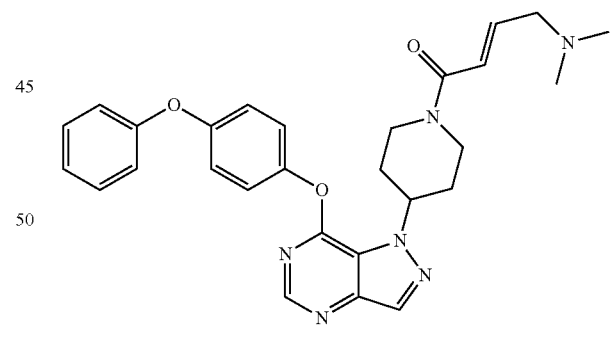

(E)-4-(dimethylamino)-1-(4-(7-(4-phenoxyphenoxy)-1H-pyrazolo[4,3-d]pyrimidin-1-yl)piperidin-1-yl)but-2-en-1-one (14)

(E)-4-(dimethylamino)-1-(4-(7-(4-phenoxyphenoxy)-1H-pyrazolo[4,3-d]pyrimidin-1-yl)piperidin-1-yl)but-2-en-1-one was prepared from 7-chloro-1H-pyrazolo[4,3-d]pyrimidine, 4-phenoxyphenol, tert-butyl 4-hydroxypiperidine-1-carboxylate and (E)-4-(dimethylamino)but-2-enoic acid hydrochloride using procedures similar to those provided in methods J, K, L, and M.

HPLC: 95%. MS: m/z=499 [M+H]⁺. ¹H NMR (DMSO-d₆) δ 8.50 (s, 1H), 8.43 (s, 1H), 7.46 (m, 4H), 7.11 (m, 5H), 6.79 (m, 1H), 6.59 (m, 1H), 5.23 (m, 1H), 4.52 (m, 1H), 4.25 (m, 1H), 2.96 (t, 1H), 2.47 (s, 6H), 2.22 (m, 2H), 2.04 (m, 2H).

Example 59

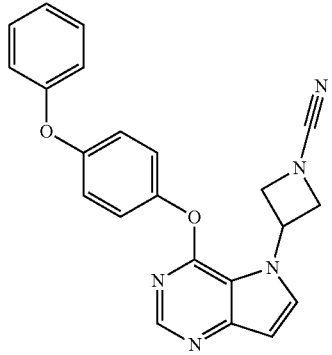 [SMILES: N#CN1CC(n2ccc3ncnc(Oc4ccc(Oc5ccccc5)cc4)c32)C1]

3-[4-(4-phenoxyphenoxy)-5H-pyrrolo[3,2-d]pyrimidin-5-yl]azetidine-1-carbonitrile (68)

To a solution of (3-[4-(4-phenoxyphenoxy)-5H-pyrrolo[3,2-d]pyrimidin-5-yl]azetidine (700 mg, 1.95 mmol, 1.00 equiv) in dichloromethane/water (3:1, 10 mL) was added sodium bicarbonate (657 mg, 7.82 mmol, 4.00 equiv) at RT. This was followed by the addition of carbononitridic bromide (249 mg, 2.35 mmol, 1.20 equiv). The resulting solution was stirred overnight at RT. The reaction mixture was quenched by 10 mL water and extracted with 3×20 mL dichloromethane. The organic phases were combined, dried over anhydrous sodium sulfate and concentrated under reduced pressure. The crude product was purified by Prep HPLC with the following conditions: XBridge Prep C18 OBD Column, 19×150 mm, 5 um; MeCN in water (with 10 mM NH₄HCO₃), 40.0% to 50.0% gradient in 11 min. 3-[4-(4-phenoxyphenoxy)-5H-pyrrolo[3,2-d]pyrimidin-5-yl]azetidine-1-carbonitrile was obtained as a yellow solid (30 mg, 10% for 3 steps). HPLC: 99.0%, RT=1.805 min. MS: m/z=384.3 [M+H]⁺. ¹H-NMR (400 MHz, DMSO-d₆) δ 8.37 (s, 1H), 8.25 (d, J=3.2 Hz, 1H), 7.36-7.45 (m, 4H), 7.05-7.18 (m, 5H), 6.77 (d, J=3.2 Hz, 1H), 5.79-5.87 (m, 1H), 4.65-4.72 (m, 4H).

Example 60

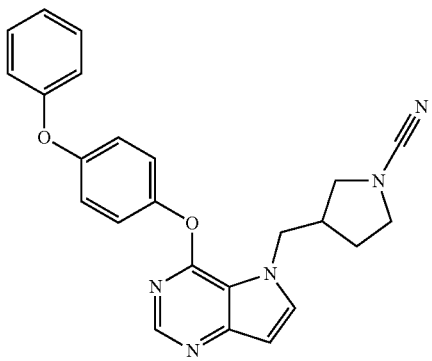 [SMILES: N#CN1CCC(Cn2ccc3ncnc(Oc4ccc(Oc5ccccc5)cc4)c32)C1]

3-[[4-(4-phenoxyphenoxy)-5H-pyrrolo[3,2-d]pyrimidin-5-yl]methyl]pyrrolidine-1-carbonitrile (58)

At RT, to the solution of 3-[[4-(4-phenoxyphenoxy)-5H-pyrrolo[3,2-d]pyrimidin-5-yl]methyl]pyrrolidine (780 mg, 2.02 mmol, 1.00 equiv) in dichloromethane/water (10:4, 14 mL) were added sodium bicarbonate (679 mg, 8.08 mmol, 4.00 equiv) and carbononitridic bromide (254 mg, 2.40 mmol, 1.20 equiv). The resulting solution was stirred overnight at RT. The reaction mixture was extracted with 3×10 mL dichloromethane. The organic phases were combined, dried over anhydrous sodium sulfate and concentrated under reduced pressure. The crude product was purified by Prep HPLC with the following conditions: XBridge Prep C18 OBD Column, 19×150 mm, 5 um; MeCN in water (with 10 mM NH₄HCO₃), 35.0% to 70.0% gradient in 10 min. 3-[[4-(4-phenoxyphenoxy)-5H-pyrrolo[3,2-d]pyrimidin-5-yl]methyl]pyrrolidine-1-carbonitrile was obtained as an off-white solid (230 mg, 28%). HPLC: 97.3%, RT=2.027 min. MS: m/z=412.4 [M+H]⁺. ¹H-NMR (400 MHz, DMSO-d₆) δ 8.33 (s, 1H), 7.90 (d, J=4 Hz, 1H), 7.45-7.35 (m, 4H), 7.18-7.06 (m, 5H), 6.67-6.66 (d, J=4 Hz, 1H), 4.53-4.42 (m, 2H), 3.52-3.49 (m, 1H), 3.48-3.37 (m, 2H), 3.35-3.18 (m, 1H), 2.91-2.84 (m, 1H), 1.91-1.83 (m, 1H), 1.72-1.65 (m, 1H).

Example 61

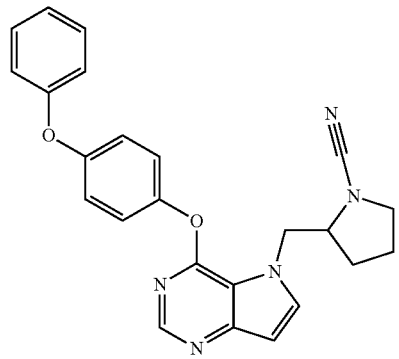 [SMILES: N#CN1CCCC1Cn1ccc2ncnc(Oc3ccc(Oc4ccccc4)cc3)c21]

2-[[4-(4-phenoxyphenoxy)-5H-pyrrolo[3,2-d]pyrimidin-5-yl]methyl]pyrrolidine-1-carbonitrile (61)

To a solution of 2-[[4-(4-phenoxyphenoxy)-5H-pyrrolo[3,2-d]pyrimidin-5-yl]methyl]pyrrolidine (382 mg, 0.99 mmol, 1.00 equiv) in dichloromethane/water (3:1, 8 mL) was added sodium bicarbonate (333 mg, 3.96 mmol, 4.00 equiv) at RT. This was followed by the addition of carbononitridic bromide (126 mg, 1.19 mmol, 1.20 equiv). The resulting solution was stirred overnight at RT. The reaction mixture was quenched by 10 mL water and extracted with 3×20 mL dichloromethane. The organic phases were combined, dried over anhydrous sodium sulfate and concentrated under reduced pressure. The crude product was purified by Prep HPLC with the following condition: XBridge Prep C18 OBD Column, 19×150 mm, 5 um; MeCN in water (with 10 mM NH4HCO3), 40% to 65% gradient in 10 min. 2-[[4-(4-phenoxyphenoxy)-5H-pyrrolo[3,2-d]pyrimidin-5-yl]methyl]pyrrolidine-1-carbonitrile was obtained as a yellow solid (34 mg, 10% for 3 steps). HPLC: 99.4%, RT=2.009 min. MS: m/z=412.2 [M+H]+. 1H-NMR (400 MHz, DMSO-d6) δ 8.33 (s, 1H), 7.88 (d, J=3.2 Hz, 1H), 7.45-7.40 (m, 2H), 7.36-7.33 (m, 2H), 7.19-7.06 (m, 5H), 6.68 (d, J=3.2 Hz, 1H), 4.59-4.53 (m, 1H), 4.49-4.43 (m, 1H), 4.16-4.13.

Example 62

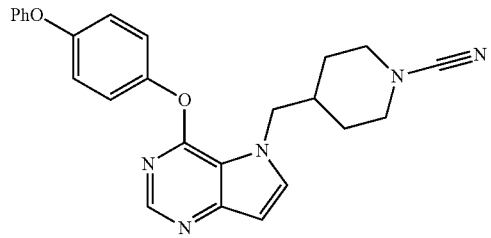 [SMILES: N#CN1CCC(Cn2ccc3ncnc(Oc4ccc(Oc5ccccc5)cc4)c32)CC1]

4-[[4-(4-phenoxyphenoxy)-5H-pyrrolo[3,2-d]pyrimidin-5-yl]methyl]piperidine-1-carbonitrile (59)

To a solution of 4-[[4-(4-phenoxyphenoxy)-5H-pyrrolo[3,2-d]pyrimidin-5-yl]methyl]piperidine (80 mg, 0.20 mmol, 1.00 equiv) in dichloromethane/water (10:4, 5 mL) was added sodium bicarbonate (67 mg, 0.80 mmol, 4.00 equiv) at RT. This was followed by the addition of carbononitridic bromide (25 mg, 0.24 mmol, 1.20 equiv). The resulting solution was stirred overnight at RT. The resulting mixture was concentrated under reduced pressure. The crude product was purified by Prep HPLC with the following conditions: XBridge Prep C18 OBD Column, 19×150 mm, 5 um; MeCN in water (with 10 mM $NH_4HCO_3$), 35.0% to 70.0% gradient in 10 min. 4-[[4-(4-phenoxyphenoxy)-5H-pyrrolo[3,2-d]pyrimidin-5-yl]methyl]piperidine-1-carbonitrile was obtained as a white solid (30 mg, 35%). HPLC: 97.7%, RT=2.028 min. MS: m/z=426.1 [M+H]$^+$. $^1$H-NMR (400 MHz, DMSO-d$_6$) δ 8.32 (s, 1H) 7.85 (d, J=3.2 Hz, 1H), 7.45-7.41 (m, 2H), 7.19-7.06 (m, 5H), 6.64 (s, 1H), 4.35 (d, J=7.2 Hz, 2H), 3.37-3.30 (m, 2H), 2.96 (m, 2H), 2.10-2.05 (m, 1H), 1.46-1.37 (m, 4H).

Example 63

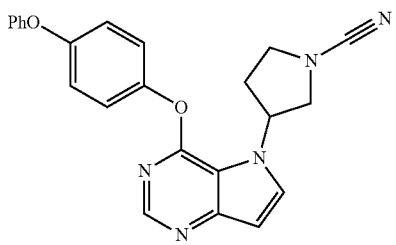 [SMILES: N#CN1CCC(n2ccc3ncnc(Oc4ccc(Oc5ccccc5)cc4)c32)C1]

3-[4-(4-phenoxyphenoxy)-5H-pyrrolo[3,2-d]pyrimidin-5-yl]pyrrolidine-1-carbonitrile (60)

To a solution of 3-[4-(4-phenoxyphenoxy)-5H-pyrrolo[3,2-d]pyrimidin-5-yl]pyrrolidine (74 mg, 0.20 mmol, 1.00 equiv) in dichloromethane/water (10:4, 3 mL) was added sodium bicarbonate (67 mg, 0.80 mmol, 4.00 equiv) at RT. This was followed by the addition of carbononitridic bromide (25 mg, 0.24 mmol, 1.20 equiv). The resulting solution was stirred overnight at RT. The reaction mixture was concentrated under reduced pressure. The crude product was purified by Prep HPLC with the following conditions: XBridge Prep C18 OBD Column, 19×150 mm, 5 um; MeCN in water (with 10 mM $NH_4HCO_3$), 35.0% to 70.0% gradient in 10 min. 3-[4-(4-phenoxyphenoxy)-5H-pyrrolo[3,2-d]pyrimidin-5-yl]pyrrolidine-1-carbonitrile was obtained as a white solid (30 mg, 38%). HPLC: 98.9%, RT=1.922 min. MS: m/z=398.1 [M+H]$^+$. $^1$H-NMR (400 MHz, DMSO-d$_6$) δ 8.35 (s, 1H), 7.96 (d, J=3.2 Hz, 1H), 7.45-7.35 (m, 4H), 7.18-7.05 (m, 5H), 6.70 (d, J=3.2 Hz, 1H), 5.63 (t, J=5.2 Hz, 1H), 3.94-3.83 (m, 2H) 3.68-3.60 (m, 2H), 3.32-3.30 (m, 2H).

Example 64

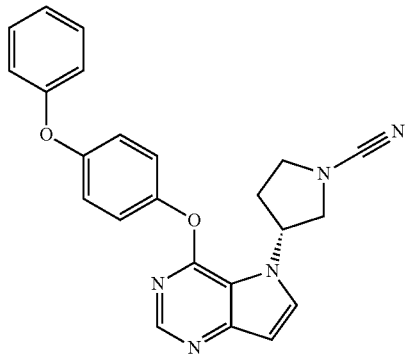 [SMILES: N#CN1CC[C@@H](n2ccc3ncnc(Oc4ccc(Oc5ccccc5)cc4)c32)C1]

(3R)-3-[4-(4-phenoxyphenoxy)-5H-pyrrolo[3,2-d]pyrimidin-5-yl]pyrrolidine-1-carbonitrile (71)

To a solution of (3R)-3-[4-(4-phenoxyphenoxy)-5H-pyrrolo[3,2-d]pyrimidin-5-yl]pyrrolidine (340 mg, 0.91 mmol, 1.00 equiv) in dichloromethane/water (10:4, 3 mL) was added sodium bicarbonate (368 mg, 4.38 mmol, 4.80 equiv) at RT. This was followed by the addition of carbononitridic bromide (116 mg, 1.10 mmol, 1.20 equiv). The resulting solution was stirred overnight at RT. The reaction mixture was concentrated under reduced pressure. The residue was purified by Prep HPLC with the following conditions: XBridge Prep C18 OBD Column, 19×150 mm, 5 um; MeCN in water (with 10 mM $NH_4HCO_3$), 30.0% to 65.0% gradient in 10 min. 3-[4-(4-phenoxyphenoxy)-5H-pyrrolo[3,2-d]pyrimidin-5-yl]pyrrolidine-1-carbonitrile was obtained as a white solid (300 mg, 46% for 3 steps). HPLC: 95.0%, RT=3.061 min. MS: m/z=398.1 [M+H]$^+$. $^1$H-NMR (400 MHz, CDCl$_3$) δ 8.60-8.40 (s, 1H), 7.60-7.45 (s, 1H), 7.40-7.30 (m, 2H), 7.20-7.00 (m, 7H), 6.90-6.75 (s, 1H), 5.85-5.60 (m, 1H), 4.10-3.95 (m, 1H), 3.90-3.75 (m, 1H), 3.75-3.55 (m, 2H), 2.70-2.50 (m, 1H), 2.50-2.30 (m, 1H).

Example 65

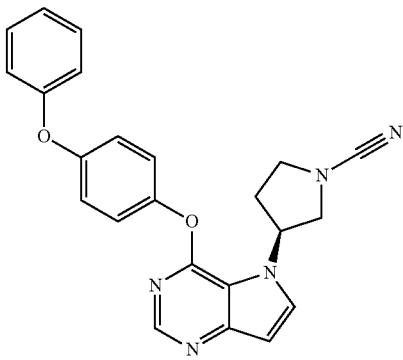 [SMILES: N#CN1CC[C@H](n2ccc3ncnc(Oc4ccc(Oc5ccccc5)cc4)c32)C1]

(3S)-3-[4-(4-phenoxyphenoxy)-5H-pyrrolo[3,2-d]pyrimidin-5-yl]pyrrolidine-1-carbonitrile (72)

To a solution of (3S)-3-[4-(4-phenoxyphenoxy)-5H-pyrrolo[3,2-d]pyrimidin-5-yl]pyrrolidine (340 mg, 0.91 mmol, 1.00 equiv) in dichloromethane/water (3:1, 10 mL) was added sodium bicarbonate (368 mg, 4.38 mmol, 4.80 equiv) at RT. This was followed by the addition of carbononitridic bromide (116 mg, 1.10 mmol, 1.20 equiv). The resulting solution was stirred overnight at RT. The reaction mixture was concentrated under reduced pressure. The residue was purified by Prep HPLC with the following conditions: XBridge Prep C18 OBD Column, 19×150 mm, 5 um; MeCN in water (with 10 mM $NH_4HCO_3$), 30.0% to 65.0% gradient in 10 min. 3-[4-(4-phenoxyphenoxy)-5H-pyrrolo[3,2-d]pyrimidin-5-yl]pyrrolidine-1-carbonitrile was obtained as a white solid (80 mg, 13% for 3 steps). HPLC: 95.0%, RT=2.835 min. MS: m/z=398.1 [M+H]$^+$. $^1$H-NMR (400 MHz, $CDCl_3$) δ 8.65-8.55 (s, 1H), 7.75-7.55 (s, 1H), 7.45-7.30 (m, 2H), 7.25-7.00 (m, 7H), 6.95-6.80 (s, 1H), 5.85-5.70 (m, 1H), 4.10-3.98 (m, 1H), 3.90-3.80 (m, 1H), 3.80-3.55 (m, 2H), 2.70-2.55 (m, 1H), 2.55-2.30 (m, 1H).

Example 66

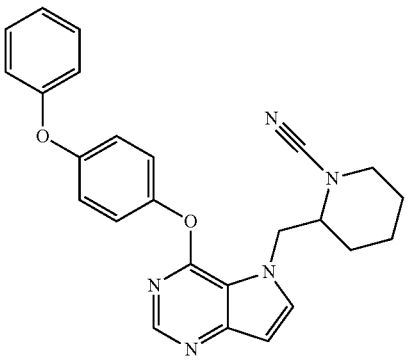 [SMILES: N#CN1CCCCC1Cn1ccc2ncnc(Oc3ccc(Oc4ccccc4)cc3)c21]

2-[[4-(4-phenoxyphenoxy)-5H-pyrrolo[3,2-d]pyrimidin-5-yl]methyl]piperidine-1-carbonitrile (62)

To a solution of 2-[[4-(4-phenoxyphenoxy)-5H-pyrrolo[3,2-d]pyrimidin-5-yl]methyl]pyrrolidine (382 mg, 0.99 mmol, 1.00 equiv) in dichloromethane/water (3:1, 8 mL) was added sodium bicarbonate (333 mg, 3.96 mmol, 4.00 equiv) at RT. This was followed by the addition of carbononitridic bromide (126 mg, 1.19 mmol, 1.20 equiv). The resulting solution was stirred overnight at RT. The reaction mixture was quenched by 10 mL water and extracted with 3×20 mL dichloromethane. The organic phases were combined, dried over anhydrous sodium sulfate and concentrated under reduced pressure. The crude product was purified by Prep HPLC with the following conditions: XBridge Prep C18 OBD Column, 19×150 mm, 5 um; MeCN in water (with 10 mM $NH_4HCO_3$), 40% to 65% gradient in 10 min. 2-[[4-(4-phenoxyphenoxy)-5H-pyrrolo[3,2-d]pyrimidin-5-yl]methyl]piperidine-1-carbonitrile was obtained as a yellow solid (34 mg, 10% for 3 steps). HPLC: 96.8%, RT=1.515 min. MS: m/z=426.2 [M+H]$^+$. $^1$H-NMR (400 MHz, DMSO-$d_6$) δ 8.34 (s, 1H), 7.87 (d, J=3.2 Hz, 1H), 7.45-7.40 (m, 2H), 7.39-7.34 (m, 2H), 7.19-7.06 (m, 5H), 6.68 (d, J=3.2 Hz, 1H), 4.78-4.72 (m, 1H), 4.61-4.55 (m, 1H), 3.76-3.73 (m, 1H), 3.45-3.40 (m, 1H), 3.13-3.08 (m, 1H), 1.72-1.70 (m, 1H), 1.61-1.54 (m, 3H), 1.48-1.41 (m, 2H).

Example 67

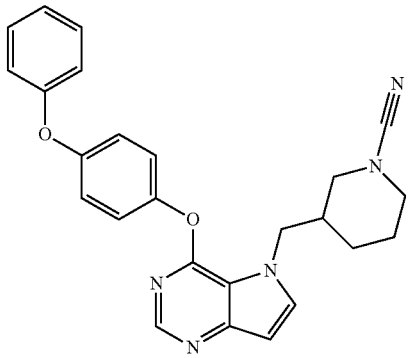 [SMILES: N#CN1CCCC(Cn2ccc3ncnc(Oc4ccc(Oc5ccccc5)cc4)c32)C1]

3-[[4-(4-phenoxyphenoxy)-5H-pyrrolo[3,2-d]pyrimidin-5-yl]methyl]piperidine-1-carbonitrile (63)

To a solution of 3-[[4-(4-phenoxyphenoxy)-5H-pyrrolo[3,2-d]pyrimidin-5-yl]methyl]piperidine (380 mg, 0.99 mmol, 1.00 equiv) in dichloromethane/water (3:1, 8 mL) was added sodium bicarbonate (333 mg, 3.96 mmol, 4.00 equiv). This was followed by the addition of carbononitridic bromide (126 mg, 1.19 mmol, 1.20 equiv). The resulting solution was stirred overnight at RT. The reaction mixture was quenched by 10 mL water and extracted with 3×20 mL dichloromethane. The organic phases were combined, dried over anhydrous sodium sulfate and concentrated under reduced pressure. The crude product was purified by Prep HPLC with the following conditions: XBridge Prep C18 OBD Column, 19×150 mm, 5 um; MeCN in water (with 10 mM $NH_4HCO_3$), 35% to 70% gradient in 12 min. 3-[[4-(4-phenoxyphenoxy)-5H-pyrrolo[3,2-d]pyrimidin-5-yl]methyl]piperidine-1-carbonitrile was obtained (32 mg, 12% for 3 steps). HPLC: 99.2%, RT=2.116 min. MS: m/z=426.2 [M+H]$^+$. $^1$H-NMR (400 MHz, DMSO-$d_6$) δ 8.33 (s, 1H), 7.85 (d, J=3.2 Hz, 1H), 7.45-7.40 (m, 2H), 7.37-7.33 (m, 2H), 7.19-7.06 (m, 5H), 6.66 (d, J=2.8 Hz, 1H), 4.40-4.35 (m, 2H), 3.34-3.16 (m, 2H), 3.03-2.91 (m, 1H), 2.89-2.86 (m, 1H), 2.27-2.23 (m, 1H), 1.71-1.46 (m, 3H), 1.28-1.18 (m, 1H).

Example 68

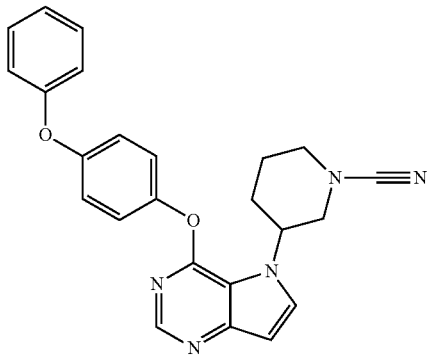 [SMILES: N#CN1CCCC(n2ccc3ncnc(Oc4ccc(Oc5ccccc5)cc4)c32)C1]

3-[4-(4-phenoxyphenoxy)-5H-pyrrolo[3,2-d]pyrimidin-5-yl]piperidine-1-carbonitrile (64)

To a solution of 3-[4-(4-phenoxyphenoxy)-5H-pyrrolo[3,2-d]pyrimidin-5-yl]piperidine (275 mg, 0.71 mmol, 1.00 equiv) in dichloromethane/water (3:1, 8 mL) was added sodium bicarbonate (239 mg, 2.85 mmol, 4.00 equiv) at RT. This was followed by the addition of carbononitridic bromide (91 mg, 0.86 mmol, 1.20 equiv). The resulting solution was stirred overnight at RT. The reaction mixture was diluted with 10 mL water and extracted with 3×20 mL dichloromethane. The organic phases were combined, dried over anhydrous sodium sulfate and concentrated under reduced pressure. The crude product (100 mg) was purified by Prep HPLC with the following conditions: XBridge Prep C18 OBD Column, 19×150 mm, 5 um; MeCN in water (with 10 mM $NH_4HCO_3$), 30% to 75% gradient in 8 min. 3-[4-(4-phenoxyphenoxy)-5H-pyrrolo[3,2-d]pyrimidin-5-yl]piperidine-1-carbonitrile was obtained (31 mg, 15% for 3 steps). HPLC: 98.9%, RT=2.251 min. MS: m/z=412.1 [M+H]$^+$. $^1$H-NMR (400 MHz, DMSO-d$_6$) δ 8.34 (s, 1H), 7.98 (d, J=3.2 Hz, 1H), 7.45-7.35 (m, 4H), 7.18-7.06 (m, 5H), 6.70 (d, J=3.2 Hz, 1H), 5.05-5.01 (m, 1H), 3.86-3.81 (m, 1H), 3.42-3.362 (m, 2H), 3.13-3.06 (m, 1H), 2.23-2.11 (m, 2H), 1.91-1.88 (m, 2H).

Example 69

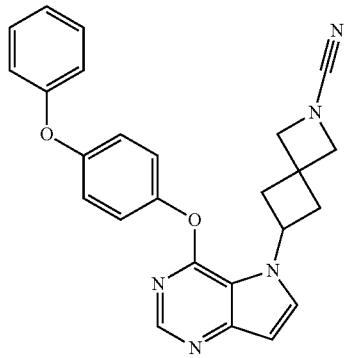 [SMILES: N#CN1CC2(CC(n3ccc4ncnc(Oc5ccc(Oc6ccccc6)cc5)c43)C2)C1]

6-[4-(4-phenoxyphenoxy)-5H-pyrrolo[3,2-d]pyrimidin-5-yl]-2-azaspiro[3.3]heptane-2-carbonitrile (69)

To a solution of (6-[4-(4-phenoxyphenoxy)-5H-pyrrolo[3,2-d]pyrimidin-5-yl]-2-azaspiro[3.3]heptane (382 mg, 0.96 mmol, 1.00 equiv) in dichloromethane/water (3:1, 10 mL) was added sodium bicarbonate (322.6 mg, 3.84 mmol, 4.00 equiv) at RT. This was followed by the addition of carbononitridic bromide (122 mg, 1.15 mmol, 1.20 equiv). The resulting solution was stirred overnight at RT. The reaction mixture was quenched by 10 mL water and extracted with 3×20 mL dichloromethane. The organic phases were combined, dried over anhydrous sodium sulfate and concentrated under reduced pressure. The crude product was purified by Prep HPLC with the following conditions: XBridge Prep C18 OBD Column, 19×150 mm, 5 um; MeCN in water (with 0.1% TFA), 40.0% to 50.0% gradient in 11 min. 6-[4-(4-phenoxyphenoxy)-5H-pyrrolo[3,2-d]pyrimidin-5-yl]-2-azaspiro[3.3]heptane-2-carbonitrile was obtained as a yellow solid (30 mg, 15% for 3 steps). HPLC: 98.2%, RT=1.802 min. MS: m/z=424.4 [M+H]$^+$. $^1$H-NMR (400 MHz, DMSO-d$_6$) δ 8.31 (s, 1H), 8.05 (d, J=3.2 Hz, 1H), 7.41-7.45 (m, 2H), 7.32-7.34 (m, 2H), 7.14-7.18 (m, 1H), 7.06-7.12 (m, 4H), 6.67 (d, J=3.2 Hz, 1H), 5.17-5.26 (m, 1H), 4.3 (s, 2H), 4.15 (s, 2H), 2.84-2.89 (m, 2H), 2.74-2.80 (m, 2H).

Example 70

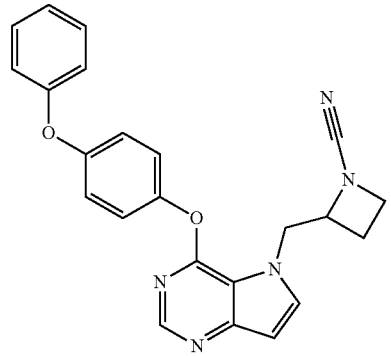 [SMILES: N#CN1CCC1Cn1ccc2ncnc(Oc3ccc(Oc4ccccc4)cc3)c21]

2-[[4-(4-phenoxyphenoxy)-5H-pyrrolo[3,2-d]pyrimidin-5-yl]methyl]azetidine-1-carbonitrile (65)

To a solution of 2-[[4-(4-phenoxyphenoxy)-5H-pyrrolo[3,2-d]pyrimidin-5-yl]methyl]azetidine (491 mg, 1.32 mmol, 1.00 equiv) in dichloromethane/water (3:1, 8 mL) was added sodium bicarbonate (443.5 mg, 5.28 mmol, 4.00 equiv) at RT. This was followed by the addition of carbononitridic bromide (168 mg, 1.59 mmol, 1.20 equiv). The resulting solution was stirred overnight at RT. The reaction mixture was quenched by 10 mL water and extracted with 3×20 mL dichloromethane. The organic phases were combined, dried over anhydrous sodium sulfate and concentrated under reduced pressure. The crude product was purified by Prep HPLC with the following conditions: XBridge Prep C18 OBD Column, 19×150 mm, 5 um; MeCN in water (with 10 mM $NH_4HCO_3$), 46.0% to 48.0% gradient in 10 min. 2-[[4-(4-phenoxyphenoxy)-5H-pyrrolo[3,2-d]pyrimidin-5-yl]methyl]azetidine-1-carbonitrile was obtained (31 mg, 8% for 3 steps). HPLC: 98.6%, RT=1.255 min. MS: m/z=398.1

[M+H]+. 1H-NMR (400 MHz, DMSO-d6) δ 8.34 (s, 1H), 7.88 (d, J=3.2 Hz, 1H), 7.45-7.35 (m, 4H), 7.18-7.05 (m, 5H), 6.68 (d, J=3.2 Hz, 1H), 4.91-4.87 (m, 1H), 4.72 (d, J=6 Hz, 2H), 4.08-4.01 (m, 1H), 3.85-3.79 (m, 1H), 2.37-2.29 (m, 1H), 2.18-2.15 (m, 1H).

Example 71

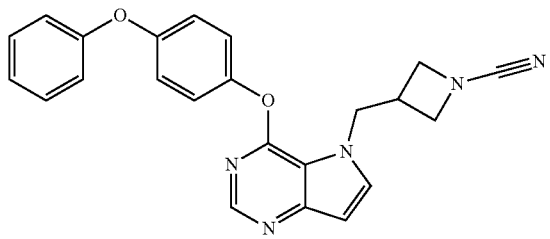 [SMILES: N#CN1CC(Cn2ccc3ncnc(Oc4ccc(Oc5ccccc5)cc4)c32)C1]

3-[[4-(4-phenoxyl)oxy)-5H-pyrrolo[3,2-d]pyrimidin-5-yl]methyl]azetidine-1-carbonitrile (66)

At RT, to a solution of 3-[[4-(4-phenoxyphenoxy)-5H-pyrrolo[3,2-d]pyrimidin-5-yl]methyl]azetidine (510 mg, 1.37 mmol, 1.00 equiv) in dichloromethane/water (3:1, 10 mL) was added sodium bicarbonate (460 mg, 5.48 mmol, 4.00 equiv). This was followed by the addition of carbononitridic bromide (173 mg, 1.63 mmol, 1.20 equiv). The resulting solution was stirred overnight at RT. The reaction mixture was quenched by 10 mL water and extracted with 3×20 mL dichloromethane. The organic phases were combined, dried over anhydrous sodium sulfate and concentrated under reduced pressure. The crude product was purified by Prep HPLC with the following conditions: XBridge Prep C18 OBD Column, 19×150 mm, 5 um; MeCN in water (with 10 mM NH4HCO3), 30% to 70% gradient in 10 min. 3-[[4-(4-phenoxyphenoxy)-5H-pyrrolo[3,2-d]pyrimidin-5-yl]methyl]azetidine-1-carbonitrile was obtained as a white solid (30 mg, 15% for 3 steps). HPLC: 99.5%, RT=1.917 min. MS: m/z=398.3 [M+H]+. 1H-NMR (400 MHz, DMSO-d6) δ 8.33 (s, 1H), 7.91 (d, J=4 Hz, 1H), 7.45-7.35 (m, 4H), 7.18-7.06 (m, 5H), 6.67 (d, J=4 Hz, 1H), 4.53-4.42 (m, 2H), 3.52-3.49 (m, 1H), 3.48-3.37 (m, 2H), 3.35-3.18 (m, 1H), 2.91-2.84 (m, 1H), 1.91-1.83 (m, 1H), 1.72-1.65 (m, 1H).

Example 72

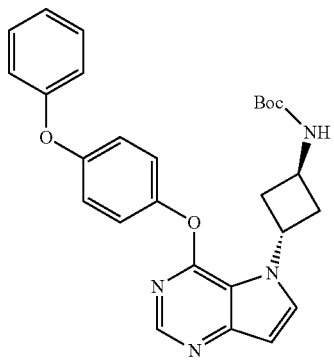 [SMILES: CC(C)(C)OC(=O)N[C@H]1C[C@H](n2ccc3ncnc(Oc4ccc(Oc5ccccc5)cc4)c32)C1]

tert-butyl N-[(1R,3R)-3-[4-(4-phenoxyphenoxy)-5H-pyrrolo[3,2-d]pyrimidin-5-yl]cyclobutyl]carbamate At 0° C., to a solution of 4-(4-phenoxyphenoxy)-5H-pyrrolo[3,2-d]pyrimidine (607.0 mg, 2.00 mmol, 1.00 equiv) in THF (20 mL) were added tert-butyl N-[(1S,3S)-3-hydroxycyclobutyl]carbamate (374.70 mg, 2.00 mmol, 1.00 equiv) and PPh3 (524.89 mg, 2.00 mmol, 1.00 equiv). This was followed by the slow addition of DIAD (404.66 mg, 2.00 mmol, 1.00 equiv) at 0° C. The resulting solution was stirred overnight at 50° C. in an oil bath. The reaction mixture was concentrated under reduced pressure. The residue was purified in a silica gel column eluting with a gradient of 10-40% EtOAC in hexane to yield tert-butyl N-[(1R,3R)-3-[4-(4-phenoxyphenoxy)-5H-pyrrolo[3,2-d]pyrimidin-5-yl]cyclobutyl]carbamate as a colorless syrup (1.3 g).

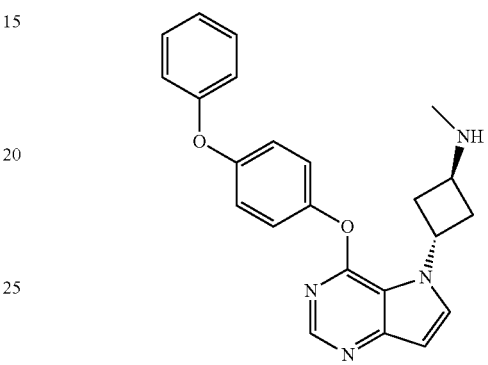

(1R,3R)—N-methyl-3-[4-(4-phenoxyphenoxy)-5H-pyrrolo[3,2-d]pyrimidin-5-yl]cyclobutan-1-amine At RT, tert-butyl N-[(1R,3R)-3-[4-(4-phenoxyphenoxy)-5H-pyrrolo[3,2-d]pyrimidin-5-yl]cyclobutyl]carbamate (940 mg, 1.99 mmol, 1.00 equiv) was dissolved in THF (15 mL). This was followed by the addition of LiAlH4 (150 mg, 3.95 mmol, 2.00 equiv) in portions over 1 min period. The resulting solution was stirred for 3 h at 60° C. The reaction was then quenched by 20 mL water. The pH value of the mixture was adjusted to 3 with HCl solution (2 M). Then the mixture was extracted with 3×50 mL of ethyl acetate. The pH value of the aqueous phase was adjusted back to 10 with sodium hydroxide solution (2 M). Then the aqueous solution was extracted with 2×30 mL of DCM/MeOH=30:1. The organic phases were combined, dried over anhydrous sodium sulfate and concentrated under reduced pressure to yield (1R,3R)—N-methyl-3-[4-(4-phenoxyphenoxy)-5H-pyrrolo[3,2-d]pyrimidin-5-yl]cyclobutan-1-amine as a orange syrup (280 mg, 36% for two steps).

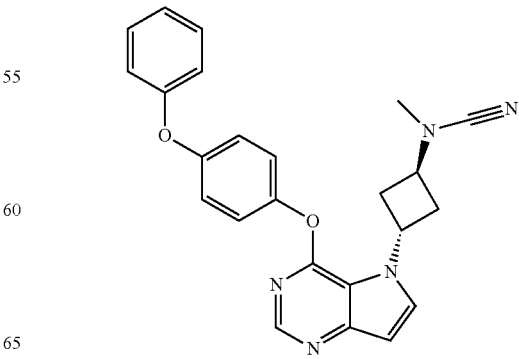

(1R,3R)—N-cyano-N-methyl-3-[4-(4-phenoxyphenoxy)-5H-pyrrolo[3,2-d]pyrimidin-5-yl]cyclobutan-1-amine (67)

To a solution of (1R,3R)—N-methyl-3-[4-(4-phenoxyphenoxy)-5H-pyrrolo[3,2-d]pyrimidin-5-yl]cyclobutan-1-amine (250.00 mg, 0.65 mmol, 1.00 equiv) in dichloromethane/water (3:1, 10 mL) was added sodium bicarbonate (217.38 mg, 2.59 mmol, 4.00 equiv) at RT. This was followed by the addition of carbononitridic bromide (82.23 mg, 0.78 mmol, 1.20 equiv). The resulting solution was stirred overnight at RT. The reaction mixture was quenched by 10 mL water and extracted with 3×20 mL dichloromethane. The organic phases were combined, dried over anhydrous sodium sulfate and concentrated under reduced pressure. The crude product (250 mg) was purified by Prep HPLC with the following conditions: XBridge Prep C18 OBD Column, 19×150 mm, 5 um; MeCN in water (with 10 mM NH$_4$HCO$_3$), 25% to 75% gradient in 12 min. (1R,3R)—N-cyano-N-methyl-3-[4-(4-phenoxyphenoxy)-5H-pyrrolo[3,2-d]pyrimidin-5-yl]cyclobutan-1-amine was obtained as a yellow solid (40 mg, 15%). HPLC: 99.0%, RT=1.948 min. MS: m/z=412.3 [M+H]$^+$. $^1$H-NMR (400 MHz, CDCl$_3$) δ 8.51 (s, 1H), 7.58 (d, J=3.2 Hz, 1H), 7.58 (d, J=3.2 Hz, 1H), 7.38 (t, J=8.0 Hz, 2H), 7.28-7.21 (m, 2H), 7.17-7.09 (m, 5H), 6.75 (d, J=3.2 Hz, 1H), 5.65-5.57 (m, 1H), 3.84-3.78 (m, 1H), 2.97-2.85 (m, 7H).

Example 73

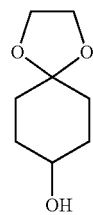

1,4-dioxaspiro[4.5]decan-8-ol

At RT, 1,4-dioxaspiro[4.5]decan-8-one (5.00 g, 32.01 mmol, 1.00 equiv) was dissolved in THF (50 mL). This was followed by the addition of LiAlH$_4$ (1.22 g, 32.14 mmol, 1.00 equiv) in portions at 0° C. over 5 min period. The mixture was then stirred for 2 h at 0° C. The reaction was then quenched by the addition of 10 mL water. The pH value of this mixture was adjusted to 1.0 with HCl solution (2 M), which was extracted with 3×100 mL ethyl acetate. The organic phases were combined and washed with 2×50 mL brine, dried over anhydrous sodium sulfate and concentrated under reduced pressure to yield 1,4-dioxaspiro[4.5]decan-8-ol as colorless oil (3.2 g, 63%).

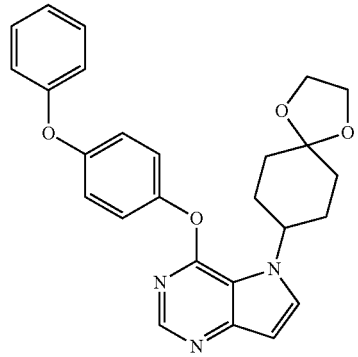 [SMILES: c1ccc(Oc2ccc(Oc3ncnc4ccn(C5CCC6(CC5)OCCO6)c34)cc2)cc1]

5-[1,4-dioxaspiro[4.5]decan-8-yl]-4-(4-phenoxyphenoxy)-5H-pyrrolo[3,2-d]pyrimidine At 0° C., to a solution of 4-(4-phenoxyphenoxy)-5H-pyrrolo[3,2-d]pyrimidine (607.0 mg, 2.0 mmol, 1.0 equiv) in THF (25 mL) were added 1,4-dioxaspiro[4.5]decan-8-ol (949.75 mg, 6.00 mmol, 3.00 equiv) and PPh$_3$ (1.57 mg, 6.00 mmol, 3.00 equiv). This was followed by the dropwise addition of DIAD (1.21 g, 6.00 mmol, 3.00 equiv) in tetrahydrofuran (5 mL) at 0° C. The resulting solution was stirred overnight at RT. The reaction mixture was concentrated under reduced pressure to yield 5-[1,4-dioxaspiro[4.5]decan-8-yl]-4-(4-phenoxyphenoxy)-5H-pyrrolo[3,2-d]pyrimidine as a white solid (1.7 g, crude).

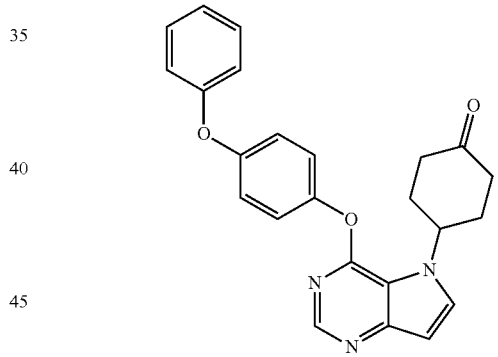

4-[4-(4-phenoxyphenoxy)-5H-pyrrolo[3,2-d]pyrimidin-5-yl]cyclohexan-1-one

At RT, to a solution of 5-[1,4-dioxaspiro[4.5]decan-8-yl]-4-(4-phenoxyphenoxy)-5H-pyrrolo[3,2-d]pyrimidine (1.4 g, 3.16 mmol, 1.00 equiv) in THF/water (1:1, 30 mL) was added hydrogen chloride solution (2 mL, 12 N). The resulting solution was stirred overnight at 50° C. The reaction mixture was concentrated under reduced pressure. The residue was diluted with 10 mL H$_2$O, the pH value of which was adjusted to 10 using sodium hydroxide solution (2 M). The mixture was extracted with 2×30 mL of dichloromethane and the organic phases were combined, dried over anhydrous sodium sulfate and concentrated under reduced pressure. The residue was purified in a silica gel column eluting with a gradient of 5%-30% EtOAC in hexane to yield 4-[4-(4-phenoxyphenoxy)-5H-pyrrolo[3,2-d]pyrimidin-5-yl]cyclohexan-1-one as a white solid (1.5 g).

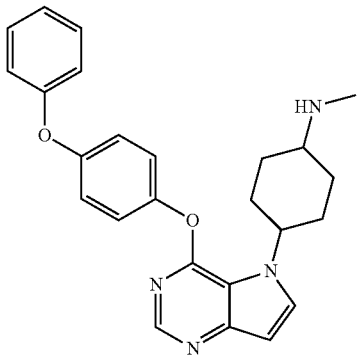 [SMILES: CNC1CCC(n2ccc3ncnc(Oc4ccc(Oc5ccccc5)cc4)c32)CC1]

N-methyl-4-[4-(4-phenoxyphenoxy)-5H-pyrrolo[3,2-d]pyrimidin-5-yl]cyclohexan-1-amine At RT, to a solution of 4-[4-(4-phenoxyphenoxy)-5H-pyrrolo[3,2-d]pyrimidin-5-yl]cyclohexan-1-one (400.00 mg, 1.00 mmol, 1.00 equiv) in methanol (10 mL) was added AcOH (30 mg, 0.50 mmol, 0.50 equiv), followed by the addition of methanamine (124 mg, 3.99 mmol, 4.00 equiv). The resulting solution was stirred for 4 h at RT. Then NaBH$_4$ (75.77 mg, 2.00 mmol, 2.00 equiv) was added and the mixture was kept stirring overnight at RT. The reaction mixture was concentrated under reduced pressure. The residue was purified in a silica gel column eluting with a gradient of 5%-35% methanol in dichloromethane to yield N-methyl-4-[4-(4-phenoxyphenoxy)-5H-pyrrolo[3,2-d]pyrimidin-5-yl]cyclohexan-1-amine as a white solid (300 mg, 36% for 3 steps).

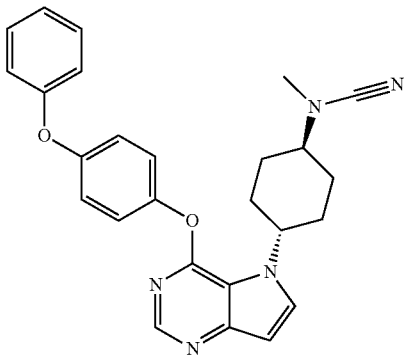 [SMILES: CN(C#N)[C@H]1CC[C@H](n2ccc3ncnc(Oc4ccc(Oc5ccccc5)cc4)c32)CC1]

(1R,4R)—N-cyano-N-methyl-4-[4-(4-phenoxyphenoxy)-5H-pyrrolo[3,2-d]pyrimidin-5-yl]cyclohexan-1-amine (70)

To a solution of (N-methyl-4-[4-(4-phenoxyphenoxy)-5H-pyrrolo[3,2-d]pyrimidin-5-yl]cyclohexan-1-amine (290.00 mg, 0.70 mmol, 1.00 equiv) in dichloromethane/water (3:1, 8 mL) was added sodium bicarbonate (117.55 mg, 1.40 mmol, 2.00 equiv) at RT. This was followed by the addition of carbononitridic bromide (88.93 mg, 0.84 mmol, 1.20 equiv). The resulting solution was stirred overnight at RT. The reaction mixture was quenched by 10 mL water and extracted with 3×20 mL dichloromethane. The organic phases were combined, dried over anhydrous sodium sulfate and concentrated under reduced pressure. The residue was purified by Prep HPLC with the following conditions: XBridge Prep C18 OBD Column, 19×150 mm, 5 um; MeCN in water (with 0.05% TFA), 30% to 70% gradient in 10 min. Crude product (120 mg) was obtained, which was purified again by chiral-Prep HPLC with the following conditions: Phenomenex Lux 5u Cellulose-4AXIA Packed column, 250×21.2 mm, 5 um; ethanol in hexane (50.0% isocratic in 30 min). (1R,4R)—N-cyano-N-methyl-4-[4-(4-phenoxyphenoxy)-5H-pyrrolo[3,2-d]pyrimidin-5-yl]cyclohexan-1-amine was obtained (14 mg, 5%). HPLC: 99.5%, RT=3.382 min. MS: m/z=440.1 [M+H]$^+$. $^1$H-NMR (400 MHz, CD$_3$OD) δ 8.37 (br, 1H), 7.93 (d, J=2.4 Hz, 1H), 7.36-7.40 (m, 2H), 7.05-7.16 (m, 5H), 6.69 (s, 1H), 4.99-4.92 (m, 1H), 3.34-3.31 (m, 1H), 2.90 (s, 3H), 2.29-2.21 (m, 4H), 2.13-2.11 (m, 2H), 1.93-1.85 (m, 2H).

Example 74

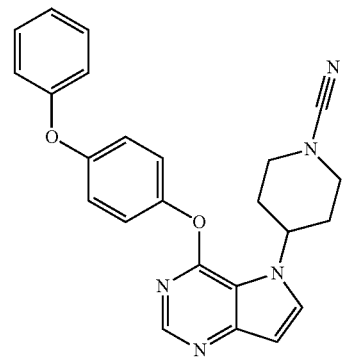 [SMILES: N#CN1CCC(n2ccc3ncnc(Oc4ccc(Oc5ccccc5)cc4)c32)CC1]

4-(4-(4-phenoxyphenoxy)-5H-pyrrolo[3,2-d]pyrimidin-5-yl)piperidine-1-carbonitrile (56) (Method N)

In a microwave vial containing 4-(4-Phenoxy-phenoxy)-5-piperidin-4-yl-5H-pyrrolo[3,2-d]pyrimidine (110.00 mg; 0.28 mmol; 1.00 eq.), Cyanogen bromide (83.58 μl; 1.14 mmol; 4.00 eq.) in DCM (5.00 ml; 78.00 mmol; 274.04 eq.) was added DIPEA (0.28 ml; 1.71 mmol; 6.00 eq.). The reaction was stirred at rt for 16 h before it was concentrated, diluted with 5 mL EtOH and filtered. The collected cake was dried to afford 4-(4-(4-phenoxyphenoxy)-5H-pyrrolo[3,2-d]pyrimidin-5-yl)piperidine-1-carbonitrile (80.0 mg, 68.3%) as off-white solid. HPLC: 100%. MS: m/z=412 [M+H]$^+$. $^1$H-NMR (DMSO-D6) δ 8.34 (s, 1H), 8.08 (d, 1H), 7.30-7.44 (m, 4H), 7.07-7.22 (m, 5H), 6.69 (d, 1H), 4.95 (m, 1H), 3.54 (d, 2H), 3.25 (m, 2H), 2.20 (m, 4H).

Example 75

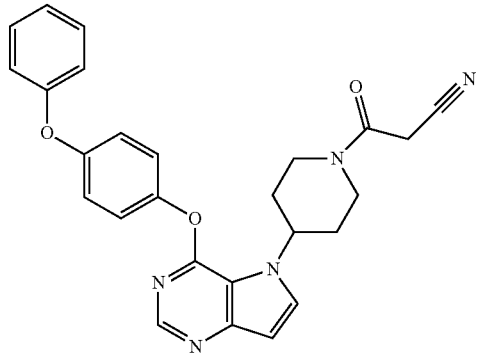 [SMILES: N#CCC(=O)N1CCC(n2ccc3ncnc(Oc4ccc(Oc5ccccc5)cc4)c32)CC1]

3-oxo-3-(4-(4-(4-phenoxyphenoxy)-5H-pyrrolo[3,2-d]pyrimidin-5-yl)piperidin-1-yl)propanenitrile The titled compound was made using 4-(4-Phenoxy-phenoxy)-5-piperidin-4-yl-5H-pyrrolo[3,2-d]pyrimidine, Cyano-acetic acid, Triethyl amine and 2,4,6-Tripropyl-[1,3,5,2,4,6]trioxatriphosphinane using conditions similar to those used in methods A, C, E, and G described above. MS: m/z=454[M+H]$^+$.

Example 76

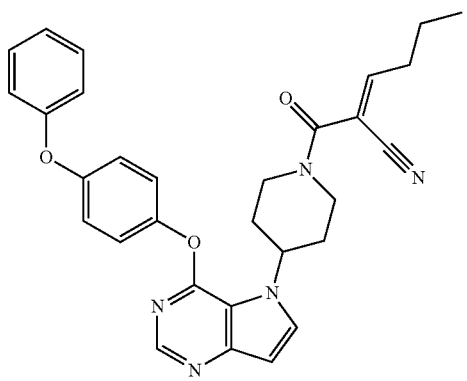 [SMILES: CCC/C=C(\C#N)C(=O)N1CCC(n2ccc3ncnc(Oc4ccc(Oc5ccccc5)cc4)c32)CC1]

(E)-2-(4-(4-(4-phenoxyphenoxy)-5H-pyrrolo[3,2-d]pyrimidin-5-yl)piperidine-1-carbonyl)hex-2-enenitrile (55)

To a stirred solution of 3-Oxo-3-{4-[4-(4-phenoxy-phenoxy)-pyrrolo[3,2-d]pyrimidin-5-yl]-piperidin-1-yl}-propionitrile (0.50 g; 0.57 mmol; 1.00 eq.) in dry DCM (6.65 g; 5.00 ml; 10.00 V) was added Butyraldehyde (0.06 g; 0.86 mmol; 1.50 eq.) followed by Piperazine (0.00 g; 0.06 mmol; 0.10 eq.) at RT. The reaction mixture was stirred at RT for 8 h. The reaction was monitored by TLC. After completion, the reaction mixture was diluted with water, the organic layer was washed with brine, and dried over anhydrous sodium sulphate. The crude product was purified with column chromatography (60-120 silica) using pet ether and ethyl acetate as eluent (50-60%) to afford (E)-2-{4-[4-(4-Phenoxy-phenoxy)-pyrrolo[3,2-d]pyrimidin-5-yl]-piperidine-1-carbonyl}-hex-2-enenitrile (70.00 mg; 0.10 mmol; 16.6%; pale yellow gummy; Purified Product). MS: m/z=508[M+H]$^+$. 1H NMR (400 MHz, DMSO-d6): 8.52 (s, 1H), 7.55-7.54 (m, 1H), 7.40-7.36 (m, 2H), 7.27-7.20 (m, 3H), 7.19-7.13 (m, 4H), 6.80 (t, J=8.00 Hz, 1H), 5.13 (t, J=4.00 Hz, 1H), 5.90-5.80 (m, 1H), 4.20-4.10 (m, 1H), 3.30-3.10 (m, 1H), 2.90-2.80 (m, 1H), 2.55-2.50 (m, 2H), 2.38-2.31 (m, 2H), 2.11-2.08 (m, 2H), 1.64-1.55 (m, 2H), 1.03-0.92 (m, 3H).

Example 77

(E)-4-(4-(2-((tert-butoxycarbonyl)amino)ethyl)piperazin-1-yl)but-2-enoic acid

To a stirred solution of 1-2-N-Boc-(aminoethyl)-Piperazine (2.00 g; 8.63 mmol; 1.00 eq.) and Triethyl-amine (2.65 g; 3.65 ml; 25.90 mmol; 3.00 eq.) in dry THF (17.80 g; 20.00 ml; 10.00 V) was added (E)-4-Bromo-but-2-enoic acid (1.74 g; 10.36 mmol; 1.20 eq.) at 0° C. under nitrogen atmosphere. After the addition, the reaction mixture was stirred at the same temperature for another 2 h. The reaction mixture was slowly allowed to RT for 18 h. After the completion, the precipitated solid was filtered, the solid was washed with THF (25 mL) and the filtrate was evaporated under high vacuum. The crude product was directly loaded to column (60-120 silica gel) using DCM and methanol as eluent (12-15%) to afford (E)-4-[4-(2-tert-Butoxycarbonylamino-ethyl)-piperazin-1-yl]-but-2-enoic acid (1.20 g; 3.48 mmol; 40.4%). MS: m/z=314[M+H]$^+$ (TIC).

tert-butyl (E)-(2-(4-(4-oxo-4-(4-(4-(4-phenoxyphenoxy)-5H-pyrrolo[3,2-d]pyrimidin-5-yl)piperidin-1-yl)but-2-en-1-yl)piperazin-1-yl)ethyl)carbamate To a stirred solution of 4-(4-Phenoxy-phenoxy)-5-piperidin-4-yl-5H-pyrrolo[3,2-d]pyrimidine (0.80 g; 1.80 mmol; 1.00 eq.) in dry DCM (10.64 g; 8.00 ml; 10.00 V) was added (E)-4-[4-(2-tert-Butoxycarbonylamino-ethyl)-piperazin-1-yl]-but-2-enoic acid (0.67 g; 1.98 mmol; 1.10 eq.) followed by Triethyl-amine (0.55 g; 5.40 mmol; 3.00 eq.) at RT. The reaction mixture was cooled to 0° C. and T3P was added (50% in Ethyl acetate) (1.72 g; 1.70 ml; 2.70 mmol; 1.50 eq.)

under nitrogen atmosphere. The reaction mixture was slowly allowed to warm to RT and stirred for 6 h. The reaction was monitored by TLC. After the completion, the reaction mixture was diluted with 10% NaHCO₃ solution. The organic layer was separated and washed with water, brine and dried over anhydrous sodium sulphate to afford {2-[4-((E)-4-Oxo-acetate (25 mL×3). The combined organic layer was washed with brine and evaporated under high vacuum to afford (E)-4-[4-(2-Amino-ethyl)-piperazin-1-yl]-1-{4-[4-(4-phenoxy-phenoxy)-pyrrolo[3,2-d]pyrimidin-5-yl]-piperidin-1-yl}-but-2-en-1-one (0.60 g; 0.77 mmol; 79.9%) MS: m/z=582[M+H]⁺.

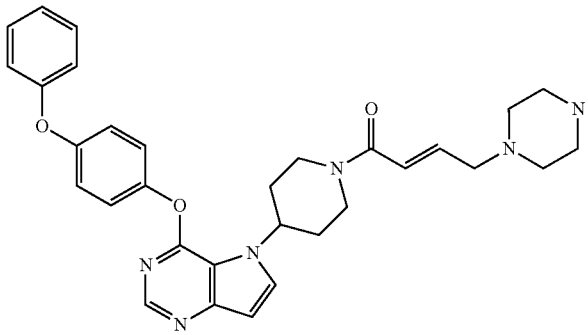

4-{4-[4-(4-phenoxy-phenoxy)-pyrrolo[3,2-d]pyrimidin-5-yl]-piperidin-1-yl}-but-2-enyl)-piperazin-1-yl]-ethyl}-carbamic acid tert-butyl ester (1.47 g; 1.47 mmol; 81.4%; colorless foam; Crude Product). MS: m/z=682[M+H]⁺.

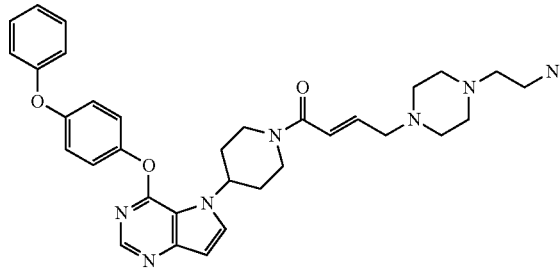 [SMILES: NCCN1CCN(C/C=C/C(=O)N2CCC(n3ccc4ncnc(Oc5ccc(Oc6ccccc6)cc5)c43)CC2)CC1]

(E)-4-(4-(2-aminoethyl)piperazin-1-yl)-1-(4-(4-(4-phenoxyphenoxy)-5H-pyrrolo[3,2-d]pyrimidin-5-yl) piperidin-1-yl)but-2-en-1-one A mixture of 4N HCl in 1,4-dioxane and {2-[4-((E)-4-Oxo-4-{4-[4-(4-phenoxy-phenoxy)-pyrrolo[3,2-d]pyrimidin-5-yl]-piperidin-1-yl}-but-2-enyl)-piperazin-1-yl]-ethyl}-carbamic acid tert-butyl ester (1.00 g; 0.00 mol; 1.00 eq.) was stirred at RT for 2 h. The reaction was monitored by TLC. After completion, the reaction mixture was concentrated under high vacuum. The residue was dissolved with water (25 mL) and the aqueous layer was washed with ethyl acetate (25 mL×3). The aqueous layer was basified (~PH=8), with NaHCO₃ (solid) and extracted with ethyl

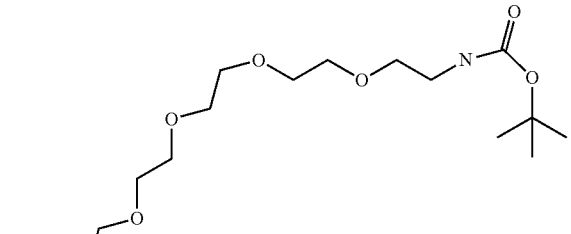

tert-butyl (E)-(15-oxo-18-(4-(4-oxo-4-(4-(4-(4-phenoxyphenoxy)-5H-pyrrolo[3,2-d]pyrimidin-5-yl) piperidin-1-yl)but-2-en-1-yl)piperazin-1-yl)-3,6,9,12-tetraoxa-16-azaoctadecyl)carbamate To a stirred solution of (E)-4-[4-(2-Amino-ethyl)-piperazin-1-yl]-1-{4-[4-(4-phenoxy-phenoxy)-pyrrolo[3,2-d]pyrimidin-5-yl]-piperidin-1-yl}-but-2-en-1-one (1.00 g; 1.29 mmol; 1.00 eq.) in dry DCM (13.30 g; 10.00 ml; 10.00 V) was added 3-(2-{2-[2-(2-tert-Butoxycarbonylamino-ethoxy)-ethoxy]-ethoxy}-ethoxy)-propionic acid (0.58 g; 1.55 mmol; 1.20 eq.) followed by Triethyl amine (0.40 g; 0.55 ml; 3.87 mmol; 3.00 eq.) at RT. The reaction mixture was cooled to 0-5° C. and T3P was added (50% in Ethyl acetate) (1.23 g; 1.22 ml; 1.93 mmol; 1.50 eq.). The reaction mixture was stirred at RT for 6 h. The reaction was monitored by TLC. The reaction mixture was diluted with 10% NaHCO₃ solution and extracted with DCM. The organic layer was washed with water (25 mL), brine (25 mL) and dried over anhydrous sodium sulphate. The crude product was purified by column chromatography (60-120 silica) using chloroform and methanol as eluent (2-5%) to afford [2-(2-{2-[2-(2-{2-[4-((E)-4-Oxo-4-{4-[4-(4-phenoxy-phenoxy)-pyrrolo[3,2-d]pyrimidin-5-yl]-piperidin-1-yl}-but-2-enyl)-piperazin-1-yl]-ethylcarbamoyl}-ethoxy)-ethoxy]-ethoxy}-ethyl]-carbamic acid tert-butyl ester (0.43 g; 0.43 mmol; 33.4%; colorless gum). MS: m/z=930[M+H]⁺. 1H NMR (400 MHz, DMSO-d6): 8.31 (s, 1H), 8.02 (d, J=4.00 Hz, 1H), 7.74 (t, J=4.00 Hz, 1H), 7.39-7.35 (m, 2H), 7.34-7.33 (m, 2H), 7.17-7.10 (m, 1H), 7.10-7.04 (m, 4H), 6.75-6.70 (m, 1H), 6.66-6.55 (m, 3H), 5.04-5.00 (m, 1H), 4.55-4.53 (m, 1H), 4.30-4.20 (m, 1H), 3.58-3.50 (m, 2H), 3.48-3.47 (m, 12H), 3.46-3.37 (m, 2H), 3.35-3.32 (m, 1H), 3.32-3.30 (m, 2H), 3.15-3.12 (m, 4H), 2.55-2.50 (m, 1H), 2.49-2.48 (m, 10H), 2.28-2.20 (m, 2H), 1.98-1.90 (m, 2H), 1.35 (s, 9H).

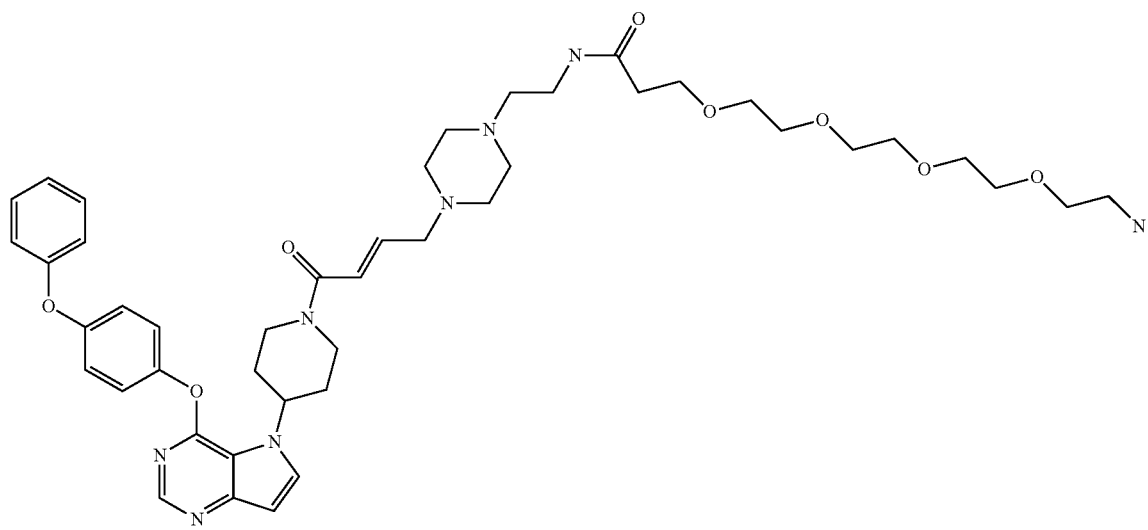

Exact Mass: 828.45
Molecular Weight: 829.00

(E)-1-amino-N-(2-(4-(4-oxo-4-(4-(4-(4-phenoxyphenoxy)-5H-pyrrolo[3,2-d]pyrimidin-5-yl)piperidin-1-yl)but-2-en-1-yl)piperazin-1-yl)ethyl)-3,6,9,12-tetraoxapentadecan-15-amide (73)

[2-(2-{2-[2-(2-{2-[4-((E)-4-Oxo-4-{4-[4-(4-phenoxy-phenoxy)-pyrrolo[3,2-d]pyrimidin-5-yl]-piperidin-1-yl}-but-2-enyl)-piperazin-1-yl]-ethylcarbamoyl}-ethoxy)-ethoxy]-ethoxy}-ethoxy)-ethyl]-carbamic acid tert-butyl ester (0.38 mmol; 1.00 eq.; 350.00 mg) was combined with 4N HCl in Dioxan (10.00 ml) and methanol (74.06 mmol; 196.60 eq.; 2373.00 mg; 3.00 ml). The mixture was stirred at RT for 1 hr. All solvent was then removed and the crude product was dried on highvac overnight to give 3-(2-{2-[2-(2-Amino-ethoxy)-ethoxy]-ethoxy}-ethoxy)-N-{2-[4-((E)-4-oxo-4-{4-[4-(4-phenoxy-phenoxy)-pyrrolo[3,2-d]pyrimidin-5-yl]-piperidin-1-yl}-but-2-enyl)-piperazin-1-yl]-ethyl}-propionamide (314.00 mg; 0.38 mmol) which was used without purification. MS: m/z=830[M+H]$^+$. $^1$H NMR (400 MHz, DMSO-d6) δ 8.45 (s, 1H), 8.22 (s, 2H), 8.15-8.04 (m, 2H), 7.88 (s, 4H), 7.58-7.30 (m, 1H), 7.30-6.93 (m, 2H), 6.80-6.51 (m, 2H), 5.12 (s, 2H), 4.65 (d, J=13.8 Hz, 2H), 4.28 (s, 1H), 4.00-3.15 (m, 16H), 3.07-2.71 (m, 6H), 2.44-2.15 (m, 5H), 2.02 (d, J=13.4 Hz, 1H).

Example 78

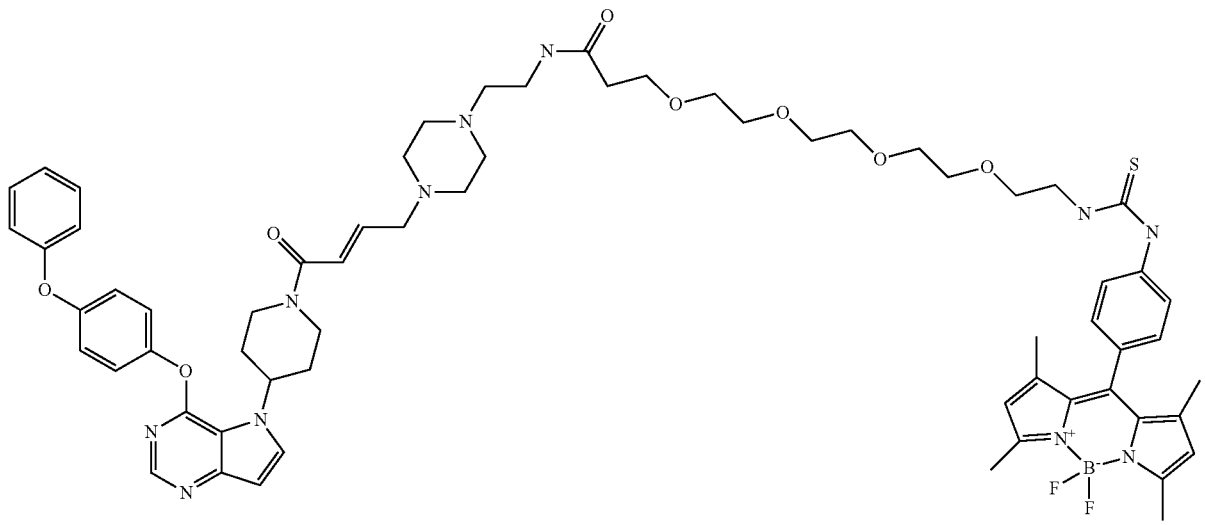 [SMILES: CC1=CC(C)=[N+]2C1=C(c1ccc(NC(=S)NCCOCCOCCOCCOCCC(=O)NCCN3CCN(C/C=C/C(=O)N4CCC(n5ccc6ncnc(Oc7ccc(Oc8ccccc8)cc7)c65)CC4)CC3)cc1)c1c(C)cc(C)n1[B-]2(F)F]

(E)-1-((4-(5,5-difluoro-1,3,7,9-tetramethyl-5H-414,
514-dipyrrolo[1,2-c:2',1'-f][1,3,2]diazaborinin-10-yl)
phenyl)amino)-N-(2-(4-(4-oxo-4-(4-(4-(4-phenoxy-
phenoxy)-5H-pyrrolo[3,2-d]pyrimidin-5-yl)
piperidin-1-yl)but-2-en-1-yl)piperazin-1-yl)ethyl)-1-
thioxo-5,8,11,14-tetraoxa-2-azaheptadecan-17-amide
(74)

3-(2-{2-[2-(2-Amino-ethoxy)-ethoxy]-ethoxy}-ethoxy)-
N-{2-[4-((E)-4-oxo-4-{4-[4-(4-phenoxy-phenoxy)-pyrrolo
[3,2-d]pyrimidin-5-yl]-piperidin-1-yl}-but-2-enyl)-piper-
azin-1-yl]-ethyl}-propionamide (0.07 mmol; 1.00 eq.; 59.00
mg) was combined with 5,5-difluoro-10-(4-isothiocyanato-
phenyl)-1,3,7,9-tetramethyl-5H-414,514-dipyrrolo[1,2-c:2',
1'-f][1,3,2]diazaborinine (0.08 mmol; 1.10 eq.; 29.85 mg),
N-Ethyldiisopropylamine (0.21 mmol; 3.00 eq.; 27.60 mg;
0.04 ml) and MeCN (38.29 mmol; 538.03 eq.; 1572.00 mg;
2.00 ml). The mixture was stirred at RT for 2 hrs. The crude
reaction was purified directly on reverse phase prep column
using a gradient of 20-80% CH3CN/H20 (formic acid 0.1%)
to give (E)-1-((4-(5,5-difluoro-1,3,7,9-tetramethyl-5H-414,
514-dipyrrolo[1,2-c:2',1'-f][1,3,2]diazaborinin-10-yl)phe-
nyl)amino)-N-(2-(4-(4-oxo-4-(4-(4-(4-phenoxyphenoxy)-
5H-pyrrolo[3,2-d]pyrimidin-5-yl)piperidin-1-yl)but-2-en-1-
yl)piperazin-1-yl)ethyl)-1-thioxo-5,8,11,14-tetraoxa-2-
azaheptadecan-17-amide (22.10 mg, 0.02 mmol, 23.8%) as
a yellow solid. MS: m/z=605[M+H/2]$^+$. 1H NMR (400
MHz, DMSO-d6): 8.31 (s, 1H), 8.02 (d, J=4.00 Hz, 1H),
7.74 (t, J=4.00 Hz, 1H), 7.39-7.35 (m, 4H), 7.34-7.33 (m,
6H), 7.17-7.10 (m, 1H), 7.10-7.04 (m, 4H), 6.75-6.70 (m,
1H), 6.66-6.55 (m, 3H), 5.04-5.00 (m, 1H), 4.55-4.53 (m,
1H), 4.30-4.20 (m, 1H), 3.58-3.50 (m, 2H), 3.48-3.47 (m,
12H), 3.46-3.37 (m, 2H), 3.35-3.32 (m, 1H), 3.32-3.30 (m,
2H), 3.15-3.12 (m, 4H), 2.55-2.50 (m, 1H), 2.49-2.48 (m,
23H), 2.28-2.20 (m, 2H), 1.98-1.90 (m, 2H).

Example 79

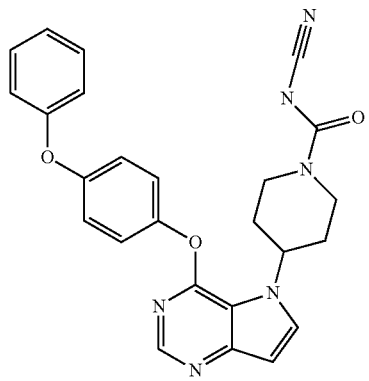 [SMILES: N#CNC(=O)N1CCC(n2ccc3ncnc(Oc4ccc(Oc5ccccc5)cc4)c32)CC1]

N-cyano-4-(4-(4-phenoxyphenoxy)-5H-pyrrolo[3,2-
d]pyrimidin-5-yl)piperidine-1-carboxamide (57)

Cyanamide (0.69 mmol; 2.10 eq.; 28.81 mg) was dis-
solved in THF then cooled to 0° C. on an icebath. NaH
(60%) (0.82 mmol; 2.50 eq.; 32.63 mg) was then added in
one portion and the mixture was stirred on the icebath under
nitrogen for 30 minutes. 4-[4-(4-Phenoxy-phenoxy)-pyrrolo
[3,2-d]pyrimidin-5-yl]-piperidine-1-carboxylic acid 4-nitro-
phenyl ester (0.33 mmol; 1.00 eq.; 179.98 mg) was then
added to the stirring solution and the icebath was removed.
The mixture was stirred at RT overnight. The crude reaction
was then quenched with saturated bicarb and extracted three
times with EtOAC. Sat NaCl solution was added and
extracted 3 additional times with EtOAC. The organics were
combined and then concentrated to dryness and purified via
reverse phase chromatography using 10-100% CH3CN/
H2O (0.1% Ammonium Hydroxide) to give N-cyano-4-(4-
(4-phenoxyphenoxy)-5H-pyrrolo[3,2-d]pyrimidin-5-yl)pip-
eridine-1-carboxamide. MS: m/z=455[M+H]$^+$. $^1$H-NMR
(MeOH-d4) δ 8.31 (s, 1H), 8.13 (s, 1H), 7.25 (m, 5H), 7.0
(m, 5H), 6.76 (d, 1H), 6.12 (d, 1H), 5.64 (d, 1H), 5.25 (s,
1H), 4.61 (d, 1H), 4.23 (d, 1H), 3.28 (m, 1H), 2.99 (t, 1H),
2.19 (m, 4H).

Example 80

BTK IC50 Enzyme Assay (Assay A)
The following describes a microfluidic, off-chip mobility
shift kinase assay used to measure inherent potency of
compounds against BTK enzyme.
2.5× stocks of full-length human BTK (08-080) from
CarnaBio USA, Inc., Natick, Mass., 1.6×ATP and appropri-
ate kinKDR peptide substrate (FITC-AHA-EEPLYWSF-
PAKKK10 NH2) were prepared in kinase reaction buffer
consisting of 25 mM MgCl2, 0.015% Brij-35 (30%), 100
mM Hepes, pH 7.5, and 10 mM DTT.
5 uL of enzyme buffer and 7.5 uL of ATP/kinKDR peptide
substrate mix were added to Matrix (#115304) 384-well,
sterile, polypropylene plates (Thermo Fisher Scientific, 15
Hudson, N.H.) with 125 nL of serially diluted compounds
prepared in 100% DMSO, and incubated for 90 min. at 27°
C. Following the incubation period, reactions were stopped
by adding 60 uL stop buffer consisting of 100 mM Hepes,
pH 7.5, 0.015% Brij-35 (30%), 0.277% Coating Reagent #3
(Caliper Life Sciences, Mountain View, Calif.), 5% DMSO.
Stopped reactions were monitored at −2 PSI, −3000 V/−700
V in a LabChip 3000 plate 20 reader from Caliper Life
Sciences, a PerkinElmer Company (Hopkinton, Mass.), and
the activity was measured by off-chip mobility shift assay
measuring the charge/mass difference between substrate and
product resulting from peptide phosphorilation. IC50 and
efficacy were determined by plotting log [Inhibitor] vs. %
Activity in GeneData Screener (Basel, Switzerland).
Assay B:
Btk is critical for mediating the signalling of B cell
antigen receptor (BCR) after anti-IgM stimulation. Based on
this principle, a functional cell-based assay was established
to determine the potency of compounds at inhibiting anti-
IgM-induced expression of CD69, a downstream BCR sig-
nalling event, in freshly isolated human peripheral blood
mononuclear cells (PBMCs). In the assay, a 90 μl PBMC
suspension containing 2.5×10$^5$ cells was pre-treated with 10
μl of test compound at various concentrations for an hour,
and then incubated overnight (approximately 16-18 hours)
with 5 μl 420 μg/ml affiniPure F(ab')2 fragment goat anti-
human IgM Fc fragment per well (Dianova, Cat. No.:
109-006-129). After the incubation, the cells were washed
and immunostained with an APC labelled mouse anti-human
CD69 (BD Biosciences; clone: FN50), a PerCP-Cy5.5
labelled mouse anti-human CD19 (BD Biosciences; clone:
SJ25C1) and a FITC-labelled mouse anti-human CD3 (BD
Biosciences; clone: HIT3a), and fixed for flow cytometric
analysis of CD69 expression on CD19 positive cells (B
cells). The percentage of CD69 expressing CD19 positive
cells was plotted against the concentrations of test compounds to obtain a concentration response curve, and calculate an $IC_{50}$ value as a measure of the potency of test compounds in the assay.

The data is interpreted according to the following:
+>5 µM;
++>1-5 µM;
+++>0.1-1 µM;
++++<0.1 µM.

| Compound number | Assay A | Assay B (mol/L (M)) |
|---|---|---|
| 1 | ++++ | |
| 2 | ++++ | |
| 3 | ++++ | ++++ |
| 4 | ++++ | |
| 5 | ++++ | |
| 6 | ++++ | |
| 7 | ++++ | |
| 8 | ++++ | |
| 9 | ++++ | |
| 10 | ++++ | +++ |
| 11 | ++++ | |
| 12 | ++++ | |
| 13 | ++++ | +++ |
| 14 | ++++ | |
| 15 | ++++ | |
| 16 | ++++ | |
| 17 | ++++ | |
| 18 | ++++ | |
| 19 | ++++ | |
| 20 | ++++ | |
| 21 | ++++ | |
| 22 | ++++ | |
| 23 | ++++ | |
| 24 | ++++ | |
| 25 | ++++ | |
| 26 | ++++ | |
| 27 | ++++ | |
| 28 | ++++ | |
| 29 | ++++ | |
| 30 | ++++ | |
| 31 | ++++ | ++ |
| 32 | +++ | |
| 33 | +++ | |
| 34 | +++ | |
| 35 | +++ | |
| 36 | +++ | |
| 37 | +++ | |
| 38 | +++ | |
| 39 | +++ | |
| 40 | +++ | |
| 41 | +++ | |
| 42 | ++ | |
| 43 | ++ | |
| 44 | ++ | |
| 45 | ++ | |
| 46 | ++ | |
| 47 | + | |
| 48 | + | |
| 49 | + | |
| 50 | + | |
| 51 | + | |
| 52 | +++ | |
| 55 | ++ | |
| 56 | ++ | |
| 57 | +++ | |
| 58 | ++ | |
| 59 | + | |
| 60 | ++++ | +++ |
| 61 | ++ | |
| 62 | ++ | |
| 63 | + | |
| 64 | +++ | |
| 65 | ++ | |
| 66 | ++ | |
| 67 | +++ | |
| 68 | ++ | |
| 69 | ++ | |
| 70 | +++ | |
| 71 | + | |
| 72 | ++++ | +++ |
| 73 | ++++ | |
| 74 | +++ | |
| 75 | + | |
| 76 | +++ | |
| 77 | | |

Example 81

Pharmaceutical Preparations (A) Injection vials: A solution of 100 g of an active ingredient according to the invention and 5 g of disodium hydrogen phosphate in 3 l of bidistilled water is adjusted to pH 6.5 using 2 N hydrochloric acid, sterile filtered, transferred into injection vials, is lyophilized under sterile conditions and is sealed under sterile conditions. Each injection vial contains 5 mg of active ingredient.

(B) Suppositories: A mixture of 20 g of an active ingredient according to the invention is melted with 100 g of soy lecithin and 1400 g of cocoa butter, is poured into moulds and is allowed to cool. Each suppository contains 20 mg of active ingredient.

(C) Solution: A solution is prepared from 1 g of an active ingredient according to the invention, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilized by irradiation. This solution could be used in the form of eye drops.

(D) Ointment: 500 mg of an active ingredient according to the invention is mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

(F) Coated tablets: Tablets are pressed analogously to Example E and subsequently are coated in a conventional manner with a coating of sucrose, potato starch, talc, tragacanth and dye.

(G) Capsules: 2 kg of an active ingredient according to the invention are introduced into hard gelatin capsules in a conventional manner in such a way that each capsule contains 20 mg of the active ingredient.

(H) Ampoules: A solution of 1 kg of an active ingredient according to the invention in 60 l of bidistilled water is sterile filtered, transferred into ampoules, is lyophilized under sterile conditions and is sealed under sterile conditions. Each ampoule contains 10 mg of active ingredient.

(I) Inhalation spray: 14 g of an active ingredient according to the invention are dissolved in 10 l of isotonic NaCl solution, and the solution is transferred into commercially available spray containers with a pump mechanism. The solution could be sprayed into the mouth or nose. One spray shot (about 0.1 ml) corresponds to a dose of about 0.14 mg.

While a number of embodiments of this invention are described herein, it is apparent that the basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound of formula I,

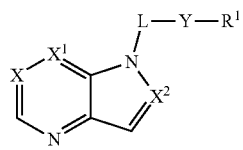

I or a pharmaceutically acceptable salt thereof, wherein:
X is N;
$X^1$ is $CR^2$;
$X^2$ is N or $CR^2$;
each $R^2$ is independently selected from —R, halogen, -haloalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —$NRSO_2R$, or —N(R)$_2$;
each R is independently hydrogen, $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or
two R groups on the same atom are taken together with the atom to which they are attached to form a $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;
L is a divalent group selected from $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, and a 5-6 membered monocyclic heteroaryl ring having 1-4 heteroatoms independently selected from nitrogen, oxygen, or sulfur; each of which is optionally substituted; or L is a divalent group selected from $C_{1-6}$ aliphatic-$C_{3-10}$ aryl, $C_{1-6}$ aliphatic-3-8 membered saturated or partially unsaturated carbocyclic ring, $C_{1-6}$ aliphatic-3-7 membered heterocylic ring having 1-4 heteroatoms independently selected from nitrogen, oxygen, or sulfur, and a $C_{1-6}$ aliphatic-5-6 membered monocyclic heteroaryl ring having 1-4 heteroatoms independently selected from nitrogen, oxygen, or sulfur; each of which is optionally substituted;
Y is O, S, $SO_2$, SO, C(O), $CO_2$, C(O)N(R), —NRC(O), —NRC(O)N(R), —$NRSO_2$, or N(R); or Y is absent; and $R^1$ is $C_{2-6}$ alkenyl or $C_{2-6}$ alkynyl, which is optionally substituted; or $R^1$ is CN.

2. The compound of claim 1, wherein each $R^2$ is independently phenyl or pyrazolyl.

3. The compound of claim 1, wherein each $R^2$ is independently —OR or —N(R)$_2$.

4. The compound of claim 1, wherein each $R^2$ is independently hydrogen,

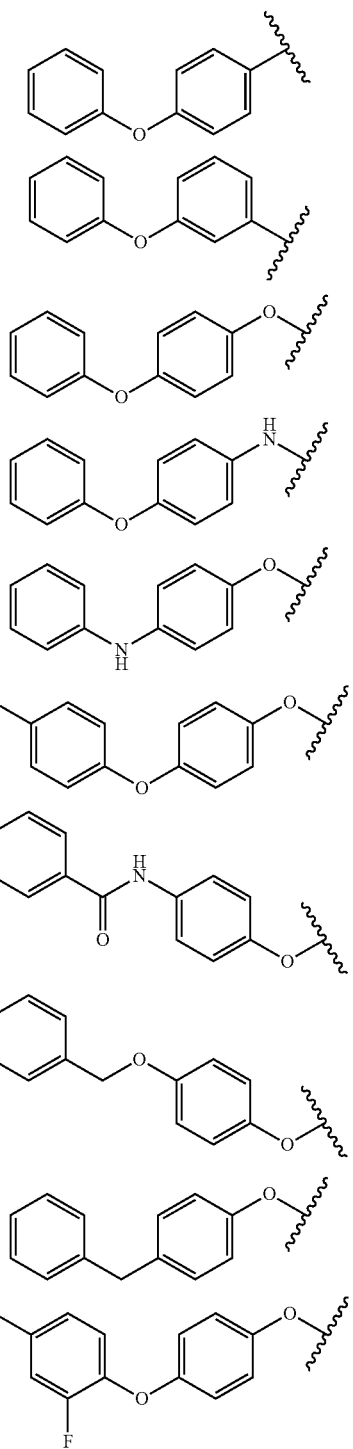

-continued
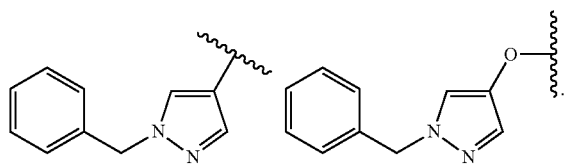
5. The compound of claim 1, wherein L is
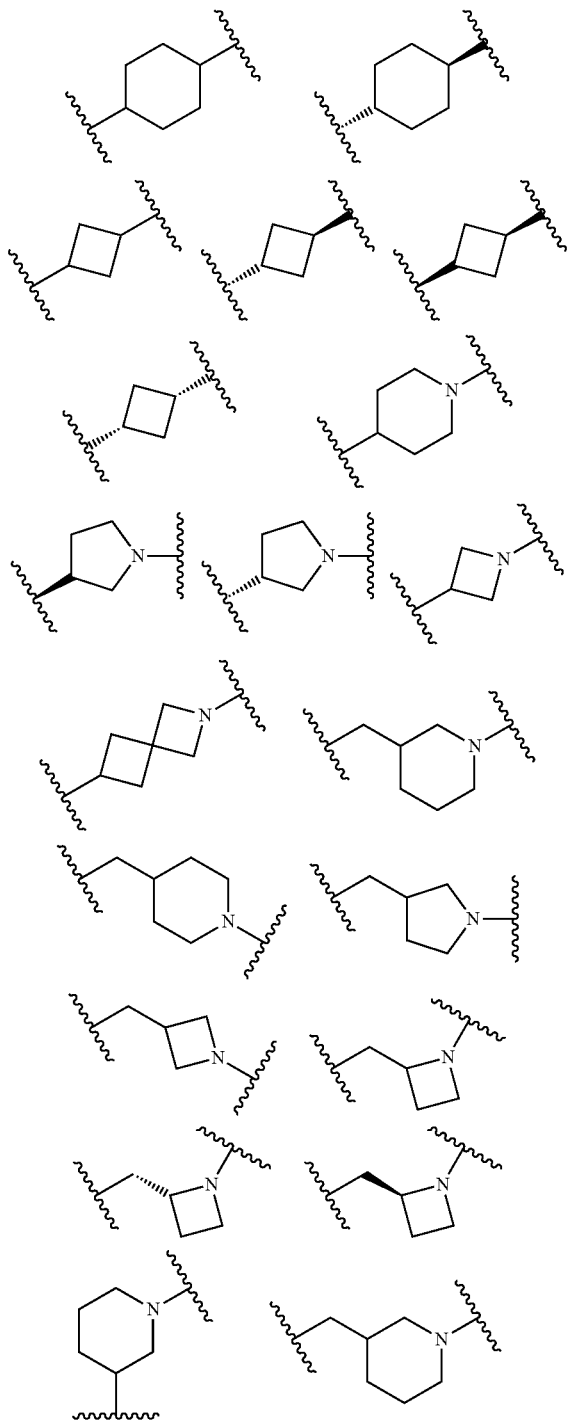
-continued
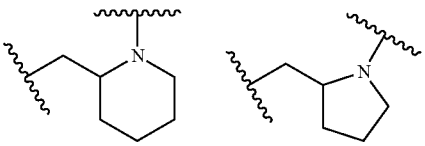
6. The compound of claim 1, wherein Y is NR,
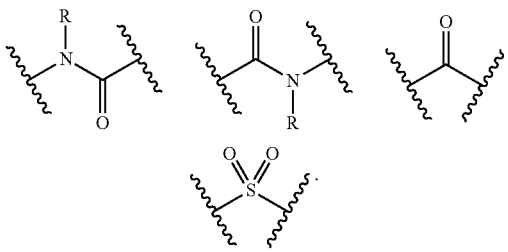
7. The compound of claim 1, wherein Y is absent.
8. The compound of claim 1, wherein $R^1$ is —CN, —CH$_2$CN,
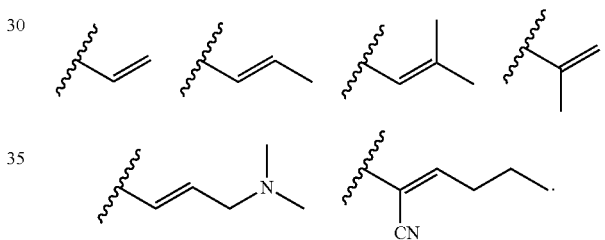
9. The compound of claim 1, of formula I-a1,
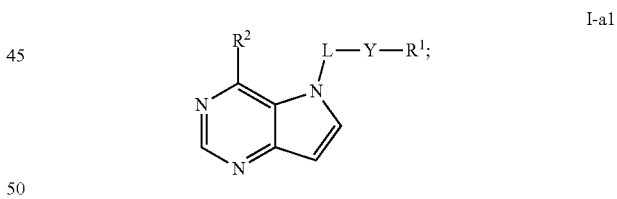
I-a1
or a pharmaceutically acceptable salt thereof.
10. The compound of claim 1, of formula I-a2,
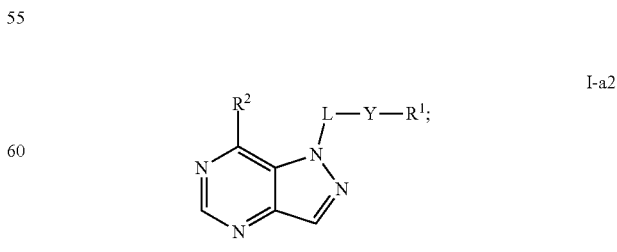
I-a2
or a pharmaceutically acceptable salt thereof.

11. The compound of claim 1, selected from
1
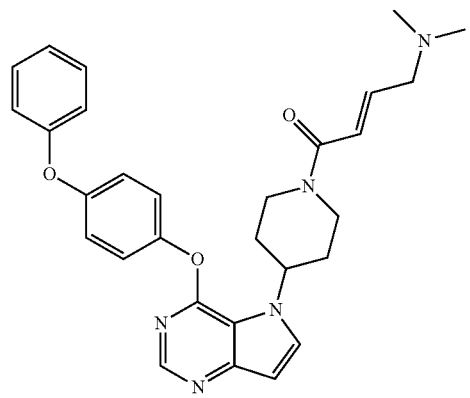
2
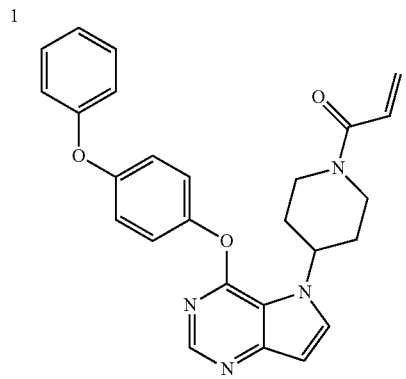
3
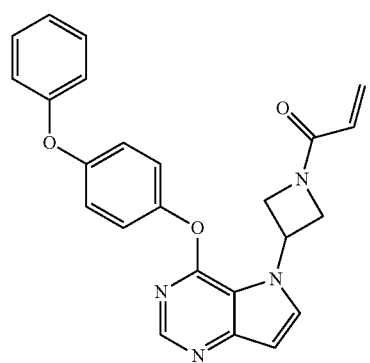
5
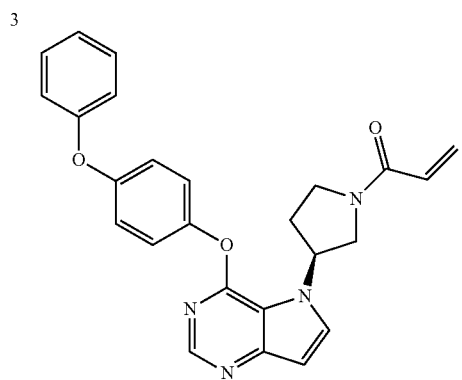
6
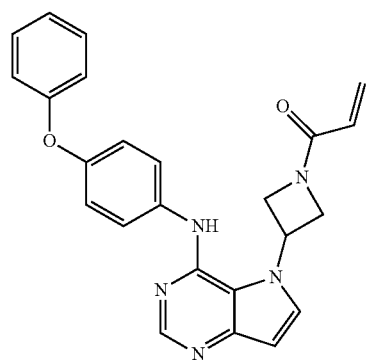
8
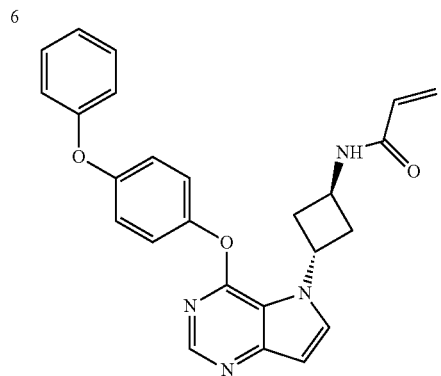
9
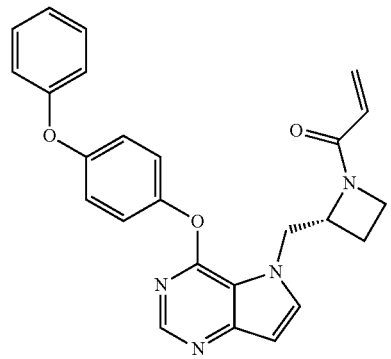
10
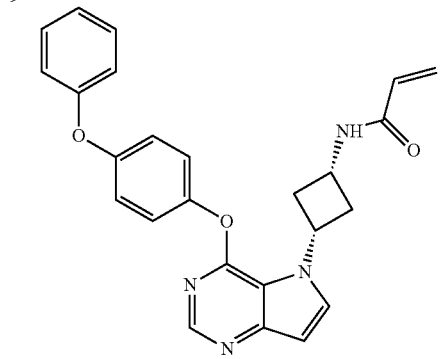

-continued
| 11 | 12 |
|---|---|
| 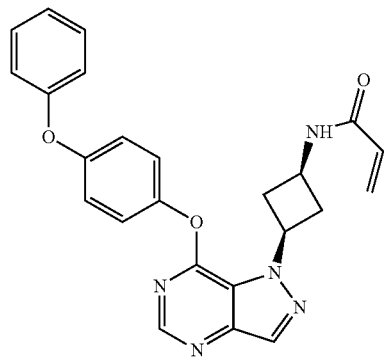 | 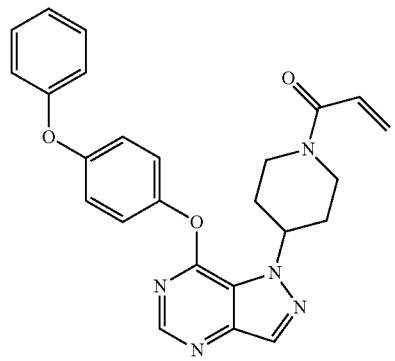 |
| 14 | 15 |
|---|---|
| 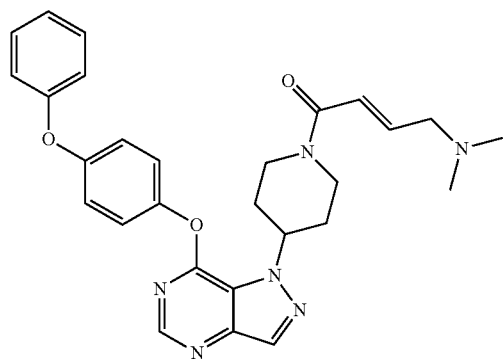 | 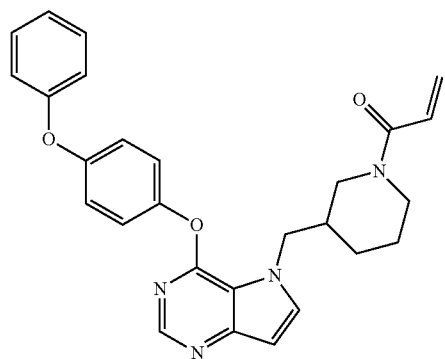 |
| 16 | 17 |
|---|---|
| 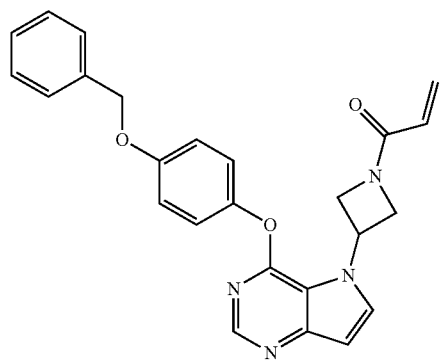 | 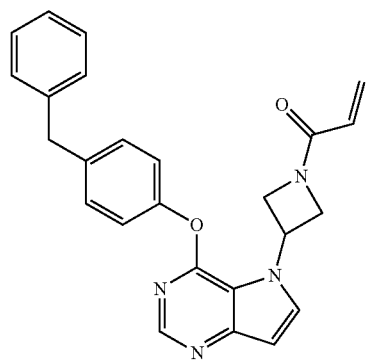 |
| 18 | 19 |
|---|---|
| 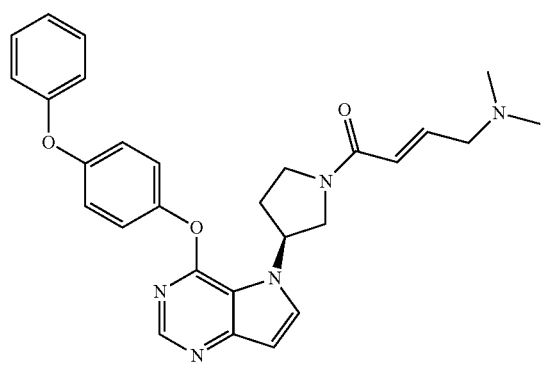 | 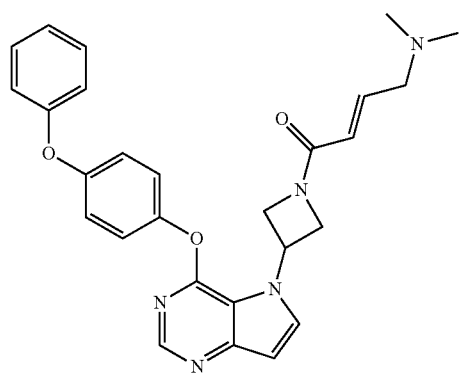 |

-continued
20
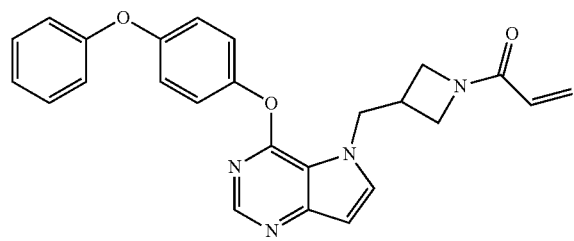
21
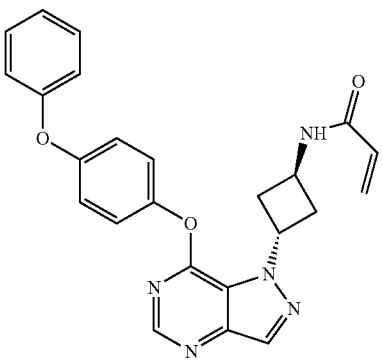
22
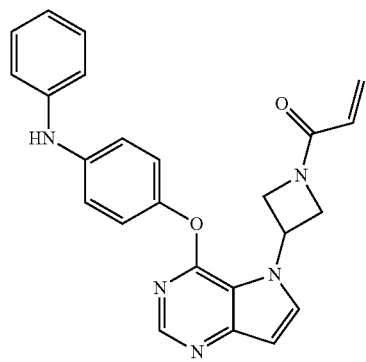
25
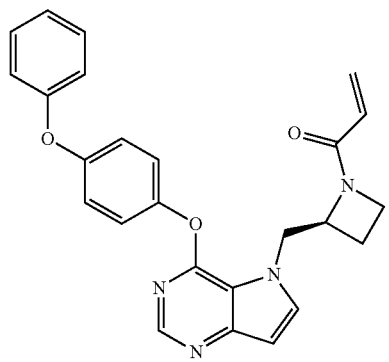
26
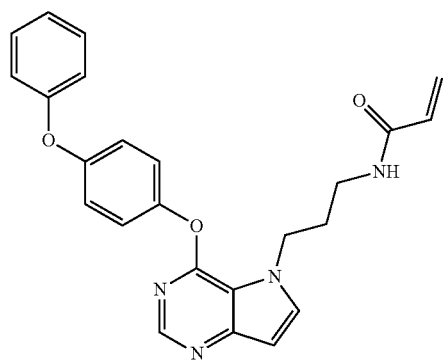
27
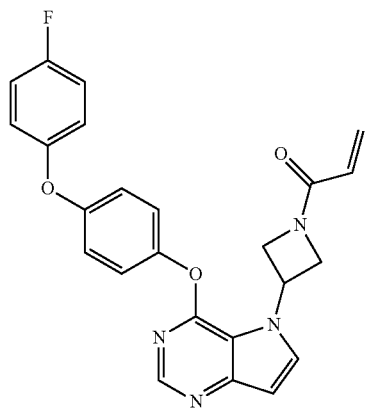

159
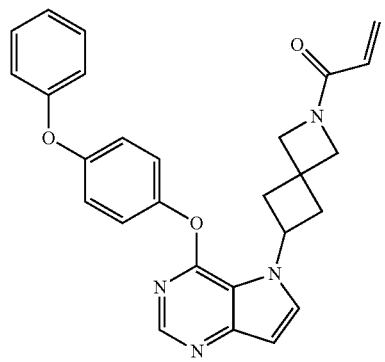
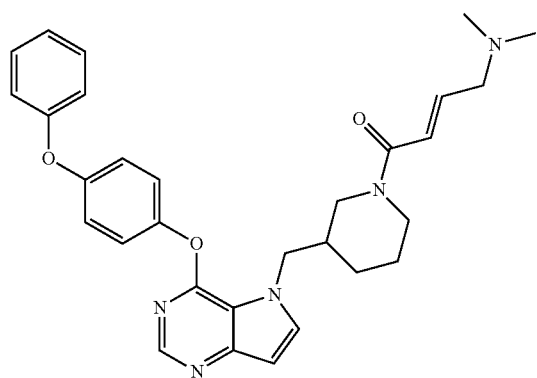
-continued
28
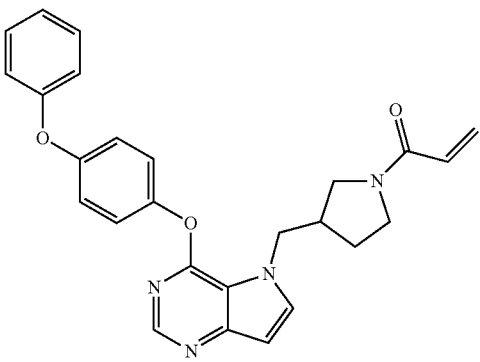
160
29
30
31
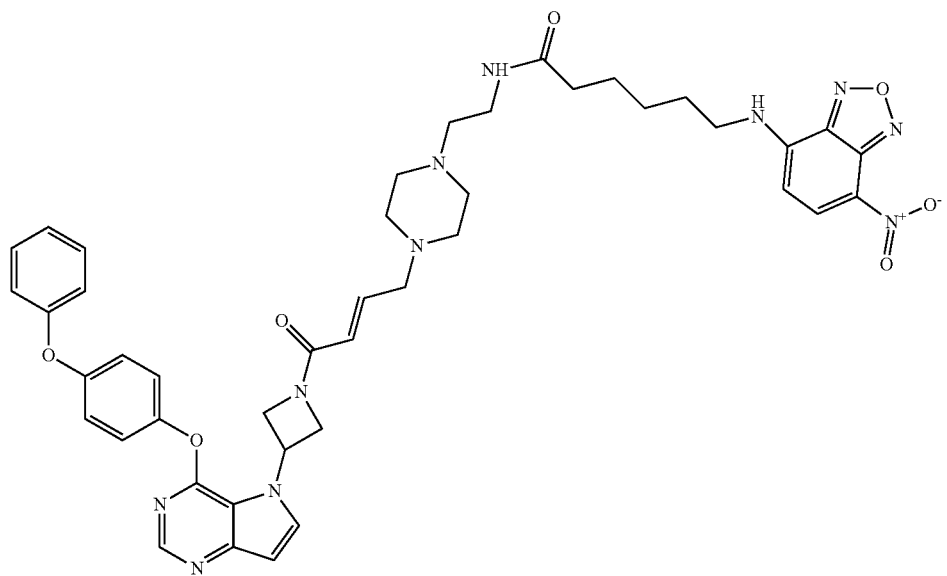

32
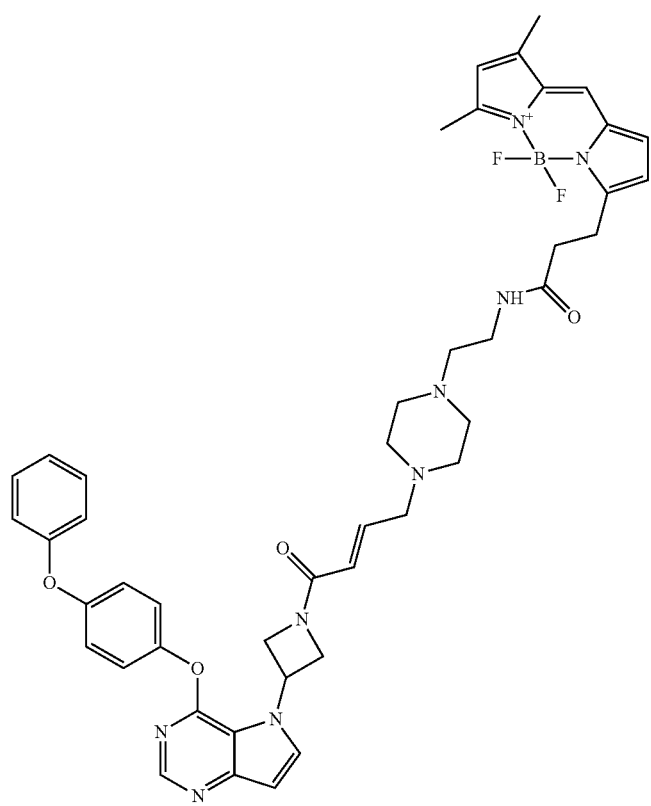
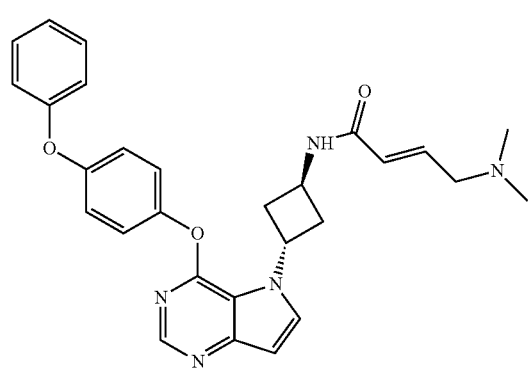
33
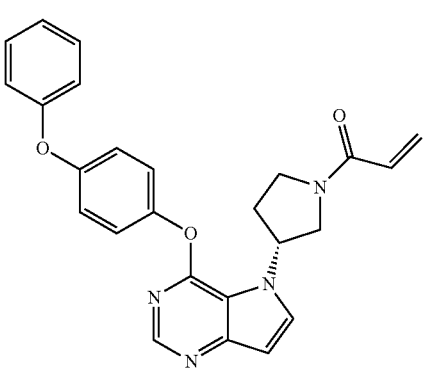
34
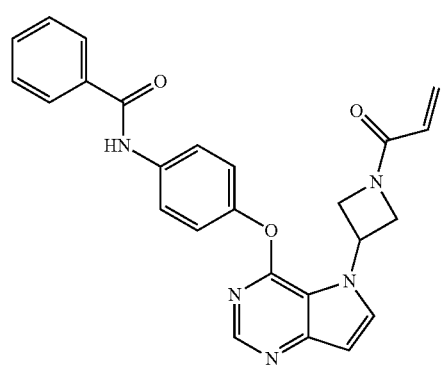
35
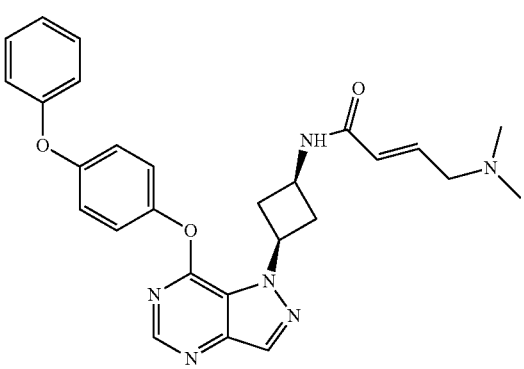
36

| 37 | 38 |
|---|---|
| 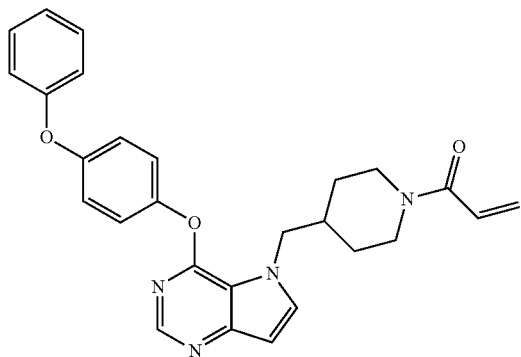 | 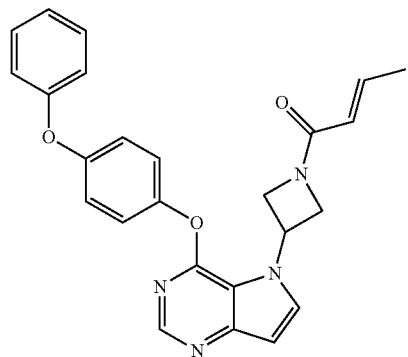 |
| 39 | 40 |
| 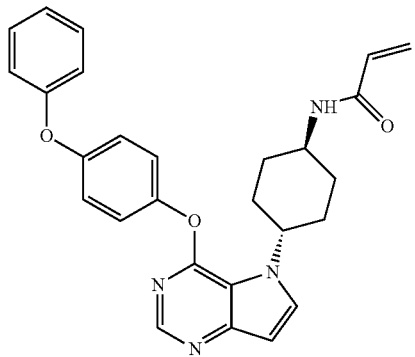 | 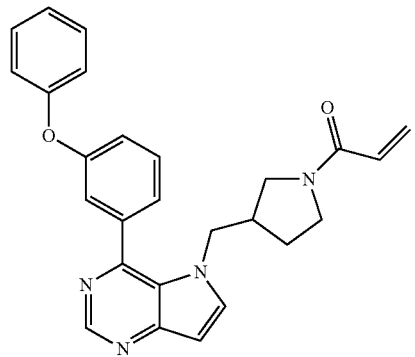 |
| 41 | 42 |
| 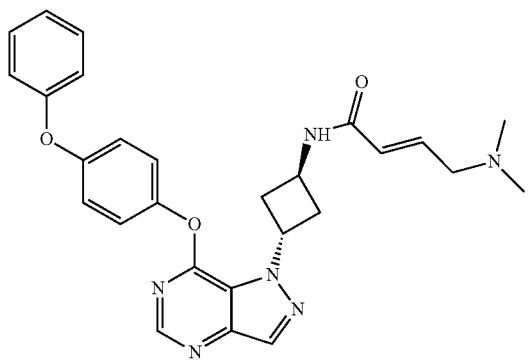 | 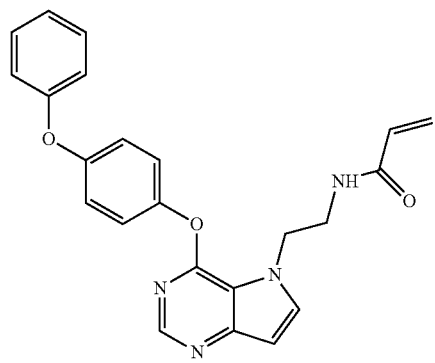 |
| 43 | 44 |
| 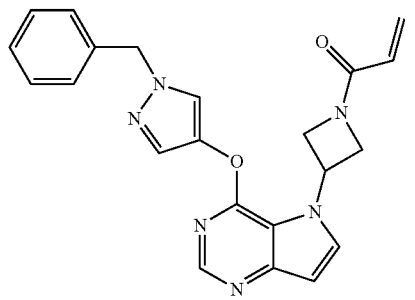 | 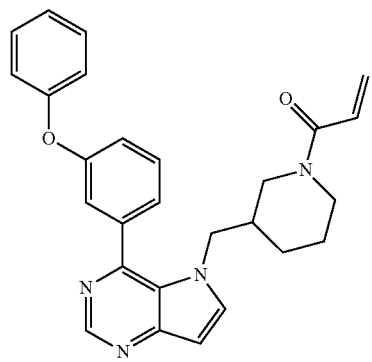 |

-continued
45
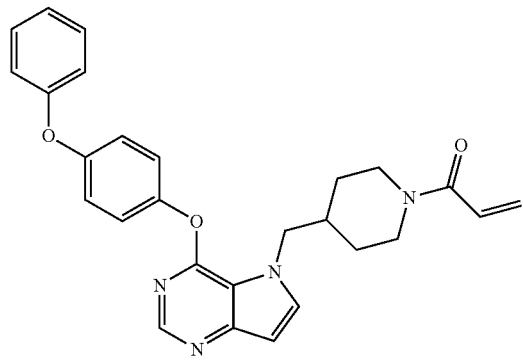
46
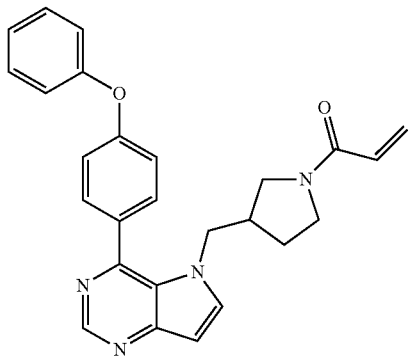
47
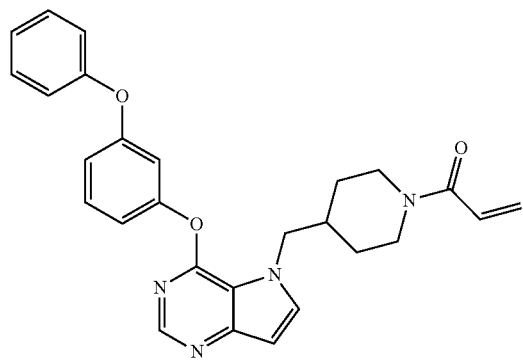
48
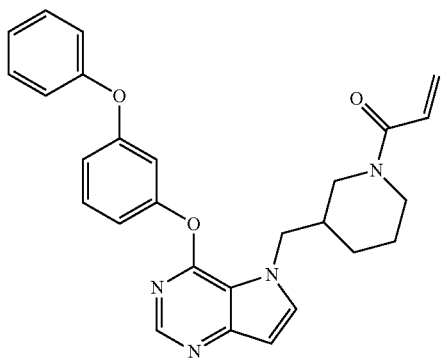
49
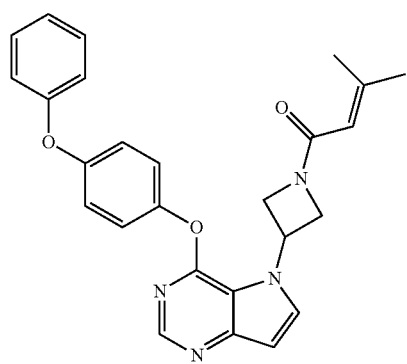
50
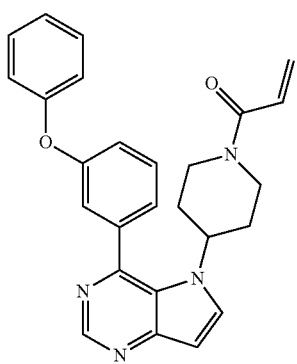
51
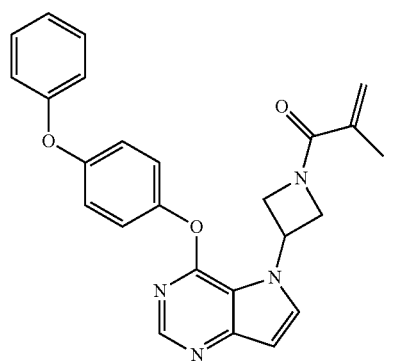

-continued
53
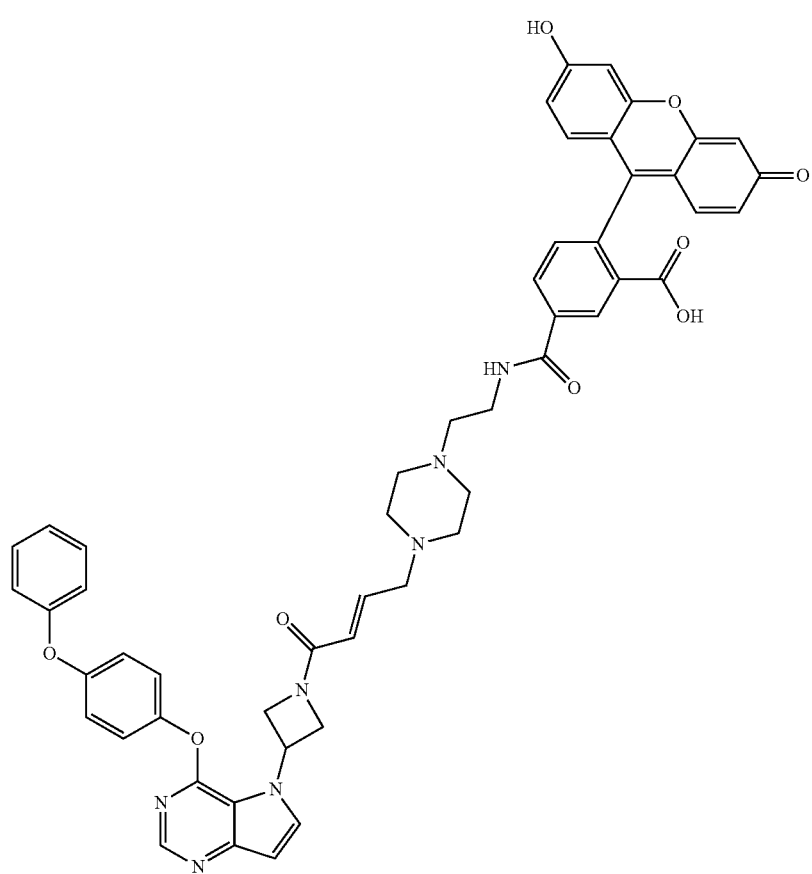
54
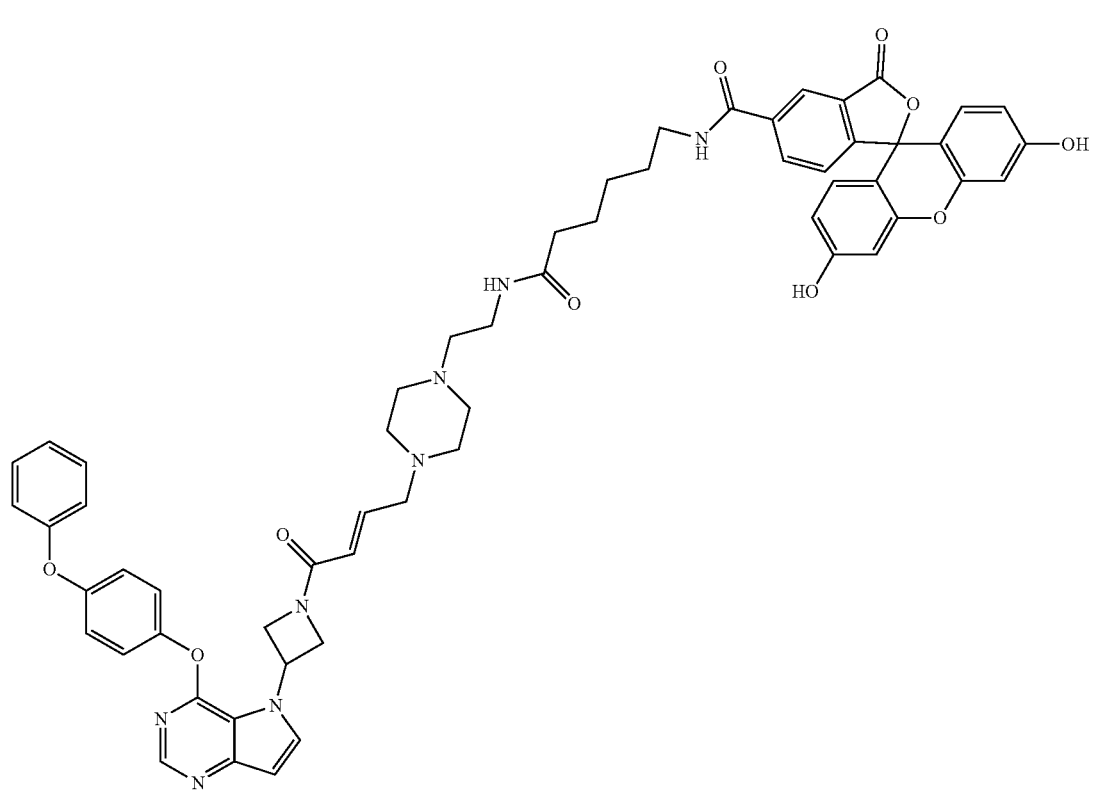

-continued
55
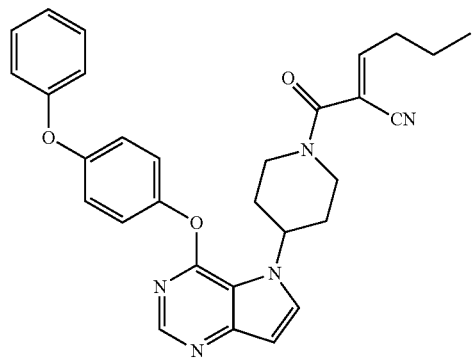
56
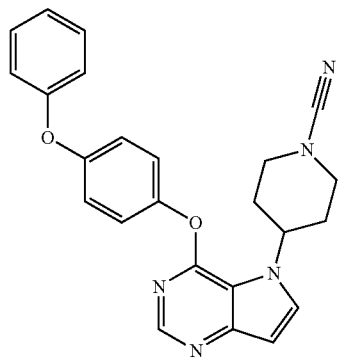
57
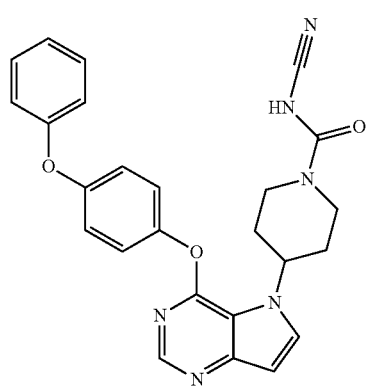
58
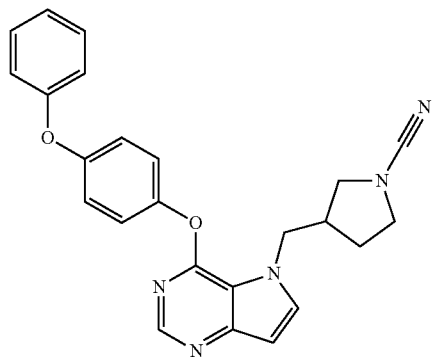
59
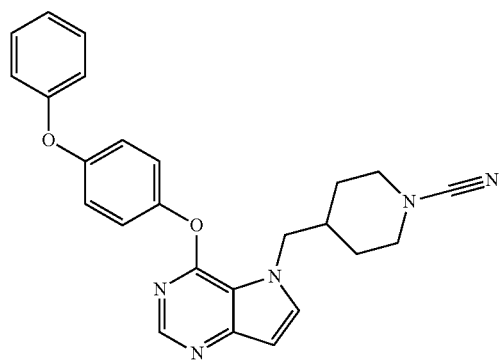
60
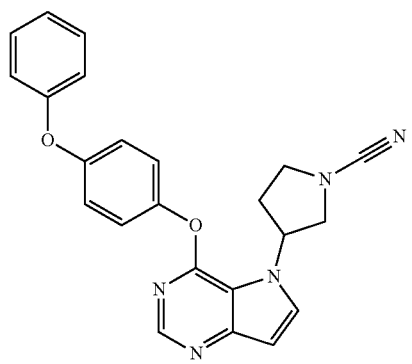

171                                  172
-continued
61                                   62
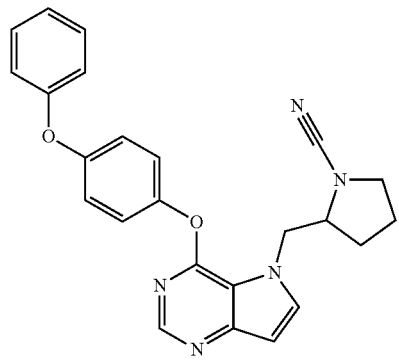
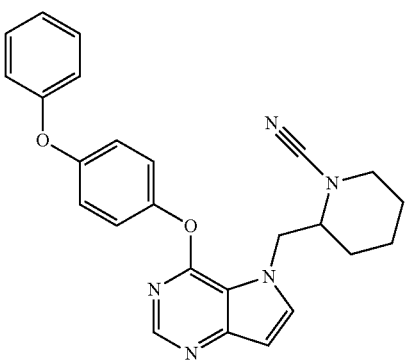
63                                   64
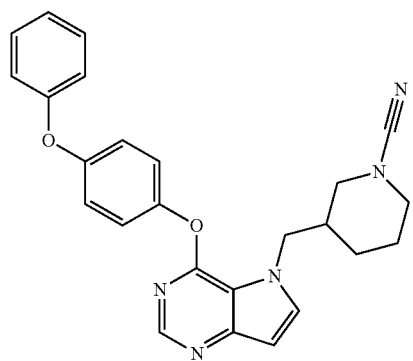
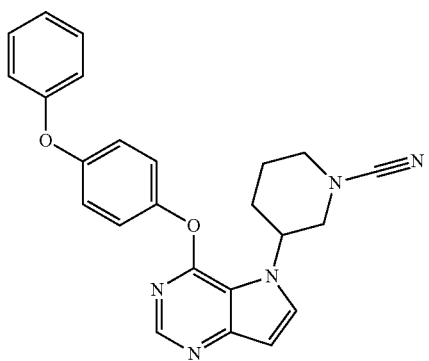
65                                   66
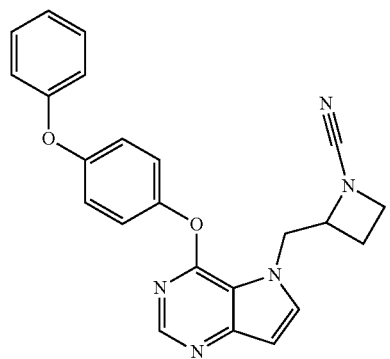
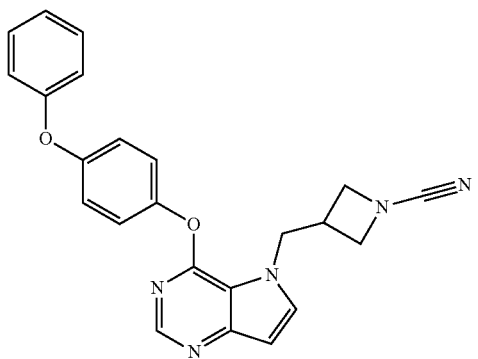
67                                   68
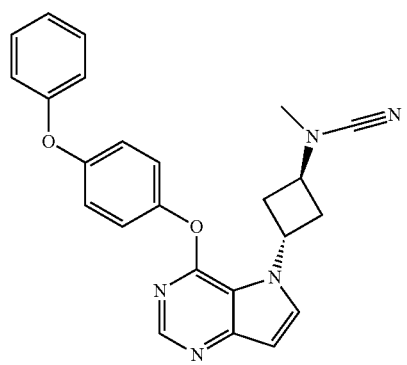
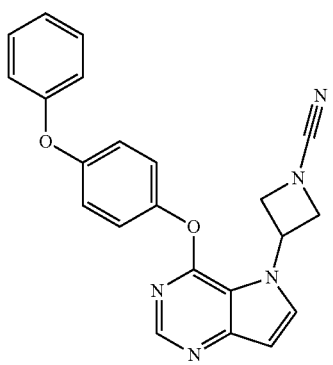

-continued
69
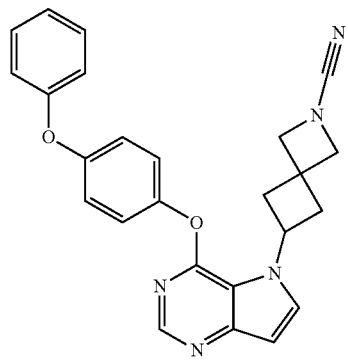
70
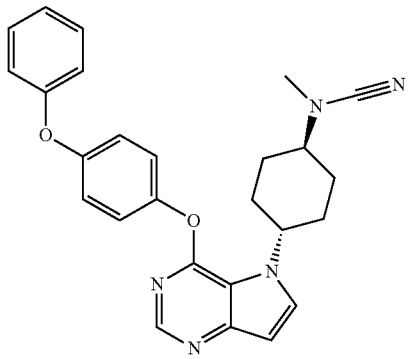
71
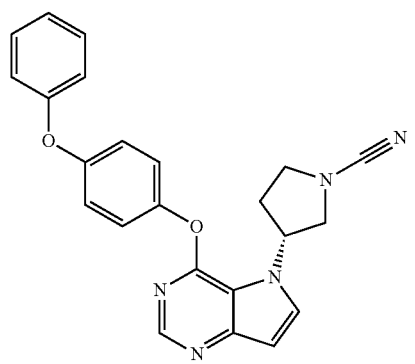
72
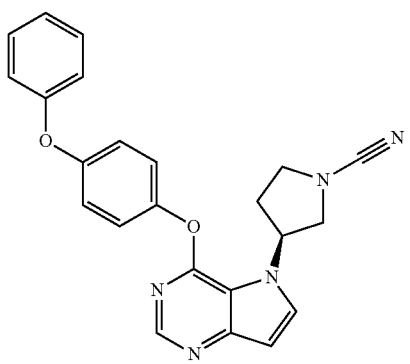
73
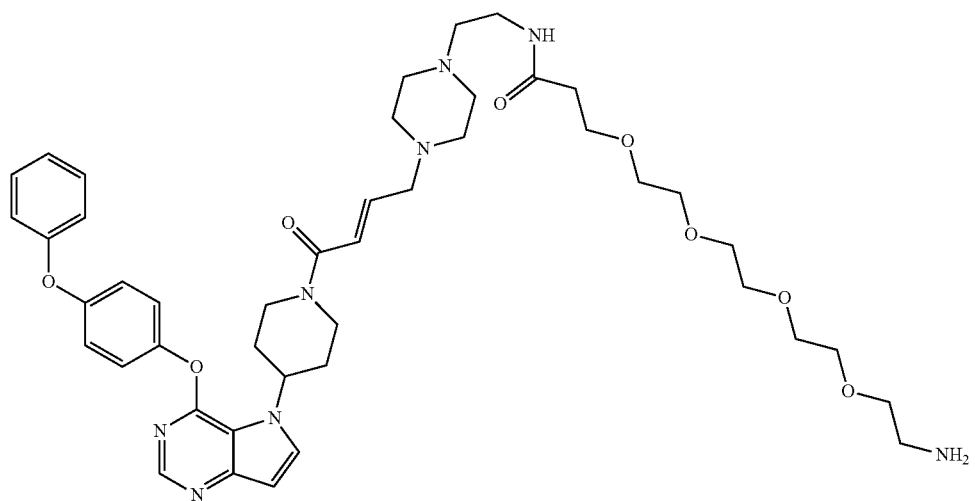

-continued
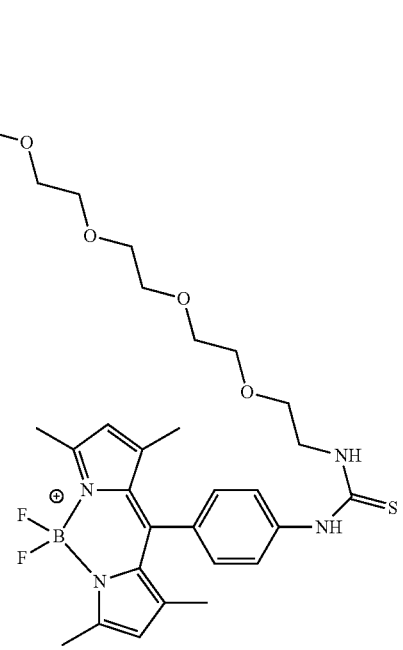
74
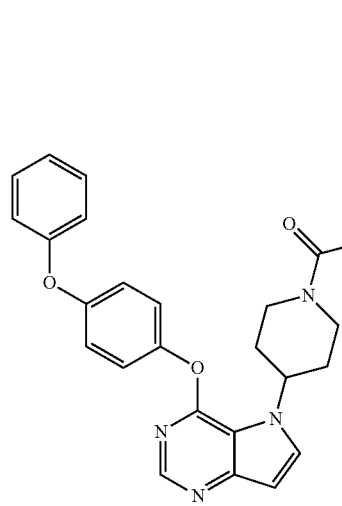
75
and
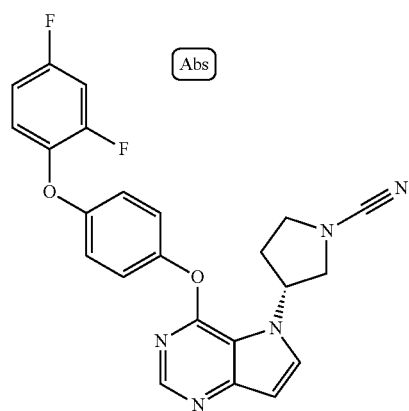
76
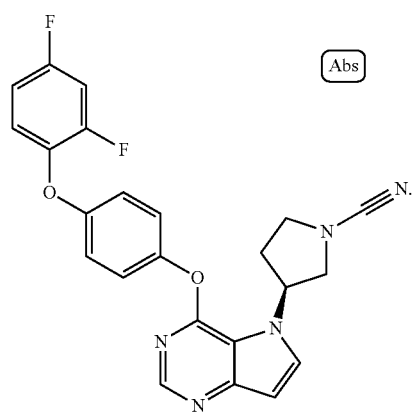

12. A pharmaceutical composition comprising a compound of claim 1, and a pharmaceutically acceptable adjuvant, carrier, or vehicle.

13. A process for manufacturing a compound of formula I according to claim 1, comprising the steps of:

reacting a compound of formula (II-a)

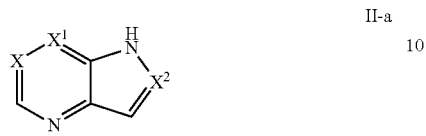

II-a wherein X, $X^1$, and $X^2$, are as defined in claim 1; with a compound to yield a compound of formula I:

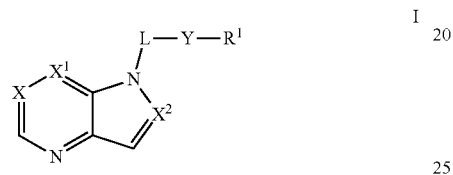

I wherein X, $X^1$, $X^2$, $R^1$, L and Y are as defined in claim 1.

* * * * *